US011939626B2

(12) United States Patent
Chiu et al.

(10) Patent No.: US 11,939,626 B2
(45) Date of Patent: *Mar. 26, 2024

(54) METHODS AND SYSTEMS FOR PERFORMING DIGITAL ASSAYS USING POLYDISPERSE DROPLETS

(71) Applicant: UNIVERSITY OF WASHINGTON THROUGH ITS CENTER FOR COMMERCIALIZATION, Seattle, WA (US)

(72) Inventors: Daniel T. Chiu, Seattle, WA (US); Jason E. Kreutz, Seattle, WA (US); Gloria S. Yen, Seattle, WA (US); Bryant S. Fujimoto, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,415

(22) Filed: Jul. 19, 2022

(65) Prior Publication Data
US 2022/0356512 A1 Nov. 10, 2022

Related U.S. Application Data

(63) Continuation of application No. 16/812,173, filed on Mar. 6, 2020, now Pat. No. 11,427,857, which is a continuation of application No. 15/301,798, filed as application No. PCT/US2015/024840 on Apr. 8, 2015, now Pat. No. 10,619,192.

(60) Provisional application No. 62/047,570, filed on Sep. 8, 2014, provisional application No. 61/976,918, filed on Apr. 8, 2014.

(51) Int. Cl.
| C12Q 1/6816 | (2018.01) |
| G01N 15/14 | (2006.01) |
| G01N 15/1434 | (2024.01) |
| G01N 21/47 | (2006.01) |
| G01N 21/64 | (2006.01) |
| G06T 7/62 | (2017.01) |
| G06V 20/69 | (2022.01) |

(52) U.S. Cl.
CPC ....... *C12Q 1/6816* (2013.01); *G01N 15/1434* (2013.01); *G01N 21/47* (2013.01); *G01N 21/6428* (2013.01); *G06T 7/62* (2017.01); *G06V 20/695* (2022.01); *G01N 2015/1445* (2013.01); *G01N 2021/6439* (2013.01); *G06T 2207/10056* (2013.01); *G06T 2207/30072* (2013.01)

(58) Field of Classification Search
CPC .. C12Q 1/6816; G01N 15/1434; G01N 21/47; G01N 21/6428; G01N 2015/1445; G06T 7/62; G06V 20/695
See application file for complete search history.

(56) References Cited

U.S. PATENT DOCUMENTS

| 5,665,539 A * | 9/1997 | Sano ............... C07K 14/31 435/7.1 |
| 9,428,793 B2 | 8/2016 | Chiu et al. |
| 10,000,797 B2 | 6/2018 | Chiu et al. |
| 2007/0298515 A1 | 12/2007 | Diamond et al. |
| 2009/0203063 A1 | 8/2009 | Wheeler et al. |
| 2010/0097590 A1 | 4/2010 | Schumaker |
| 2010/0105025 A1 | 4/2010 | Engelhard |
| 2010/0136544 A1 | 6/2010 | Agresti et al. |
| 2010/0321478 A1 | 12/2010 | Sliwa et al. |
| 2011/0261164 A1 | 10/2011 | Olesen et al. |
| 2012/0184464 A1 | 7/2012 | Lee et al. |
| 2012/0329038 A1 | 12/2012 | Smagilov et al. |
| 2013/0288254 A1 | 10/2013 | Pollack et al. |
| 2013/0302792 A1 | 11/2013 | Hindson et al. |
| 2014/0087386 A1 | 3/2014 | Chiu et al. |
| 2017/0145490 A1 | 5/2017 | Chiu et al. |
| 2018/0251827 A1 | 9/2018 | Chiu et al. |
| 2022/0008928 A1 | 1/2022 | Colston, Jr. et al. |

FOREIGN PATENT DOCUMENTS

| CN | 1974751 A | 6/2007 | |
| CN | 102405402 A | 4/2012 | |
| CN | 103429997 A | 12/2013 | |
| JP | 10-253522 A | 9/1998 | |
| JP | 2004-361291 A | 12/2004 | |
| JP | 2014505476 A | 3/2014 | |
| JP | 2017519484 A | 7/2017 | |
| WO | 2009003184 A1 | 12/2008 | |
| WO | 2010111265 A1 | 9/2010 | |
| WO | 2012100198 A2 | 7/2012 | |
| WO | 2012135667 A1 | 10/2012 | |
| WO | WO-2012135667 A1 * | 10/2012 | ............. C12Q 1/686 |
| WO | 2012/174142 A1 | 12/2012 | |
| WO | 2015157369 A1 | 10/2015 | |

OTHER PUBLICATIONS

Penfold(Langmuir 22.5 (2006): 2005-2015) (Year: 2006).*
European Search Report and Written Opinion dated Sep. 26, 2018, for European Patent Application No. 18184052.
Office Action dated Jun. 15, 2018, for Japanese Patent Application No. 2016221388 (with English Translation).
(Continued)

*Primary Examiner* — Sahana S Kaup
(74) *Attorney, Agent, or Firm* — Christensen O'Connor Johnson Kindness, PLLC

(57) ABSTRACT

Methods, devices, and systems for performing digital assays are provided. In certain aspects, the methods, devices, and systems can be used for the amplification and detection of nucleic acids. In certain aspects, the methods, devices, and systems can be used for the recognition, detection, and sizing of droplets in a volume. Also provided are compositions and kits suitable for use with the methods and devices of the present disclosure.

19 Claims, 25 Drawing Sheets

(56) References Cited

OTHER PUBLICATIONS

Kumaresan et al., "High-throughput single copy DNA amplification and cell analysis in engineered nanoliter droplets," Analytical Chemistry, 80(10): 3522-9, 2008.
Mazutis et al., "Droplet-Based Microfluidic Systems for High-Throughput Single DNA Molecule Isothermal Amplification and Analysis," Analytical Chemistry, 81(12):4813-4821, 2009.
Office Action dated Jan. 4, 20176, for Chinese Patent Application No. 201280012684.6.
Office Action dated Jun. 23, 2016, for Chinese Patent Application No. 201280012684.6.
Office Action dated Mar. 4, 2019, for Chinese Patent Application No. 201580029257.2.
Office Action dated Jul. 14, 2016, for Japanese Patent Application No. 2013-550633.
Sykes, et al. "Quantitation of targets for PCR by use of limiting dilution, " Biotechniques, 13(3):444-9, Sep. 1992.
Notice of Allowance dated Jan. 26, 2018, for U.S. Appl. No. 15/230,162.
Extended European Search Report and Search Opinion dated Nov. 9, 2017, for European Patent Application No. EP15776098.4.
Hindson, et al., "High-throughput droplet digital PCR system for absolute quantitation of DNA copy number," Analytical Chemistry, 83(22):8604-10, Nov. 15, 2011.
Nakano et al., "Single-molecule PCR using water-in-oil emulsion," Journal of Biotechnology, 102(2):117-24, 2003.
Office Action dated Jan. 4, 2017, for Chinese Patent Application No. 201580029257.2.
Office Action dated Apr. 8, 2016, for European Patent Application No. 12736553.4.
Office Action dated May 22, 2017, U.S. Appl. No. 15/230,162.
Office Action dated Jun. 23, 2016, for Chinese Patent Application No. 201580029257.2.
Office Action dated Nov. 14, 2017, for Japanese Patent Application No. 2016-221388.
Office Action dated Dec. 5, 2017, for U.S. Appl. No. 15/230,162.
Pinheiro et al., "Evaluation of a Droplet Digital Polymerase Chain Reaction Format for DNA Copy Number Quantification," Analytical Chemistry, 84(2):1003-11, Jan. 17, 2012.
Penfold, et al., "Quantitative imaging of aggregated emulsions," Langmuir, 22(5):2005-15, Feb. 28, 2006.
Office Action dated Oct. 10, 2015, for Chinese Patent Application No. 201280012684.6.
Cohen, et al., "Self-Digitization of Sample Volumes," Analytical Chemistry, 82(13):5707-5717, Jul. 1, 2010.
Yan, "Image analysis and platform development for automated phenotyping in cytomics," Doctoral Dissertation, Leiden University, Nov. 27, 2013, retrieved from <https://openaccess.leidenuniv.nl/bitstream/handle/1887/22550/PROEF.KUANYAN.THESIS.pdf?sequence=18>. (132 pages).
Dube, et al., "Mathematical analysis of copy number variation in a DNA sample using digital PCR on a nanofluidic device," PLOS One, 3(8): e2876, Aug. 6, 2008.
European Examination Report dated Aug. 3, 2015, for European Patent Application No. 12736553.4.
European Search Report and Opinion dated Apr. 17, 2014, for European Patent Application No. 12736553.4.
Gansen, et al., "Digital LAMP in a sample self-digitization (SD) chip," Lab Chip, 12(12):2247-54, Jun. 21, 2012.
Hanson, et al., "Nanoscale double emulsions stabilized by single-component block copolypeptides," Nature, 455(7209):85-8, Sep. 4, 2008.
International Preliminary Report on Patentability dated Aug. 1, 2013, for International Patent Application No. PCT/2012/022081.
International Search Report and Written Opinion dated Jul. 8, 2015, for International Patent Application No. PCT/2015/024840.
International Search Report and Written Opinion dated Aug. 7, 2012, for International Patent Application No. PCT/2012/022081.
Kreutz, et al., "Theoretical design and analysis of multivolume digital assays with wide dynamic range validated experimentally with microfluidic digital PCR," Analytical Chemistry, 83(21):8158-68, Nov. 1, 2011.
Lieber, "Statistical significance and statistical power in hypothesis testing," J Orthop Res, 8(2):304-9, Mar. 1990.
Notification of Filing Divisional Application dated Mar. 30, 2015, for Chinese Patent Application No. 201280012684.6.
Zeng, et al. "High-performance single cell genetic analysis using microfluidic emulsion generator arrays," Analytical Chemistry, 82(8):3183-90, Apr. 15, 2010.
Schneider, et al., "The potential impact of droplet microfluidics in biology," Analytical Chemistry, 85(7):3476-82, Apr. 2, 2013.
Shen, et al., "Multiplexed quantification of nucleic acids with large dynamic range using multivolume digital RT-PCR on a rotational SlipChip tested with HIV and hepatitis C viral load," J Am Chem Soc, 133(44):17705-12, Nov. 9, 2011.
Japanese Office Action dated Dec. 18, 2020, for Japanese Patent Application No. 2019-227458, 5 pages.
Second Office Action dated Apr. 7, 2020, issued in corresponding Chinese Application No. 201580029257.2, filed Apr. 8, 2015, 12 pages.
Third Office Action dated Jul. 14, 2020, issued in corresponding Chinese Application No. 201580029257.2, filed Apr. 3, 2015, 5 pages.
Extended European Search Report dated Jul. 4, 2020, issued in corresponding Divisional European Application No. 19214238.8, filed Apr. 8, 2015, 10 pages.
Co-pending U.S. Appl. No. 15/962,944, filed Apr. 25, 2018.
Co-pending U.S. Appl. No. 15/230,162, filed Aug. 5, 2016.
Japanese Notice of Reasons for Refusal dated Oct. 12, 2022, issued in the corresponding Japanese Application No. 2021-145212, filed on Apr. 8, 2015, and its English translation thereof, 8 pages.
Japanese Office Action dated Mar. 15, 2023, issued in corresponding Japanese Application No. 2021-145212 filed on Apr. 8, 2015, and its English translation thereof.
Communication Pursuant to Article 94(3) EPC dated Sep. 19, 2023, issued in the corresponding European App. No. 19214238.8, filed on Apr. 8, 2015, 5 pages.
English translation of the Chinese Office Action dated Dec. 27, 2023, issued in the corresponding Chinese Application No. 202110156648.8, 5 pages.

* cited by examiner

METHODS AND SYSTEMS FOR PERFORMING DIGITAL ASSAYS USING POLYDISPERSE DROPLETS

CROSS-REFERENCE

This application is a continuation of U.S. application Ser. No. 16/812,173, filed Mar. 6, 2020, which is a continuation of U.S. application Ser. No. 15/301,798, filed Oct. 4, 2016, which is a national stage entry of International Application No. PCT/US2015/024840, filed Apr. 8, 2015, which claims the benefit of U.S. Provisional Application No. 61/976,918, filed Apr. 8, 2014, and U.S. Provisional Application No. 62/047,570, filed Sep. 8, 2014, all of which are incorporated herein by reference in their entirety.

STATEMENT AS TO FEDERALLY SPONSORED RESEARCH

This invention was made with government support under R21 GM103459, awarded by the National Institutes of Health. The government has certain rights in the invention.

BACKGROUND OF THE INVENTION

Digital assays, in which measurements are made based on a counting of binary yes or no responses, are increasingly important in biology, owing to their robustness, sensitivity and accuracy. Whereas analog measurements often require calibration with a running standard, digital measurements do not require calibration, and have the potential to be faster, easier to implement, more accurate, and more robust than analog methods.

An important application for digital assays is accurate detection and measurement of DNA or RNA in a sample. The most commonly used method to detect DNA in a sample is polymerase chain reaction (PCR), wherein DNA is amplified in a temperature-sensitive reaction catalyzed by a DNA-polymerizing enzyme. In PCR the sample is typically cycled between two or three temperatures ranging from about 60° C. to about 95° C. by a thermal cycling device. The use of PCR to amplify DNA has greatly advanced a wide range of disciplines, from basic biology to clinical diagnostics and forensics. One particular form of PCR that is often used in diagnostics and biomedical research is quantitative PCR (qPCR), which not only detects the presence of DNA in the sample, but also provides an accurate measure of its concentration.

The most commonly used method for conducting qPCR is real-time PCR, wherein the absolute concentration of a sample is inferred from the time evolution of the amplification process, which is monitored repeatedly during the thermal cycling process with a fluorescent probe, such as a molecular beacon or Taqman probe, that specifically recognizes the amplification product.

Real-time PCR is susceptible to various errors, including the formation of unwanted primer dimers, where primer molecules attach to each other because of complementary stretches in their sequence. As a result, a by-product is generated that competes with the target element for available PCR reagents, thus potentially inhibiting amplification of the target sequence and interfering with accurate quantification. The quantification of target also requires precise knowledge of the amplification efficiency for each cycle, and because the growth is exponential, tiny uncertainties in amplification efficiency (e.g., below the threshold detection level) will result in very large errors in the determination of target copy numbers. This error can become very large when the initial concentration of nucleic acid is low or when the fluorescence detection is not sufficiently sensitive. Thus, despite its power to identify and quantify target DNA from complex samples, real-time PCR is not able to reliably and precisely quantify low sample concentrations, as required for example in the detection of pathogens or clinical diagnostics.

The limits of real-time PCR to quantify low copy-number DNA accurately can potentially be overcome using digital PCR (dPCR). In dPCR, a volume containing a sample is divided into an array of smaller volumes, such that, based on Poisson statistics, at least some of the volumes do not contain target DNA, while the rest can contain one or more target molecules. DNA amplification is then carried out in an array of the smaller volumes simultaneously, resulting in an increase in fluorescence (or other signal) in only those volumes that contained one or more target molecules prior to amplification. The DNA copy number can be easily and accurately determined by knowing the volumes and the number of wells with an increased signal (i.e., those that contain amplified DNA) compared to the total number of wells.

Most existing digital assays rely on a count of binary responses obtained from volumes of invariant size, such as monodisperse droplet emulsions. While advances in microfluidic systems have enabled the generation of monodisperse droplet emulsions, these systems are technically difficult, resulting in increased time and cost for the end-user when compared with conventional analog methods.

Given the limitations inherent in analog assays such as real-time PCR, and the technical difficulties of existing digital assays, it is clear that there is a need to provide improved methods and apparatuses for performing digital assays. The invention described herein addresses this need and more.

SUMMARY OF THE INVENTION

The present disclosure provides methods, systems, compositions and kits for performing digital assays. The present disclosure relates in part to the surprising discovery digital assays can be performed in systems containing polydisperse droplets without the introduction of undue experimental error.

In various aspects, the present methods, systems, compositions and kits can be used to perform digital PCR assays involving the amplification of a nucleotide sample.

In various aspects, the present disclosure provides methods for performing a digital assay, comprising: producing a plurality of polydisperse droplets, wherein at least some of the droplets comprise a sample; amplifying the sample; labeling the sample with a detectable agent; obtaining an image stack for a droplet; determining from the image stack the volume of the droplet; determining from the image stack the presence or absence of the detectable agent in the droplet; and determining the concentration of the sample in the plurality of droplets based on the presence or absence of the detectable agent in a plurality of droplets.

In some aspects, the present disclosure provides methods for performing a digital assay, comprising: producing a plurality of polydisperse droplets, wherein at least some of the droplets comprise a sample; amplifying the sample; labeling the sample with a detectable agent; flowing the plurality of polydisperse droplets through a flow cytometry channel; determining the volume of a droplet as it flows through the flow cytometry channel; determining the presence or absence of the detectable agent in the droplet; and determining the concentration of the sample in the plurality of droplets based on the presence or absence of the detectable agent in a plurality of droplets.

In various aspects, the present disclosure provides compositions and kits for performing a digital assay comprising: a first fluid; a second fluid, wherein the first fluid and the second fluid are immiscible in each other and are capable of forming an emulsion when physically agitated; a surfactant; and an amplification reagent.

In various aspects, the present disclosure provides methods, compositions and kits for performing digital assays using double emulsions. In some aspects, the double emulsion comprises two aqueous phases and an oil phase.

In various aspects, the present disclosure provides methods for performing a digital assay. A plurality of polydisperse droplets may be produced. At least some of the droplets may comprise a sample. The sample may be amplified. The sample may be labeled with a detectable agent. An image stack for a droplet may be obtained. The volume of the droplet may be determined from the image stack. The presence or absence of the detectable agent in the droplet may be determined from the image stack. The concentration of the sample in the plurality of droplets may be determined based on the presence or absence of the detectable agent in the plurality of droplets.

In various aspects, the present disclosure provides methods for performing a digital assay. A plurality of polydisperse droplets may be produced. At least some of the droplets may comprise a sample. The sample may be amplified. The sample may be labeled with a detectable agent. The plurality of polydisperse droplets may be flowed through a flow cytometry channel. The volume of a droplet may be determined as it flows through the flow cytometry channel. The presence or absence of the detectable agent in the droplet may be determined. The concentration of the sample in the plurality of droplets may be determined based on the presence or absence of the detectable agent in the plurality of polydisperse droplets. In some aspects, the size of the droplet may be determined by detecting light scattered from the droplet. The concentration of the sample in the plurality of polydisperse droplets may be determined based on the sizes or size distribution of the droplets.

In various aspects, the present disclosure provides compositions for performing digital assays. A composition may comprise a first fluid, a second fluid, a surfactant, and an amplification reagent. The first fluid and the second fluid may be immiscible in each other and may be capable of forming an emulsion when agitated. In some aspects, the composition may further comprise a sample, such as a nucleotide, and/or a detectable agent capable of labeling the sample.

In various aspects, the present disclosure provides systems for determining a volume of at least one droplet. The system may comprise a container, an imaging source, and a computing device. The container may be configured for holding the droplet(s). The imaging source may be configured to obtain an image of the droplet(s) in the container. The computing device may comprise a processor and a memory (e.g., a non-transitory, tangible computer-readable storage medium such as a ROM, RAM, flash memory, or the like). The memory may store a set of instructions that when executed by the processor cause (i) the imaging source to obtain an image stack of the droplet(s) and (ii) the processor to determine the volume of the droplet(s) in the sample based on the obtained image stack.

In various aspects, the present disclosure provides methods for determining a volume of a droplet. An image stack of the droplet may be obtained. A pixel set(s) in an individual image of the image stack may be identified. The pixel set(s) may be identified as corresponding to at least a part of at least one droplet. An individual droplet(s) may be identified from the pixel set(s) based on the correspondence. The volume of the identified individual droplet(s) may be determined based on the at least one pixel set. The part of at least one droplet may comprise a part of a single droplet, parts of multiple droplets, a whole droplet, a plurality of whole droplets, or combinations thereof.

In various aspects, the present disclosure provides systems for performing digital assays. The system may comprise a container, an imaging source, and a computing device. The container may be configured for holding a plurality of polydisperse droplets. At least some of the droplets may comprise a sample labeled with a detectable agent. The imaging source may be configured to obtain an image stack of the plurality of polydisperse droplets held in the container. The computing device may be configured to operate the imaging source. The computing device may comprise a processor and a memory (e.g., a non-transitory, tangible computer-readable storage medium such as a ROM, RAM, flash memory, or the like). The memory may store a set of instructions that when executed by the processor cause (i) the imaging source to obtain the image stack of the plurality of polydisperse droplets held in the container, (ii) the processor to determine the volumes of the plurality of polydisperse droplets based on the obtained image stack, (iii) the processor to determine the presence or absence of the detectable agent in the plurality of polydisperse droplets, and (iv) the processor to determine the concentration of the sample in the plurality of droplets based on the presence or absence of the detectable agent in the plurality of polydisperse droplets and the volumes of the plurality of polydisperse droplets.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
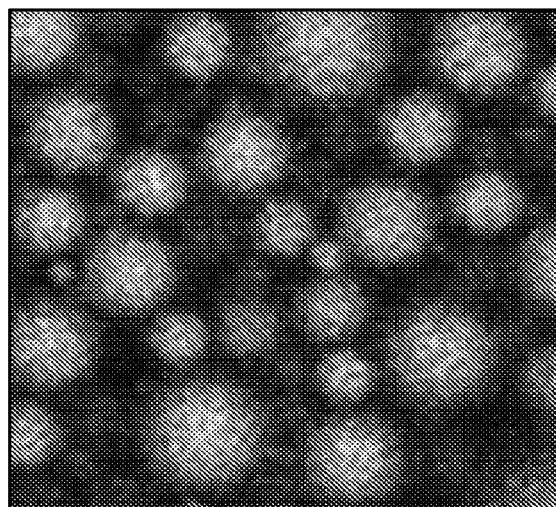
FIG. 1 is a gray-scale image of an exemplary polydisperse droplet emulsion system obtained using confocal fluorescent microscopy.

The present disclosure relates to methods and systems for performing digital assays using polydisperse droplets. In particular, the present disclosure relates to methods for the amplification and analysis of samples in polydisperse droplet systems. The present methods and systems can be used to identify droplets in a polydisperse droplet system, determine whether that droplet contains a sample of interest, and the performance of assay steps, such as for example, digital polymerase chain reaction (dPCR).

The methods and systems of the present disclosure advantageously enable the performance of high-throughput amplification and analysis of samples through the use of polydisperse droplets. The present disclosure exhibits significantly improved dynamic ranges in the performance of a digital assay by generating volumes of variable size. For a given sample concentration, the size of the volumes can define the probability of being occupied by one or more molecules (e.g., template molecules) of interest. In the example of amplification-related techniques, variation of volume size can be used to alter this occupational probability and thus the number of wells or sample volumes (e.g., droplets) that show amplification. Notably, the present disclosure improves upon existing techniques that simply increase the number of volumes with constant size so as to increase the dynamic range. Unlike the existing methods, the use of variable-volume samples eliminates the need to use a large area to accommodate the volumes needed to expand dynamic range, which, e.g., increases the likelihood of defects on a chip where some digitized volumes do not form properly or have other defects. In addition, increasing the number of volumes also increases the time required to analyze all those digitized volumes.

The present disclosure provides devices, systems and apparatuses that can be used in the generation, manipulation, analysis, and modeling of polydisperse droplet samples. Related methods are also provided. The disclosure also includes a method for the analysis of digital quantification platforms. While designed to enable digital assays using polydisperse platforms, the disclosure can also be applied to the digital assays using monodisperse emulsion platforms. The disclosure also includes methods for emulsion distribution modeling, data acquisition and emulsion generation.

Some aspects of the present disclosure include methods and apparatuses for the manipulation and analysis of species that comprise, but are not limited to, chemicals, biochemicals, genetic materials (e.g., DNA, RNA, and the like), expressed products of genetic materials, proteins, metabolites, peptides, polypeptides, crystallizing molecules, or biological cells including rare cells, cellular fractions, organelles, exosomes, mitochondria, drugs, biological particles that circulate in peripheral blood or lymphatic systems, or particles.

In some aspects, the apparatus, devices, methods and systems of the present disclosure can be used to amplify a polynucleotide sample, such as with polymerase chain reaction (PCR), reverse transcriptase PCR (RT-PCR), ligase chain reaction (LCR), loop mediated amplification (LAMP), reverse transcription loop mediated amplification (RT-LAMP), helicase dependent amplification (HDA), reverse transcription helicase dependent amplification (RT-HDA), recombinase polymerase amplification (RPA), reverse transcription recombinase polymerase amplification (RT-RPA), catalytic hairpin assembly reactions (CHA), hybridization chain reaction (HCR), entropy-driven catalysis, strand displacement amplification (SDA), and/or reverse transcription strand displacement amplification (RT-SDA). In certain aspects, the apparatus, devices, methods and systems of the present disclosure can be used for nucleic acid sequence based amplification (NASBA), transcription mediated amplification (TMA), self-sustained sequence replication (3SR), and single primer isothermal amplification (SPIA). Other techniques that can be used include, e.g., signal mediated amplification of RNA technology (SMART), rolling circle amplification (RCA), hyper branched rolling circle amplification (HRCA), exponential amplification reaction (EXPAR), smart amplification (SmartAmp), isothermal and chimeric primer-initiated amplification of nucleic acids (ICANS), and multiple displacement amplification (MDA). Other aspects can include the crystallization of proteins and small molecules, the manipulation and/or analysis of cells (e.g., rare cells or single cells), the manipulation and/or analysis of other biological particles (e.g., isolated mitochondria, bacteria, viral particles), or other biological or chemical components.

Polydisperse Droplet Emulsions for Digital Assays

The present disclosure provides methods, systems, and devices for performing digital assays with increased dynamic range, where a large number of volumes of varying size is generated. Unlike existing platforms, the methods and systems of the present disclosure can include use of a distribution of sizes (e.g., volumes) that is continuous rather than discrete. In some aspects, droplets of variable size can be created in various ways, either randomly or through controlled application of microfluidics. For example, microfluidic generation of constant volume droplets is well known in the art by using a T-junction or flow-focusing device. In these systems, the size of the droplet can be controlled by the shear rate and channel dimensions. If for a given T-junction geometry the shear rate is continuously varied, droplets of different volumes can be generated. These methods can be realized, e.g., by computer-controlled syringe pumps or modulated air pressure, which adjusts the relative flow speeds of the aqueous phase and the oil carrier fluid.

In various aspects of the present disclosure, an emulsion of polydisperse droplets can be produced between two or more immiscible fluids. As used herein, the term "immiscible fluids" means two or more fluids that, under a given set of experimental conditions, do not undergo mixing or blending to an appreciable degree to form a homogeneous mixture, even when in physical contact with one another.

As described further herein, the volumes used for digital measurements can be generated and analyzed by a variety of ways. The present disclosure includes a sample holder that can be used to hold the volumes so that the volumes can be further processed and/or analyzed. The sample holders of the present disclosure can include test tubes, microcentrifuge tubes, arrays of wells in a standard multi-well plate, arrays of wells on a microarray or in a microfluidic chip, a microfluidic chip configured to generate droplets, as well as other commercially available or otherwise generally known devices capable of holding discrete volumes (e.g., wells or droplets) of a sample.

In some aspects, droplets of various sizes can be generated randomly, by emulsification in a sample holder (e.g., a test tube). Droplet randomness can simplify the experiment because, e.g., no effort need be made to control the size of droplets. During emulsification, droplets of different volume can be stabilized with the use of any suitable surfactants. The emulsification approach is particularly useful for several reasons: (1) the method is compatible with basic instrumentation found in every biomedical laboratory, (2) droplet generation is simple; it does not require complex chip design or sophisticated equipment for flow control, (3) the droplets are not confined in individual wells, which minimizes the space required to accommodate a large number of droplets and (4) the assay is simple because the same container can be used for droplet generation and droplet storage during amplification. Advantageously, using this method, no sample transfer is needed between droplet generation and the amplification reaction.

Some aspects of the present disclosure include producing droplets in immiscible fluids. As is well known in the art, a wide variety of immiscible fluids can be combined to produce droplets of varying volumes. As described further herein, the fluids can be combined through a variety of ways, such as by emulsification. For example, an aqueous solution (e.g., water) can be combined with a non-aqueous fluid (e.g., oil) to produce droplets in a sample holder or on a microfluidic chip. Aqueous solutions suitable for use in the present disclosure can include a water-based solution that can further include buffers, salts, and other components generally known to be used in detection assays, such as PCR. Thus, aqueous solutions described herein can include, e.g., primers, nucleotides, and probes. Suitable non-aqueous fluids can include, but are not limited to, an organic phase fluid such as a mineral oil (e.g., light mineral oil), a silicone oil, a fluorinated oil or fluid (e.g., a fluorinated alcohol or Fluorinert), other commercially available materials (e.g., Tegosoft), or a combination thereof.

Emulsions can be generated in a variety of ways. According to certain aspects of the present disclosure, an emulsion can be generated by agitation, which is typically physical agitation. Some methods of physical agitation for emulsion generation include, but are not limited to, shaking, vortexing (that can include vortexing individual tubes or entire well plates or other devices), sonicating, mixing with magnets, rapid pipetting or some other extrusion method, or via flow focusing within microfluidic devices, among other methods. The agitation used according to the present disclosure can be any suitable agitation means that is sufficient to give rise to an emulsion. For example, the speed, degree, and time used for vortexing, sonicating, pipetting, extrusion or other agitation methods can readily be adjusted such that it is sufficient to give rise to an emulsion system of the present disclosure. The particular characteristics of the emulsion can be tuned by adjusting the chemical components in the system and the agitation conditions that the system is subjected to.

A variety of fluids or liquids can be used to prepare an emulsion according to the present disclosure. In some aspects, the system includes two or more immiscible fluids, that when mixed under appropriate conditions, separate into a dispersed droplet phase and a continuous carrier phase. For example a first fluid, which will become the dispersed droplet phase, can contain a sample. In some aspects, this first fluid will be an aqueous solution. In some aspects, this first fluid will remain a liquid, in other aspects, it can be, or become, a gel or a solid. In some aspects, this first fluid can have or can form a distinct shell.

Possible aqueous fluids that can be used as one phase of a droplet emulsion include, but are not limited to, various PCR and RT-PCR solutions, isothermal amplification solutions such as for LAMP or NASBA, blood samples, plasma samples, serum samples, solutions that contain cell lysates or secretions or bacterial lysates or secretions, and other biological samples containing proteins, bacteria, viral particles and/or cells (eukaryotic, prokaryotic, or particles thereof) among others. In certain aspects, the aqueous fluids can also contain surfactants or other agents to facilitate desired interactions and/or compatibility with immiscible fluids and/or other materials or interfaces they may come in contact with. In certain aspects, the aqueous solutions loaded on the devices can have cells expressing a malignant phenotype, fetal cells, circulating endothelial cells, tumor cells, cells infected with a virus, cells transfected with a gene of interest, or T-cells or B-cells present in the peripheral blood of subjects afflicted with autoimmune or autoreactive disorders, or other subtypes of immune cells, or rare cells or biological particles (e.g., exosomes, mitochondria) that circulate in peripheral blood or in the lymphatic system or spinal fluids or other body fluids. The cells or biological particles can, in some circumstances, be rare in a sample and the discretization can be used, for example, to spatially isolate the cells, thereby allowing for detection of the rare cells or biological particles.

In some aspects, the second fluid, which would become the continuous phase, will be a fluid that is immiscible with the first fluid. The second fluid is sometimes referred to as an oil, but does not need to be an oil. Potential fluids that can serve as the second fluid include but are not limited to, fluorocarbon based oils, silicon compound based oils, hydrocarbon based oils such as mineral oil and hexadecane, vegetable based oils, ionic liquids, an aqueous phase immiscible with the first aqueous phase, or that forms a physical barrier with the first phase, supercritical fluids, air or other gas phases.

In certain aspects of the present disclosure, the polydisperse droplets can comprise a fluid interface modification. Fluid interface modification elements include interface stabilizing or modifying molecules such as, but not limited to, surfactants, lipids, phospholipids, glycolipids, proteins, peptides, nanoparticles, polymers, precipitants, microparticles, a molecule with a hydrophobic portion and a hydrophilic portion, or other components. In some aspects, one or more fluid interface modification elements can be present in a fluid that will be comprised in a disperse droplet phase fluid. In other aspects, one or more fluid interface modification elements can be present in a fluid that will be comprised in a continuous carrier phase fluid. In still other aspects one or more fluid interface modification elements can be present in both disperse droplet phase fluids and continuous carrier phase fluids. The fluid interface modification elements present in a fluid that will be comprised in one phase of the emulsion can be the same or different from the fluid interface modification elements present in a fluid that will be comprised in another phase of the emulsion.

In some aspects, of the present disclosure, the fluid interface modification element can be used to prevent coalescence of neighboring emulsion droplets, leading to long-term emulsion stability. In some aspects, fluid interface modification elements can have some other or additional important role, such as providing a biocompatible surface within droplets, which may or may not also contribute to emulsion stability. In some aspects, the components can play a role in controlling transport of components between the fluids or between droplets. Some non-limiting examples of fluid interface modification elements include without limitation ABIL WE 09, ABIL EM90, TEGOSOFT DEC, bovine serum albumin (BSA), sorbitans (e.g., Span 80), polysorbates (e.g., PEG-ylated sorbitan such as TWEEN 20 and TWEEN 80), sodium dodecylsulfate (SDS), 1H,1H,2H,2H-perfluorooctanol (PFO), Triton-X 100, monolein, oleic acid, phospholipids, and Pico-Surf, as well as various fluorinated surfactants, among others.

In some aspects, the emulsion system will consist of a dispersed aqueous phase, containing the sample of interest, surrounded by a continuous oil phase. Other aspects can be variations or modifications of this system, or they can be emulsions of completely different composition or construction. Alternative emulsion systems include multiple emulsions such as water in oil in water (water/oil/water, or w/o/w) emulsions, or oil in water in oil (oil/water/oil, or o/w/o) emulsions. These multiple emulsion systems would then have inner, middle and outer phases. In some aspects, the inner and outer phases can have the same composition. In other aspects, the inner and outer phases can be similar—for example, both aqueous, or both the same oil—but with different sub-components. In other aspects, all three emulsion phases can have different, and sometimes very different, compositions.

In certain aspects, the emulsion system can comprise two immiscible fluids that are both aqueous or both non-aqueous. In further aspects, both emulsion fluids can be oil based where the oils are immiscible with each other. For example, one of the oils can be a hydrocarbon-based oil and the other oil can be a fluorocarbon based oil. In other emulsion systems, both fluids can be primarily aqueous but still be immiscible with each other. In some aspects, this occurs when the aqueous solutions contain components that phase separate from each other. Some examples of solutes that can be used include, but are not limited to, systems containing dextran, ficoll, methylcellulose, polyethylene glycol (PEG) of varying length, copolymers of polyethylene glycol and polypropylene glycol, polyvinyl alcohol (PVA), polyvinyl pyrrolidone (PVP), Reppal PES, $K_3PO_4$, sodium citrate, sodium sulfate, $Na_2HPO_4$, and $K_3PO_4$.

In addition to aqueous solutions and non-aqueous fluids, surfactants can also be included to, e.g., improve stability of the droplets and/or to facilitate droplet formation. Suitable surfactants can include, but are not limited to, non-ionic surfactants, ionic surfactants, silicone-based surfactants, fluorinated surfactants or a combination thereof. Non-ionic surfactants can include, for example, sorbitan monostearate (Span 60), octylphenoxyethoxyethanol (Triton X-100), polyoxyethylenesorbitan monooleate (Tween 80) and sorbitan monooleate (Span 80). Silicone-based surfactants can include, for example, ABIL WE 09 surfactant. Other types of surfactants generally well known in the art can similarly be used. In some aspects, the surfactant can be present at a variety of concentrations or ranges of concentrations, such as approximately 0.01%, 0.1%, 0.25%, 0.5%, 1%, 5%, or 10% by weight.

In certain aspects, the polydisperse droplets of the present disclosure have a continuous volume distribution. As provided herein, the term "continuous volume distribution" is intended to describe a distribution of volumes that vary continuously, rather than by pre-defined discrete steps, across the volume distribution. For example, chip-based platforms can include well or droplet volumes that cover a volume distribution defined by pre-defined, discrete steps fabricated as part of the chip. That is, a chip can be made to have volumes present at 100 nL, 10 nL, and 1 nL, with no other volumes present in between those discrete steps. In contrast, a continuous volume distribution in not pre-defined (i.e., the volume distribution is undefined prior to producing or forming droplet volumes). The continuous volume distributions can, for example, be produced via emulsification, as described further herein. In emulsions, the volumes (e.g., droplet volumes) have a discrete volume but the droplet volumes in the distribution are undefined prior to producing the droplets (i.e., not pre-defined by fabrication techniques) and the volumes are randomly distributed along the continuous volume distribution. According to the present disclosure, an emulsification system can be produced by physical agitation, such as for example vortexing or shaking the sample. An upper and lower boundary for droplet volumes can be modified by the forces imparted on the emulsion (e.g., by the speed of vortexing or the intensity of shaking). However, the droplet volumes generated by such techniques continuously vary along the volume distribution produced.

According to various aspects of the present disclosure, polydisperse droplets are formed through emulsification of two or more immiscible fluids. According to these aspects, at least some of the polydisperse droplets contain the sample, which is subsequently amplified and analyzed by the presently described methods. As used herein, the term "polydisperse" refers to plurality of droplets in a droplet system having a continuous volume distribution. The minimum, maximum, mean, and median droplet diameters, and their respective standard deviations, for a given polydisperse droplet system depend on the physical properties of the emulsion (e.g., chemical components and temperature) and the manner in which the polydisperse droplet were formed (e.g., the type and duration of the physical agitation that gave rise to the polydisperse droplet system). The distribution of droplets and their respective probabilities can be tuned by adjusting these parameters for a given system.

In some aspects, continuous volume distributions can also be characterized such that for any set (or plurality) of droplet volumes, its distribution function can be denoted $f(x)$, where $f(x)dx$ is the probability that a given droplet in the set will have a volume between $x$ and $x+dx$. ($dx$ is an infinitesimally small number.) In certain aspects, a continuous distribution is one where the volumes of the droplets in the droplet set are (1) not pre-specified and (2) that for some range $x\_lower<x<x\_upper$, $f(x)$ is always greater than zero ($x\_lower$ cannot be equal to $x\_upper$, and nothing more needs to be known about $f(x)$). Thus, the present disclosure can in some aspects, include using a droplet set drawn from a continuous distribution, measuring the volume of each droplet in the set and using the measured droplet volumes in analysis.

Figure 8A:
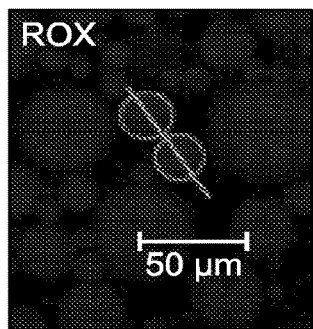
FIGS. 8A and 8B show fluorescence images of a polydisperse droplet emulsion acquired with a scanning confocal microscope for red fluorescence (FIG. 8A) and green fluorescence (FIG. 8B) detection systems. Circles in FIGS. 8A and 8B indicate identified droplets. Graphs on the right of FIGS. 8A and 8B depict fluorescence intensities along the straight lines depicted in the images on the left.
Figure 8A:
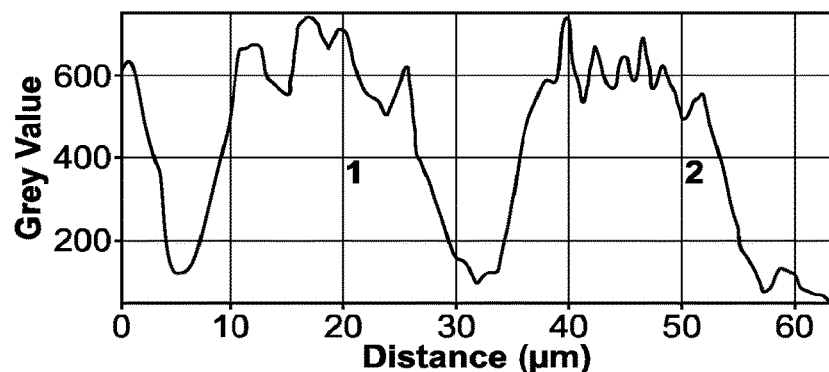
Figure 8B:
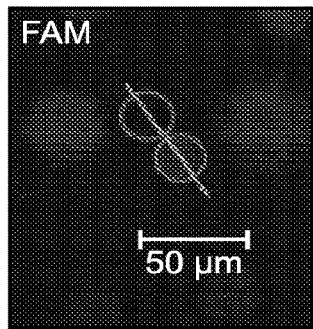
Figure 8B:
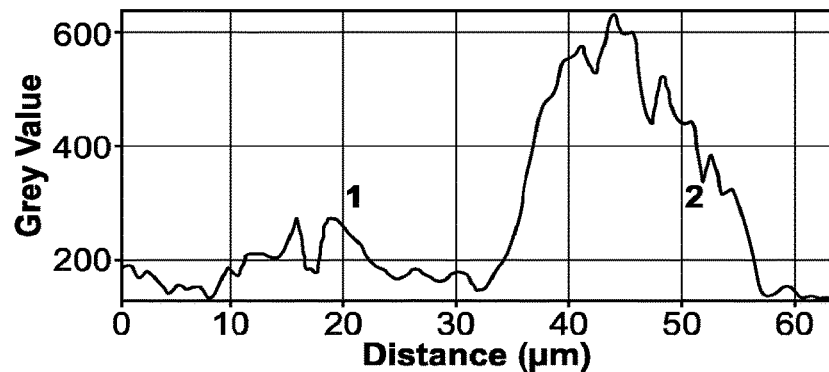
Figure 8C:
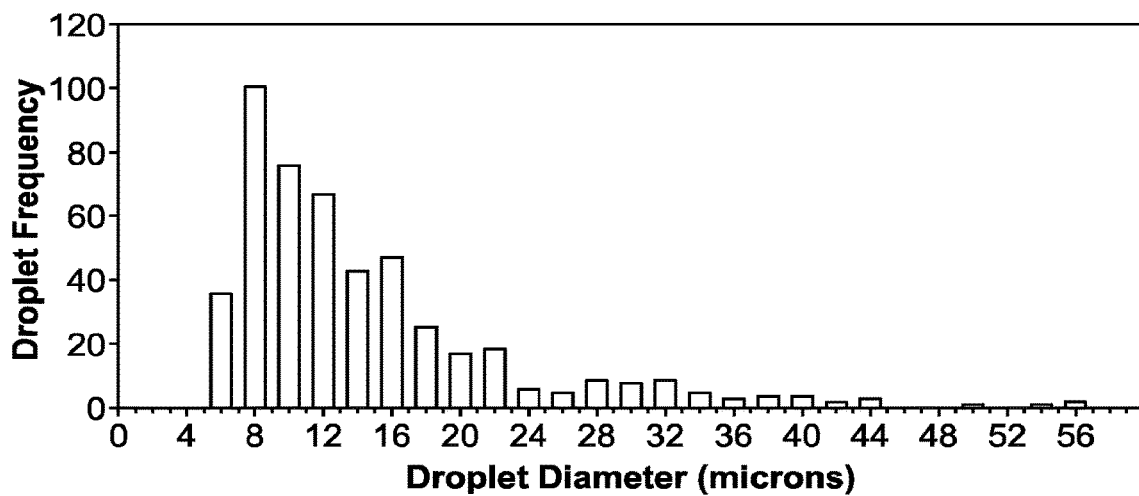
FIG. 8C shows the distribution of droplet diameters of 489 droplets measured after emulsification using the ROX fluorescence signal.
Figure 10:
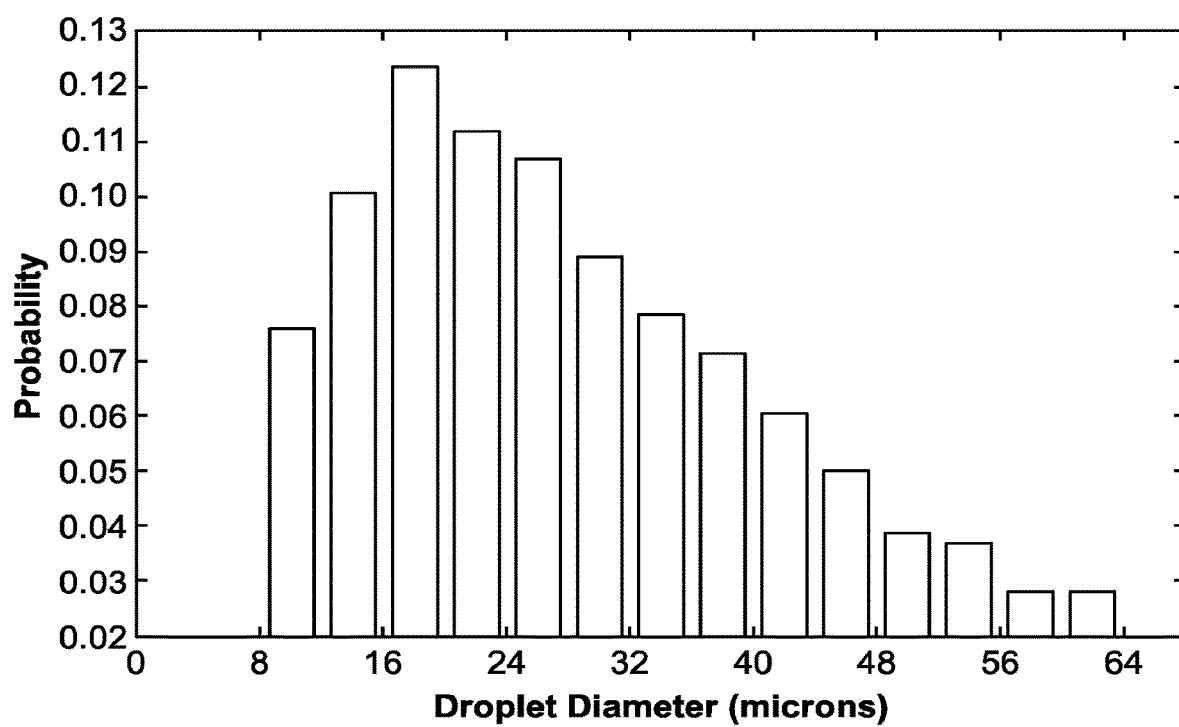
FIG. 10 shows a computer-generated clipped lognormal distribution of droplet diameters used in computer simulations to validate methods for performing digital assays. The distribution is an idealized approximation of the experimental distribution shown in FIG. 8C.

FIG. 8C shows an experimentally measured distribution of droplet diameters and their respective probabilities generated according to the presently described methods and systems. The distribution of experimentally determined droplet diameters and probabilities are consistent with theoretically determined values, as depicted in FIG. 10, and both figures depict a continuous volume distribution for droplets.

As described herein, the volumes can be produced having a variety of volume distributions, which can be analyzed using a variety of different methods. In some aspects, a sample can contain a molecule or molecules of interest that can be analyzed. Discrete volumes of the sample can be generated for analysis via digital measurements. For example, the methods herein can include producing a plurality of droplets having a volume distribution. In some aspects, the plurality of droplets of the sample can be produced in an emulsion that includes combining immiscible fluids, as further described herein. In one example, a sample can include an aqueous solution that includes a molecule of interest (e.g., a nucleic acid molecule). The sample can be mixed with an oil to form droplets of the sample suspended in the oil. Depending on the method used, the volumes of the plurality of droplets in the emulsion can be randomly distributed along a continuous volume distribution. Furthermore, the ranges of volumes can be controlled by the method used to form the emulsions. For example, intensity of vortexing, shaking, sonicating, and/or extrusion can be controlled to produce a desired volume distribution, or by varying the composition of the surfactant and/or oil.

As will be appreciated by one of ordinary skill in the art, the ranges for and volumes within a volume distribution will depend on a variety of factors for a given analysis. In some aspects, the volume distributions of the plurality of droplets can include a volume range from about 100 nanoliters (nL)

to about 1 femtoliter (fL), from about 10 nL to about 10 fL, from about 1 nL to about 100 fL, from about 100 nL to about 1 picoliter (pL), from about 10 nL to about 10 pL, from about 1 nL to about 1 pL, from about 500 pL to about 50 fL, from about 100 pL to about 100 fL. Depending on the selected factors for producing droplets, it is routine to define the upper and lower boundaries of a volume distribution by, e.g., changing the intensity of mixing a sample and oil with a surfactant. There can be ranges of volumes in the volume distributions. For example, volumes in the distributions can range by more than a factor of 2, by more than a factor of 10, by more than a factor of 100, by more than a factor of 1000, by more than a factor of 10000, by more than a factor of 100000, by more than a factor of 1000000, by more than a factor of about 2, by more than a factor of about 10, by more than a factor of about 100, by more than a factor of about 1000, by more than a factor of about 10000, by more than a factor of about 100000 or by more than a factor of 1000000. By ranging by a factor of 2, the lower boundary of the volume distribution can be, e.g., 10 nL with an upper boundary of 20 nL. Similarly, by ranging by a factor 10, the lower boundary of the volume distribution can be, e.g., 10 nL with an upper boundary of 100 nL.

In some aspects, of the present disclosure, the polydisperse droplets have a distribution of droplet diameters with a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the median droplet diameter.

In some aspects, of the present disclosure, the polydisperse droplets have a distribution of droplet diameters with a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the mean droplet diameter.

In some aspects, of the present disclosure, the volumes can be created using valves, wells, or droplets. Here, droplets of different volumes (diameters) can be generated using a wide range of methods. In one method, droplets of a defined volume are generated using microfluidics (e.g., with T-channel or flow focusing as well known in the art); by varying the shear rate or channel dimension, droplets of different sizes can be formed. In another method, the droplets of different volumes are generated by emulsification with the aid of different surfactants; here the droplets of different volumes are stabilized and are controlled with the use of different surfactants. With either method, amplification of analyte (e.g., digital PCR) can be carried out simultaneously in all droplets of different volumes (sizes). In certain aspects, the droplets can then be flowed in a single-file format through a flow cytometer or other similar device where the size of the droplet can be determined and the fluorescence from the droplet can be interrogated. When using flow cytometry or other flow-through methods, the presence of amplification product in each droplet is determined based on fluorescence and the size (volume) of each droplet is determined based on the scattering signal from the droplet. Alternatively, the size can be determined by taking an image as the droplet passes through the apparatus in a manner similar to image-based flow cytometry. In this way, by noting both the size of each droplet and the presence or absence of amplification product in each droplet of a given size, it is possible to back-calculate the original concentration of the analyte present in the sample after interrogating a sufficient number of droplets of different sizes. Because the droplets are of different sizes, for a given dynamic range, the analysis is much faster than if the droplets are all of a similar size for reasons discussed previously.

In certain aspects, the present methods and systems can be used to analyze samples in digitized volumes. The term "digitized volumes" refers to the volumes produced after obtaining an initial sample and separating it into physically distinct smaller volumes in preparation for an assay.

According to certain aspects of the present disclosure, droplets can be formed and assayed in a chip. According to further aspects, amplification and digital measurements can take place in a digitization chip.

In one aspect, the present disclosure provides a method for creating concentration gradients that are integrated with digital measurement and readout. For example, one can integrate microfluidic gradient generation with a sample digitization chip. For increasing the dynamic range, a logarithmic or exponential concentration gradient is preferred, but a number of methods are now available for forming various types and shapes of concentration gradients on chip, including nonlinear gradients such as power, exponential, error, Gaussian, and cubic root functions.

According to certain aspects of the present disclosure, a concentration gradient in a microfluidic device can be used in which there are only two inlet reservoirs or channels, but more would also be suitable for use of the disclosure. According to this aspect, one inlet is used for the sample and one for buffer (or PCR reagent in the case of digital PCR). As the two solutions flow through the network, the sample solution becomes diluted by the buffer (water or PCR reagent) solution in a pre-defined fashion such that at each of the outlet channels, a different concentration of the sample is present. Linear, polynomial, and logarithmic gradients spanning six orders of magnitude have all been generated using variations of this design.

In another aspect, a logarithmic or exponential gradient spanning six orders of magnitude in concentration is used. The sample and PCR solution is pipetted into the two inlet reservoirs, after which they will pass over the array of wells. Once the wells have been filled with the concentration gradient, light mineral oil or some other immiscible fluid is flowed over the wells to create individual digitized volumes within the wells. The wells in this example are of the same volume. In another aspect of the disclosure, wells of varying volumes can be used.

In another aspect, the sample and PCR solution is pipetted into the two inlet reservoirs, after which they will pass over an array of hydrophilic and hydrophobic patches. As the sample flows over the hydrophilic patches, they cause the formation of wetted droplets of different size sample volumes. Alternatively, the sample can be digitized.

In another aspect of the disclosure, the gradients are used in conjunction with digitized volumes created using valves, wells, or droplets. In the aspect with droplets, the droplets can be formed in a continuous-flow fashion either in the T-channel geometry or in the flow focusing geometry, both of which are well known in the art.

To digitize the sample that had been diluted, a digitization scheme can be used. Here, the sample solution containing different concentrations of target molecule are flown over the topographically patterned surface to form digitized and discrete volumes for subsequent digital measurements and readout. Alternatively, it is possible to digitize the sample using a patterned surface.

In another aspect, the sample can be digitized using microfluidic channels and immiscible fluid phases. In this aspect, the sample phase is introduced into the channel, followed by an immiscible phase which forms discrete sample volumes that are defined by the geometric dimensions of the side cavities (D. E. Cohen, T. Schneider, M. Wang, D. T. Chiu, *Anal. Chem.* 82, 5707-5717).

According to one exemplary aspect, the present disclosure provides arrays of digitized volumes of different sizes, where patterned surfaces are used to create arrays of volumes of different sizes. According to this aspect, seven sets of arrays are created, where each array contains 900 digitized volumes (30×30). The array is formed by creating hydrophilic circular patches in a background of a hydrophobic surface. As a result, when the surface is exposed to aqueous solution and oil, the hydrophilic patches will be covered by an aqueous drop surrounded by oil. The droplet can be hemi-spherical, but the shape can change (either more pancaked or more rounded) depending on the exact surfaces we use and the oil and aqueous solution used. In one aspect, a heavy oil is used, and the drop is more pancaked because the oil will push on the drop.

The circles that define each set of the 900 hydrophilic patches have different sizes, ranging from 1 μm in diameter to 5 μm to 10 μm to 50 μm to 100 μm to 500 μm and finally to 1 mm in diameter. Because the volume of the drop scales roughly as cubic to the diameter of the drop, increasing the diameter of the patch by ten times increases the volume by about 1,000 times. As a result, using digitized volumes of varying sizes is more efficient in terms of space and readout than simply using more digitized volumes of the same size. In one aspect, 900 digitized volumes for each set of the array is used because this number is suitable for arriving at a statistically robust digital readout. However, depending on the particular application and the needed robustness of the readout, either more digitized volumes within each set of array or less digitized volumes can be designed. According to this aspect, a large array of digitized volumes can be produced with varying sizes due to the ease of surface patterning hydrophilic patches of different sizes. This aspect can be useful for applications such as digital PCR where a wide dynamic range is often desired, it is highly beneficial to perform PCR in drops that are created using patterned surfaces.

In certain aspects, a dispersed droplet system can undergo a change from a liquid to a solid phase for at least a portion of the dispersed droplet system. In some aspects, liquids of the disperse droplet system can be converted to a solid through a gelation process. For example, a solution of agarose can solidify as the temperature falls below its melting temperature. In further aspects, a liquid-to-solid conversion can occur through the formation of calcium alginate from soluble precursors, by photopolymerization of solution components, the use of cross-linking agents that induce polymerization. In some aspects, entire droplets are solidified solidify, while in other aspects, only a layer at the interface solidifies.

In some aspects, emulsion systems of the present disclosure can be configured such that the degree of diffusion between the droplet and the surrounding media can be enhanced or minimized, depending upon the application of interest. In certain aspects, the polydisperse droplet emulsion system can be designed to enhance diffusion of reagents between the droplet and the surrounding phase. In certain aspects, the polydisperse droplet emulsion system can be designed to reduce or eliminate diffusion of reagents between the droplet and the surrounding phase. For example, agarose droplets formed at temperatures above the agarose melting temperature solidify when cooled to room temperature and, depending on the concentration of agarose in the solution, diffusion within or across the drop boundary can occur. In certain aspects, the composition of the droplet and surrounding media can be tuned to maximize diffusion after droplet encapsulation. The properties of droplets can also be tuned to prevent unwanted diffusion, e.g., of a target molecule. In certain aspects, target molecules can be cross-linked or anchored in place. For example, key molecules such as primers can be anchored to the matrix. Anchoring target molecules in place can enable the use of emulsions in non-oil based platforms, which can have the advantage of better facilitating downstream processing or sample recovery, among other advantages.

In some aspects, a physical barrier can be created between the phases in a disperse droplet system. In certain aspects, a physical barrier surrounding the droplet can be a polymerized solid shell, a lipid bilayer, a precipitated interface, or an aggregation of a material such as proteins, nanoparticles, vesicles, precipitants, microscopic particles or other materials at the interface.

Other modifications to the emulsion system can be made to alter certain properties that can benefit the manipulation, processing or analysis of the emulsion. Depending on the method of analysis, different physical and optical properties of the emulsion system can play a very important role. These include, but are not limited to, the size distribution of the emulsion droplets, the relative density of the fluids, the viscosity of the fluids, the refractive index of the fluids and the overall and local density of the droplets within the continuous fluid.

Refractive index matching can be beneficial for improving the imaging depth for optical analysis (e.g., reducing distortions of droplet boundaries). The refractive index of the aqueous phase is typically close to the refractive index of waters, i.e., approximately n=1.33. The refractive index of the aqueous phase is typically lower than that of hydrocarbon-based oils, but slightly higher than that of fluorinated oils. In one aspect of the present disclosure, refractive index matching can be achieved by adding high refractive index (i.e., n>1.45) components such as, but not limited to, glycerol, sucrose, Cargille optical liquids, ethylene glycol, propylene glycol, $CS_2$, methyl salicylate, dimethyl sulfoxide (DMSO), among others to the aqueous phase of the emulsion to enable the refractive index of an aqueous phase to more closely match that of the oil. In other aspects, refractive index matching can be achieved by adjusting the refractive index of the non-aqueous phase typically consisting of a mixture of a component with a higher refractive index and a component with a lower refractive index than the aqueous phase. Any suitable additive can be used to raise the refractive index of a low-refractive index fluid, such as, but not limited to fluorocarbon-based oils (e.g., perfluorodecalin; Fluorinert oils such as e.g., FC-40, FC-70; Krytox oils, among others, with high refractive index (i.e., n=1.36-1.4); fluorocarbon solvents, such as but not limited to octafluorotoluene, hexafluorobenzene, petafluorobenzene, 1,2,4,5-tetrafluorobenzene decafluoro-p-xylol, among others. Table 1 below provides a non-inclusive list of additives that can be used to adjust the refractive index of the non-aqueous phase, thereby causing it to more closely match that of the aqueous phase (i.e., water, n=1.33):

TABLE 1

Summary of physical properties of a selection of fluorocarbon oils and solvents listed in order of ascending refractive index. Water is included for reference.

| Chemical Name | Refractive Index, n | Density (g/cm$^3$) | Boiling Point (° C.) |
| --- | --- | --- | --- |
| Fluorinert FC-40 oil | 1.29 | 1.855 | 165 |
| Fluorinert FC-70 oil | 1.303 | 1.94 | 215 |
| Perfluorodecalin | 1.3145 | 1.908 | 142 |
| Water | 1.333 | 1.00 | 100 |
| decafluoro-p-xylol | 1.3606 | 1.651 | 121-122 |
| octafluorotoluene | 1.368 | 1.666 | 104 |
| hexafluorobenzene | 1.377 | 1.612 | 80-82 |
| pentafluorobenzene | 1.391 | 1.514 | 85 |
| 1,2,4,5-tetrafluorobenzene | 1.407 | 1.344 | 90 |
| 1,3,5-trifluorobenzene | 1.414 | 1.277 | 75-76 |
| 1,4-difluorobenzene | 1.441 | 1.11 | 88-89 |
| fluorobenzene | 1.465 | 1.024 | 85 |
| 1-ethynyl-4-fluorobenzene | 1.516 | 1.048 | 55-56 |

Proper spacing of droplets is important to maximize the number of droplets that can be analyzed without information from one droplet interfering with another droplet. In some aspects, the space between droplets can be increased by altering the density of the oil system. For example, partly fluorinated hydrocarbon compounds can be used to lower the density of a fluorocarbon oil. In another aspect the density of an aqueous solution can be altered by adding CsCl or some other suitable density increasing component. For example a solution containing CsCl at 56% by weight would have a density near 1.7 g/mL, and at 65% would have a density of approximately 1.9 g/mL, with these closely matching the density of many fluorocarbons. The viscosity of the oil can also be altered so that the droplets move more slowly and/or to increase the wetting layer between droplets. In another aspect, the second fluid can experience a phase transition to a more solid nature so that the discrete phase is trapped at certain positions. In another aspect double emulsions (e.g., w/o/w) can be used to pack droplets close together while also preventing direct contact/overlap.

In some aspects, the distribution of droplet diameters has a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the median droplet diameter. In some aspects, the distribution of droplet diameters has a standard deviation greater than about 1000%, greater than about 500%, greater than about 100%, greater than about 50%, greater than about 30%, greater than about 20%, greater than about 15%, greater than about 10%, greater than about 9%, greater than about 8%, greater than about 7%, greater than about 6%, or greater than about 5% of the median droplet diameter.

In other aspects, the distribution of droplet diameters has a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the mean droplet diameter. In some aspects, the distribution of droplet diameters has a standard deviation greater than about 1000%, greater than about 500%, greater than about 100%, greater than about 50%, greater than about 30%, greater than about 20%, greater than about 15%, greater than about 10%, greater than about 9%, greater than about 8%, greater than about 7%, greater than about 6%, or greater than about 5% of the mean droplet diameter.

In further aspects, the volumes in the polydisperse droplets vary by more than a factor of 2, by more than a factor of 10, by more than a factor of 100, by more than a factor of 1000, by more than a factor of 10000, by more than a factor of 100000, by more than a factor of 1000000, by more than a factor of 2, by more than a factor of 10, by more than a factor of 100. In yet further aspects, the volumes in the polydisperse droplets vary by more than a factor of about 2, more than a factor of about 10, or by more than a factor of about 100, by more than a factor of about 1000, by more than a factor of about 10000, by more than a factor of about 100000 or by more than a factor of 1000000.

In some aspects, the polydisperse droplets have a volume distribution of from 100 nanoliters (nL) to 1 femtoliters (fL), from 10 nL to 10 fL, from 1 nL to 100 fL, from 100 nL to 1 pL, from 10 nL to 10 pL, or from 1 nL to 1 pL, from 500 pL to 50 fL, from 100 pL to 100 fL. In further aspects, the polydisperse droplets have a volume distribution of from about 100 nanoliters (nL) to about 1 femtoliters (fL), from about 10 nL to about 10 fL, from about 1 nL to about 100 fL, from about 100 nL to about 1 pL, from about 10 nL to about 10 pL, or from about 1 nL to about 1 pL, from about 500 pL to about 50 fL, from about 100 pL to about 100 fL In certain aspects, the mean volume of the polydisperse droplets changes by less than 50%, less than 40%, less than 35%, less than 30%, less than 25%, less than 20%, less than 15%, less than 10%, less than 5%, less than 4%, less than 3%, less than 2%, or less than 1% during amplifying the sample. In other aspects, the median volume of the polydisperse droplets changes by less than about 50%, less than about 40%, less than about 35%, less than about 30%, less than about 25%, less than about 20%, less than about 15%, less than about 10%, less than about 5%, less than about 4%, less than about 3%, less than about 2%, or less than about 1% during amplifying the sample.

In some aspects, the amplifying the sample comprises a first amplification cycle, and wherein fewer than 50%, fewer than 45%, fewer than 40%, fewer than 35%, fewer than 30%, fewer than 25%, fewer than 20%, fewer than 19%, fewer than 18%, fewer than 17%, fewer than 16%, fewer than 15%, fewer than 14%, fewer than 13%, fewer than 12%, fewer than 11%, fewer than 10%, fewer than 9%, fewer than 8%, fewer than 7%, fewer than 6%, fewer than 5%, fewer than 4%, fewer than 3%, fewer than 2%, or fewer than 1% of the polydisperse droplets fuse after the first amplification cycle. In further aspects, the amplifying the sample comprises a first amplification cycle, and wherein fewer than about 50%, fewer than about 45%, fewer than about 40%, fewer than about 35%, fewer than about 30%, fewer than about 25%, fewer than about 20%, fewer than about 19%, fewer than about 18%, fewer than about 17%, fewer than about 16%, fewer than about 15%, fewer than about 14%, fewer than about 13%, fewer than about 12%, fewer than about 11%, fewer than about 10%, fewer than about 9%, fewer than about 8%, fewer than about 7%, fewer than about 6%, fewer than about 5%, fewer than about 4%, fewer than about 3%, fewer than about 2%, or fewer than about 1% of the polydisperse droplets fuse after the first amplification cycle.

In some aspects, the refractive index of the first fluid differs from the refractive index of the second fluid by less than 200%, less than 100%, less than 60%, less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%. In further aspects, the refractive index of the first fluid differs from the refractive index of the second fluid by less than about 200%, less than about 100%, less than about 60%, less than about 50%, less than about 45%, less than about 40%, less than about 35%, less than about 30%, less than about 25%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1%.

In some aspects, such as in double emulsions, the refractive index of the first fluid differs from the refractive index of the bulk medium by less than 200%, less than 100%, less than 60%, less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

In some aspects, the polydisperse droplets comprise a plurality of emulsions. In certain aspects, the plurality of emulsions is prepared by combining three or more immiscible fluids.

Devices and Methods for Performing Digital Measurements

Another aspect of the disclosure comprises a device for carrying out the methods of the disclosure. According to this aspect, the present disclosure provides a means for producing an plurality of polydisperse droplets having a volume distribution, a means for measuring the volume of a given droplet in the plurality of polydisperse droplets, a means for determining the presence or absence of sample in the droplet, and the concentration of sample in the plurality of polydisperse droplets. The present methods enable the performance of digital measurements over a large dynamic range and methods and systems for increasing the dynamic range. Specifically, the device increases the dynamic range of digital measurements of a sample by, inter alia, creating sample volumes of different sizes.

In various aspects, the present disclosure provides methods for performing a digital assay, comprising: producing a plurality of polydisperse droplets, wherein at least some of the droplets comprise a sample; amplifying the sample; labeling the sample with a detectable agent; obtaining an image stack for a droplet; determining from the image stack the volume of the droplet; determining from the image stack the presence or absence of the detectable agent in the droplet; and determining the concentration of the sample in the plurality of droplets based on the presence or absence of the detectable agent in the plurality of droplets.

In some aspects, obtaining the image stack comprises optical imaging. In some aspects, detecting the detectable agent comprises optical imaging.

In further aspects, the optical imaging is performed by confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epifluorescence microscopy, bright field imaging, dark field imaging, oblique illumination, or a combination thereof.

In certain aspects, the image stack comprises a plurality of images taken from separate depths of focus through a single droplet.

In further aspects, the image stack comprises 2, 3, 4, 5, 6, 7, 8, 9, 10, 15, 20, 25, 30, 35, 40, 45, 50, 55, 60, 65, 70, 75, 80, 85, 90, 95 or 100 images taken from separate depths of focus for a droplet. In other aspects, the image stack comprises greater than 2, greater than 3, greater than 4, greater than 5, greater than 6, greater than 7, greater than 8, greater than 9, greater than 10, greater than 15, greater than 20, greater than 25, greater than 30, greater than 35, greater than 40, greater than 45, greater than 50, greater than 55, greater than 60, greater than 65, greater than 70, greater than 75, greater than 80, greater than 85, greater than 90, greater than 95 or greater than 100 images taken from separate depths of focus for a droplet. In still other aspects, the image stack comprises greater than about 2, greater than about 3, greater than about 4, greater than about 5, greater than about 6, greater than about 7, greater than about 8, greater than about 9, greater than about 10, greater than about 15, greater than about 20, greater than about 25, greater than about 30, greater than about 35, greater than about 40, greater than about 45, greater than about 50, greater than about 55, greater than about 60, greater than about 65, greater than about 70, greater than about 75, greater than about 80, greater than about 85, greater than about 90, greater than about 95 or greater than about 100 images taken from separate depths of focus for a droplet.

In further aspects, the image stack comprises from 100 to 50, 100 to 75, 100 to 25, 100 to 20, 100 to 10, 100 to 5, 50 to 20, 50 to 10, 50 to 5, 20 to 10, 20 to 5, 10 to 5, 10 to 2, about 100 to about 50, about 100 to about 75, about 100 to about 25, about 100 to about 20, about 100 to about 10, about 100 to about 5, about 50 to about 20, about 50 to about 10, about 50 to about 5, about 20 to about 10, about 20 to about 5, about 10 to about 5, or about 10 to about 2 images taken from separate depths of focus for a droplet or object planes of the imaging device.

In some aspects, the present methods are performed concurrently on a plurality of droplets. In further aspects, the plurality of polydisperse droplets comprises an array of polydisperse droplets. In yet further aspects, the array of polydisperse droplets is disposed in a multi-well plate.

In some aspects, the volume of the droplets is determined from the image stack by the Line Scan Method, Simple Boundary Method, Reverse Watershed Method, Circle Detection Method, Combined Reverse Watershed and Circle Detection Method, or a combination thereof.

In some aspects, the concentration of the detectable agent is determined over a dynamic range of at least three orders of magnitude or over a dynamic range of at least six orders of magnitude.

In some aspects, the plurality of polydisperse droplets comprises a first fluid and a second fluid, wherein the first fluid is immiscible in the second fluid. In certain aspects, the emulsion of polydisperse droplets is formed by agitating a solution comprising a first fluid and a second fluid, wherein the first fluid is immiscible in the second fluid. In further aspects, the agitating comprises vortexing.

In various aspects, the present disclosure provides methods comprising: forming an emulsion of polydisperse droplets by agitating a solution comprising a first fluid and a second fluid, wherein the first fluid is immiscible in the second fluid; and agitating the emulsion in a third fluid, wherein the third fluid is immiscible in the second fluid, thereby forming a double emulsion.

In some aspects, the present disclosure provides methods that comprise fluid agitation, wherein the agitating can be shaking, vortexing, sonicating, mixing with magnets, extrusion, via flow focusing or a combination thereof. In further aspects, the agitating is sufficient to form an emulsion. In further aspects, extrusion comprises pipetting the fluid, wherein the pipetting is sufficient to produce an emulsion. In certain aspects, the agitating occurs in a microfluidic device.

In various aspects, the first fluid comprises water, the second fluid comprises oil and the third fluid comprises water.

In various aspects, the polydisperse droplets comprise a plurality of emulsions. In further aspects, the plurality of emulsions is prepared by combining three or more immiscible fluids.

In some aspects the first fluid is aqueous. In certain aspects, first fluid comprises a sample. In further aspects, the second fluid is an oil. In certain aspects, the second fluid is an oil, and the second fluid is immiscible with the first fluid and the third fluid. In some aspects, the first fluid is different from the third fluid. In certain aspects, the third fluid is an oil, and wherein the third fluid is immiscible with the first fluid and the second fluid.

In some aspects, the emulsion comprises an aqueous phase and a non-aqueous phase. In further aspects, the first fluid comprises water and the second fluid comprises oil.

In certain aspects, the plurality of polydisperse droplets further comprises a fluid interface modification element. In further aspects, the fluid interface modification element is a surfactant. In yet further aspects, the fluid interface modification element is selected from a lipid, phospholipid, glycolipid, protein, peptide, nanoparticle, polymer, precipitant, microparticle, a molecule with a hydrophobic portion and a hydrophilic portion, or a combination thereof.

In some aspects, the present methods further comprise converting one or more of the immiscible fluids to a gel or solid. In certain aspects, the immiscible fluid is converted to a gel or solid before amplifying the sample, during amplifying the sample, or after amplifying the sample.

In various aspects, the detectable agent used in the present methods is fluorescent or luminescent. In certain aspects, the detectable agent is fluorescein, a derivative of fluorescein, rhodamine, a derivative of rhodamine, or a semiconducting polymer.

As used herein, the term "dynamic range" is defined as the ratio between the largest and smallest possible values of a changeable quantity.

The term "digital assay" means an assay in which measurements are made based on a counting of smaller measurements, wherein each smaller measurement is binary, having a value that is one of exactly two possible values that can be assigned to it. The digital assays described herein comprise measurements of a sample present in a fluid based on a counting of binary measurements obtained from individual volumes of the fluid.

Reactions (e.g., amplification) can be carried out in volumes with different sizes, before or during analysis of the volumes to determine in which volumes have undergone reaction (e.g., have amplified product). In certain examples, the volumes (e.g., droplets) can be sized and the number of occupied droplets (e.g., droplets containing a detectable agent) counted. All or just some of the droplets can be analyzed. Analysis can, for example, be achieved by flowing the droplets in a single file through a flow cytometer or similar device, where the size of the droplet can be determined and the presence of amplification can be detected. The size of the droplet can, for example, determined based on the scattering signal from the droplet and the presence of amplification can be indicated by a fluorescence signal from the droplet. Alternatively, the diameter of droplets can be determined by microscopy. Droplets can be extracted (before, during, or after completion of a reaction, e.g., amplification) from a sample holder and imaged in widefield with a CCD camera. The droplets, e.g., can be spread out on a surface or embedded between two glass slides and placed under a widefield microscope. By using appropriate excitation and emission filters the fluorescence within the droplet can be quantified to reveal the presence or absence of amplification. By noting both the size of the droplet and the presence or absence of amplification product in each droplet, it is possible to back-calculate the original concentration of the analyte present in the sample after interrogating a sufficient number of droplets of different sizes. Because the droplets are of different sizes, for a given dynamic range, the analysis is much faster than if the droplets are all of similar size. In some aspects, the methods herein further include using a number of droplets in a plurality and the individual volumes of the droplets in the plurality to conduct digital measurements. For example, a sample concentration of a molecule of interest can be determined using the number of droplets in the plurality, the number of droplets in the plurality with one or more molecules of interest, and by measuring the volume of some or all of the droplets in the plurality. Example methods for determining sample concentrations can be found in the Examples section.

In some aspects, the present disclosure provides methods for performing a digital assay, comprising: producing a plurality of polydisperse droplets, wherein at least some of the droplets comprise a sample; amplifying the sample; labeling the sample with a detectable agent; flowing the plurality of polydisperse droplets through a flow cytometry channel; determining the volume of a droplet as it flows through the flow cytometry channel; determining the presence or absence of the detectable agent in the droplet; and determining the concentration of the sample in the plurality of droplets based on the presence or absence of the detectable agent in a plurality of droplets.

In certain aspects, determining the concentration of the sample comprises detecting light scattered from a droplet.

The present disclosure can be used for any technique in which digital measurements provide useful information about a sample. As such, the methods, systems and devices provided herein can include a volume containing a detectable agent. In certain aspects, the volume can be a well or chamber in a microfluidic chip or a droplet (e.g., a water droplet formed in an emulsion or on the surface of a chip) that contains the detectable agent. It will be generally understood that the detectable agent can include a single detectable molecule or a plurality of detectable molecules. Other types of detectable agents can be used, e.g., beads, quantum dots, nanoparticles, and the like. Furthermore, the detectable agent can, for example, be a molecule of interest present in a sample to be analyzed (e.g., a nucleic acid molecule in blood, serum, saliva or other solutions). Alternatively, a detectable agent can be a molecule that associates with a molecule of interest (e.g., the nucleic acid molecule) in the sample, thereby allowing the molecule to be detected. In some aspects, the methods and systems of the present disclosure can be used for amplification-related techniques (e.g., digital PCR) involving digital measurements. For amplification measurements, a volume (e.g., a droplet) can include a single DNA molecule, for example, but the volume will also contain necessary components that are generally well known to be used for amplification and detection. In some aspects, the detectable agent is fluorescent and, thus, can be detected by fluorescence-based detection methods known in the art. However, other detection methods (e.g., absorbance, chemiluminescence, turbidity, and/or scattering) can be used to analyze the contents of a volume. A variety of detectable agents suitable for the present disclosure are generally well known in the art and can, for example, be found in The Molecular Probes Handbook, 11$^{th}$ Edition (2010).

In certain aspects, the detectable agent can be associated with a molecule of interest for detection. For example, the detectable agent can be associated with a nucleic acid molecule (e.g., DNA or RNA), a peptide, a protein, a lipid, or other molecule (e.g., biomolecule) present in a sample. As defined herein, "associated" in the context of the detectable agent includes interaction with the molecule via covalent and/or non-covalent interactions. For example, the detectable agent can be covalently attached to the molecule of interest. Alternatively, the detectable agent can, for example, be an intercalation agent or a Taqman probe that can be used to detect a nucleic acid molecule (e.g., a DNA and/or RNA molecule). Other detectable agents can be used, such as reference dyes that may not associate with molecules in a volume of interest. The present disclosure further includes determining a concentration of a sample. For example, the methods and systems can be used to determine (1) volumes of droplets and (2) a number of droplets that contain a detectable agent, which can be used to determine the concentration of a sample (i.e., by determining the presence or absence of a sample in a given droplet). This information can be used in a variety of ways to determine sample concentrations. For example, target molecules are present in the sample at a concentration in units of molecules/volume. The sample can be distributed into droplets of variable volumes that can be analyzed. The individual volumes of the droplets (all or just some) can be determined by methods provided herein. In addition, using detection methods described herein, droplets can be analyzed for containing a detectable agent or not. For a given sample concentration, some of the variable-volume droplets can contain a detectable agent and some may not. For higher sample concentrations, generally more droplets of a plurality will contain detectable agents and vice versa; for low sample concentrations, fewer droplets of a plurality can be occupied by a detectable agent. As further described herein, the probabilities of occupancy by a detectable agent in a particular volume distribution can be defined for a wide range of sample concentrations, which can then be compared to real data to determine the concentration of an unknown sample. Additional disclosure for determining sample concentrations can be found in EXAMPLE 8 below. The methods illustrated in EXAMPLE 8 involve making an initial estimate for the sample concentration and then calculating the number of droplets that would be predicted to contain one or more detectable agents (occupied droplets). The estimate for the sample concentration is then adjusted using a well-known numerical method until the predicted number of occupied droplets equals the actual number of occupied droplets in the plurality to within the desired degree of accuracy.

In some aspects, the methods of the present disclosure comprise measuring a volume of a droplet only if the droplet comprises a sample. In further aspects, the methods comprise excluding from measurement any droplets determined to not comprise the sample. In some aspects, sample concentrations are determined according to methods disclosed herein by identifying, sizing or enumerating only those droplets, which are determined to comprises sample. In some aspects, sample concentration is determined by measuring or knowing the total volume of the sample and by identifying, sizing and enumerating only those droplets, which are determined to comprises sample. In further aspects, the concentrations of analytes in a sample is determined by measuring or knowing the total volume of the sample and by enumerating all the positive droplets and determining the volume of each positive droplet. Advantages of this method include reducing the number of droplets scanned and thereby reducing the analysis time for determining sample concentration.

As further described herein, the present disclosure provides various aspects for digital measurements that cannot be achieved by existing methods and systems. For example, the present disclosure can provide the ability to measure sample concentration over a wide dynamic range. In some aspects, the dynamic range can be at least three orders of magnitude, at least four orders of magnitude, at least five orders of magnitude, or at least six orders of magnitude. In some aspects, the dynamic range can be between about 10 and $10^{10}$ molecules/mL, about $10^2$ and $10^7$ molecules/mL, about $10^4$ and $10^{10}$ molecules/mL, about $10^5$ and $10^9$ molecules/mL. In certain aspects, determining sample concentration within a dynamic range can be performed by detecting a detectable agent that is associated with a molecule of interest in the sample. Dynamic range can be dependent on a variety of factors, such as the range of volumes that are produced in an emulsion and/or the range of volumes that are analyzed and detected. In certain aspects, the volume distributions include continuously varying droplet volumes.

In some aspects, the present methods are performed on a chip using concentration gradients. By integrating dPCR with on-chip gradient generation, or by using digitized volumes of varying sizes, or the combination of both these methods, the disclosure effectively increases the dynamic range of our dPCR chip by one order to six orders of magnitude, which is comparable to the dynamic range offered by RT-PCR. By using a greater range of concentration gradients or arrays of digitized volumes with larger size differences, the dynamic range can be increased even further if desired. This method for carrying out quantitative PCR (qPCR) offers several key advantages over existing technologies: (1) it is more accurate; (2) it obviates the need for running the type of calibration samples that are needed for RT-PCR and thus is higher throughput; and (3) it removes the need for real-time sensitive fluorescence detection, which is responsible for the relatively higher cost (~10×) of RT-PCR versus standard PCR devices.

Another aspect of the disclosure comprises a device for carrying out the methods of the disclosure, wherein the device creates arrays of digitized and discrete volumes of different sizes. In another aspect, the device carries out the method for increasing the dynamic range of digital measurements of a sample, comprising creating a sample concentration gradient and creating sample volumes of different sizes.

In some aspects, the present disclosure provides methods for using digital measurements to determine a concentration of a sample. The methods can include producing a plurality of droplets having a volume distribution, wherein at least one of the droplets of the plurality contains contents from the sample; determining the volume of the droplets; determining the presence of absence of sample in the droplets; and using the volumes of the droplets and the number of droplets found to contain the detectable agent to determine the concentration of the sample.

In some aspects, the present disclosure includes methods to increase the dynamic range of digital measurements that are based on creating arrays of digitized and discrete volumes of varied sizes (i.e., volumes). This method is better than simply increasing the number of digitized volumes so as to increase dynamic range. This is because simply increasing the number of digitized volumes increases the area the volumes occupy as well as increase the likelihood of having defects on the chip where some digitized volumes do not form properly or have other defects. Simply increasing the number of digitized volumes also decreases throughput by increasing the time required to analyze all the digitized volumes. In certain aspects, dynamic range can be increased by creating arrays of digitized volumes of different sizes rather than simply increasing the number of digitized volumes. The arrays of digitized volumes of different sizes can be a random array (e.g., droplets of different diameters all present and distributed randomly in a container) or can be a regular array.

Sample Amplification

The present disclosure also provides methods, devices, and systems for the amplification of samples, such as e.g., nucleic acid samples. In certain aspects, sample amplification comprises PCR. In further aspects, sample amplification comprises dPCR.

In various aspects, the sample comprises a nucleotide. In various aspects, amplifying the sample comprises performing polymerase chain reaction (PCR), rolling circle amplification (RCA), nucleic acid sequence based amplification (NASBA), loop-mediated amplification (LAMP), or a combination thereof. In further aspects, amplifying the sample comprises isothermal amplification of nucleotides or variable temperature amplification of nucleotides.

Any suitable device can be used to perform amplification according to the present disclosure. A variety of device features can be included, such as for example, a means for maintaining or cycling temperature, which can be used to enable the performance of PCR-based amplification. Other device features can include, without limitation, warm-water baths, incubators, and other heat sources, as well as insulators for trapping heat into a confined volume.

In various aspects, the present disclosure provides methods, devices, and systems for performing homogenous assays. As used herein, the term "homogeneous assay" refers to an assay in which all assay components exist in solution phase at the time of detection. In a homogeneous assay, no component of the assay scatters detectable light.

In further aspects, the present disclosure provides methods, devices, and systems for performing non-homogenous assays. As used herein, the term "non-homogeneous assay" refers to an assay in which one or more assay components are present in solid phase at the time of detection. The term non-homogenous assay is used interchangeably with the term "heterogeneous assay." Formation of a precipitate or particulate, such as in LAMP or rolling circle amplification, is a common form of a heterogeneous assay. In this type of assay, the solid-phase components can scatter detectable light.

In various aspects, the present disclosure provides methods, devices, and systems for amplification by performing digital PCR (dPCR). Digital PCR is a method in which individual nucleic acid molecules present in a sample are distributed to many separate reaction volumes (e.g., chambers or aliquots) prior to PCR amplification of one or more target sequences. The concentration of individual molecules in the sample is adjusted so that at least some of the reaction volumes contain no target molecules and at least some of the reaction volumes contain at least one target molecule. Amplification of a target sequence results in a binary digital output in which each chamber is identified as either containing or not containing the PCR product indicative of the presence of the corresponding target sequence. A count of reaction volumes containing detectable levels of PCR end-product is a direct measure of the absolute nucleic acids quantity. In various aspects of the present disclosure, nucleic acid samples are distributed by partitioning them into separate reaction volumes. The digitized samples are then thermocycled in the presence of PCR reagents, thereby facilitating the amplification of the nucleic acid sample.

In a further aspect of the present disclosure, the methods, systems and devices described herein can be applied to isothermal amplification techniques, such as digital ELISA, NASBA, and LAMP. ELISA is protein based and usually used for the quantification of proteins or small molecules. NASBA and LAMP are isothermal amplification schemes that have been developed to complement PCR.

In an isothermal amplification, there is no temperature cycling occurring as in traditional PCR. There are several types of isothermal nucleic acid amplification methods such as transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification.

NASBA (Nucleic Acid Sequence Based Amplification) is an isothermal (~40° C.) process for amplifying RNA, and has been used successfully at detecting both viral and bacterial RNA in clinical samples. The advantages offered by NASBA are: (1) It has high amplification efficiency and fast amplification kinetics, where over thousand fold amplification can be achieved within an hour or two; (2) It does not give false positives caused by genomic dsDNA, as in the case of RT-PCR; (3) Gene expression studies can be performed without the use of intron flanking primers; (4) It does not require the degree of temperature control and feedback needed for PCR. As a result, NASBA has become popular for detecting viral and bacterial RNA. The fact that NASBA is an isothermal method makes it possible to run multiple samples simultaneously with the use of a temperature controlled oven, which is an important practical advantage in many field works.

LAMP, which stands for Loop-Mediated Isothermal Amplification, is capable of amplifying DNA with high specificity, efficiency, and rapidity under isothermal conditions (~60° C.). Because of the characteristics of its amplification reaction, LAMP is able to discriminate single nucleotide differences during amplification. As a result, LAMP has been applied for SNP (single nucleotide polymorphism) typing. LAMP has also been shown to have about 10 fold higher sensitivity then RT-PCR in the detection of viruses. Additionally, because LAMP amplification of DNA can be directly correlated with the production of magnesium pyrophosphate, which increases the turbidity of solution, the progress of LAMP has been monitored using a simple turbidimeter. Therefore, a non-homogenous assay can be used for detecting the amplification products that result from LAMP.

In one aspect, the present disclosure provides a method for performing digital loop-mediated amplification of a sample. The method can include producing a plurality of droplets of the sample on a microfluidic device, wherein at least one droplet in the plurality comprises a nucleic acid molecule (e.g., a DNA and/or a RNA molecule); and performing loop-mediated amplification in the at least one droplet to produce amplified product of the nucleic acid molecule. The method can also include detecting the amplified product. In some aspects, the method includes determining a number of droplets in the plurality that comprise the amplified product; and calculating a concentration of the nucleic acid molecule in the sample using individual volumes of the droplets in the plurality and the number of droplets in the plurality that contain the nucleic acid molecule. The microfluidic device can include a plurality of chambers configured to form the plurality of droplets.

Despite some of the advantages offered by NASBA and LAMP, one important drawback is the difficulty with performing quantification in the conventional real-time fashion or in bulk, which would be beneficial in most situations. Quantification often requires meticulous calibration and control using standards amplified under identical conditions, which can be very tedious (especially for field studies) and is not practical in many cases. For non-homogenous assays, such as the detection of precipitate in LAMP, accurate calibration can be especially challenging. This issue is effectively addressed with the present digital method that employs end-point detection.

Rolling circle amplification (RCA) is an isothermal nucleic-acid amplification method. It differs from the polymerase chain reaction and other nucleic-acid amplification schemes in several respects. During RCA, a short DNA probe anneals to a target DNA of interest, such as the DNA of a pathogenic organism or a human gene containing a deleterious mutation. The probe then acts as a primer for a Rolling Circle Amplification reaction. The free end of the probe anneals to a small circular DNA template. A DNA polymerase is added to extend the primer. The DNA polymerase extends the primer continuously around the circular DNA template generating a long DNA product that consists of many repeated copies of the circle. By the end of the reaction, the polymerase generates many thousands of copies of the circular template, with the chain of copies tethered to the original target DNA. This allows for spatial resolution of target and rapid amplification of the signal. The use of forward and reverse primers can change the above linear amplification reaction into an exponential mode that can generate up to $10^{12}$ copies in 1 hour. The calibration required for such quantitative measurements can be cumbersome.

To overcome this drawback, the present disclosure provides digital isothermal amplifications, such as NASBA and LAMP, where the use of an array of digitized volumes, similar to digital PCR, is used for carrying out digital NASBA, digital LAMP, and rolling circle amplification. Furthermore, by using concentration gradients and/or arrays of digitized volumes of different sizes, we can effectively increase the dynamic range of these digital measurements. The current method ideally complements these isothermal amplification schemes to make them a quantitative technique for measuring the presence of RNA and DNA. In another aspect of the disclosure, the method is applied to antibody based amplification. In another aspect, the method is applied to specific molecule recognition based amplification.

Various detectable agents can be used according to the present disclosure. In various aspects, the detectable agent is fluorescent. In further aspects, the detectable agent is luminescent. The detectable agent used can depend on the type of amplification method that is employed. In one aspect, the signal generation can come from a nonsequence specific fluorophore such as EvaGreen or SYBRgreen, where the fluorophore is quenched when in solution but can intercalate into double-stranded DNA where it exhibits much brighter fluorescence. Thus the large amount of double stranded DNA generated during PCR results in a significant increase in fluorescence. In another aspect sequence specific fluorescent probes are used. In one aspect this consists of a molecular beacon such as a hairpin structure, whose fluorescence is highly quenched in its closed conformation and whose intensity is increased once it hybridizes to amplified target DNA. In another aspect it consists of a Taqman probe, which hybridizes to the target DNA, and undergoes cleavage of a fluorescent reporter from the probe DNA during the next amplification step.

These probes have non-negligible background fluorescence and the relative increase in intensity during amplification can be rather small, depending of the amount of probe added to the reaction. Furthermore, the excitation intensity can vary across the field of view during the detection process. In some aspects, a threshold pixel intensity value is subtracted from all pixels in an image to determine whether fluorescence intensity in a droplet is large enough to indicate the presence of an amplification product. In some aspects, a reference dye, whose spectral signature can be well separated from the fluorescence probe that reports on amplification, and whose fluorescent signal is insensitive to amplification or other reaction or reagent conditions, can be added to one or more immiscible fluid.

Analysis Methods and Systems

In various aspects, the present disclosure provides methods for performing a digital assay. A plurality of polydisperse droplets may be produced. At least some of the droplets may comprise a sample. The sample may be amplified. The sample may be labeled with a detectable agent. An image stack for a droplet may be obtained. The volume of the droplet may be determined from the image stack. The presence or absence of the detectable agent in the droplet may be determined from the image stack. The concentration of the sample in the plurality of droplets may be determined based on the presence or absence of the detectable agent in a plurality of droplets.

The image stack may be obtained by optical imaging. The detectable agent may be detected by optical imaging. The optical imaging may be performed in many ways such as by confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epifluorescence microscopy, bright field imaging, dark field imaging, oblique illumination, or a combination thereof. In some aspects, the optical imaging comprises the use of adaptive optics and imaging.

The image stack may comprise a plurality of images taken from separate depths of focus through a single droplet. The image stack may comprise 2, 3, 4, 5, 6, 7, 8, 9, 10, 15, 20, 25, 30, 35, 40, 45, 50, 55, 60, 65, 70, 75, 80, 85, 90, 95 or 100 images taken from separate depths of focus for a droplet.

The methods of the present disclosure may be performed concurrently on a plurality of droplets. The plurality of polydisperse droplets may comprise an array of polydisperse droplets. The array of polydisperse droplets may be disposed in a multi-well plate.

The volume of the droplet may be determined from the image stack in many ways such as by the Line Scan Method, Simple Boundary Method, Reverse Watershed Method, Circle Detection Method, Combined Reverse Watershed and Circle Detection Method, or a combination thereof. The concentration of the detectable agent may be determined over a dynamic range of at least three orders of magnitude or over a dynamic range of at least six orders of magnitude.

The plurality of polydisperse droplets may comprise a first fluid and a second fluid. The first fluid may be immiscible in the second fluid. An emulsion of polydisperse droplets may be formed by agitating a solution comprising a first fluid and a second fluid, wherein the first fluid is immiscible in the second fluid. To form the emulsion of polydisperse droplets, a solution comprising a first fluid and a second fluid may be agitated. The first fluid may be immiscible in the second fluid. The emulsion may be agitated in a third fluid. The third fluid may be immiscible in the second fluid, thereby forming a double emulsion. The fluid(s) may be agitated in many ways such as shaking, vortexing, sonicating, mixing with magnets, extrusion, flow focusing or a combination thereof. The agitation may be sufficient to form an emulsion. Extrusion, for example, may comprise pipetting the fluid, wherein the pipetting is sufficient to produce the emulsion. The agitating may occur in a microfluidic device. The agitation may be, for example, vortexing. The emulsion produced may comprise an aqueous phase and a non-aqueous phase. The first fluid may comprise water and the second fluid may comprise oil. The first fluid may comprise water, the second fluid may comprise oil, and the third fluid may comprise water.

The plurality of polydisperse droplets may comprise a plurality of emulsions. The plurality of emulsions may be prepared by combining three or more immiscible fluids. The first fluid may be aqueous. The first fluid may comprise sample. The second fluid may comprise an oil. The second fluid may comprise an oil and the second fluid may be immiscible with the first fluid and the third fluid. The first fluid may be different from the third fluid. The third fluid may comprise an oil and the third fluid may be immiscible with the first fluid and the second fluid.

The plurality of polydisperse droplets may further comprise a fluid interface modification element. The fluid interface modification element may comprise a surfactant. The fluid interface modification element may be selected from a lipid, phospholipid, glycolipid, protein, peptide, nanoparticle, polymer, precipitant, microparticle, a molecule with a hydrophobic portion and a hydrophilic portion, or a combination thereof.

One or more of the immiscible fluids may be converted to a gel or solid. The immiscible fluid may be converted to a gel or solid before amplifying the sample, during amplifying the sample, or after amplifying the sample.

The detectable agent may be fluorescent or luminescent. The detectable agent may comprise one or more of fluorescein, a derivative of fluorescein, rhodamine, a derivative of rhodamine, or a semiconducting polymer. The sample may comprise a nucleotide.

To amplify the sample, polymerase chain reaction (PCR), rolling circle amplification (RCA), nucleic acid sequence based amplification (NASBA), loop-mediated amplification (LAMP), or a combination thereof may be performed. Alternatively or in combination, the sample may be amplified by isothermal amplification of nucleotides or variable temperature amplification of nucleotides.

The distribution of droplet diameters may have a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the median droplet diameter. Alternatively or in combination, the distribution of droplet diameters may have a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the mean droplet diameter.

The volumes in the polydisperse droplets may vary by more than a factor of 2, by more than a factor of 10, by more than a factor of 100, by more than a factor of 1000, by more than a factor of 10000, by more than a factor of 100000, by more than a factor of 1000000, by more than a factor of about 2, by more than a factor of about 10, by more than a factor of about 100, by more than a factor of about 1000, by more than a factor of about 10000, by more than a factor of about 100000, or by more than a factor of 1000000. The polydisperse droplets may have a volume distribution of from 100 nanoliters (nL) to 1 femtoliters (fL), from 10 nL to 10 fL, from 1 nL to 100 fL, from 100 nL to 1 pL, from 10 nL to 10 pL, or from 1 nL to 1 pL, from about 500 pL to about 50 fL, from about 100 pL to about 100 fL. The mean volume of the polydisperse droplets may change by less than 50%, less than 40%, less than 35%, less than 30%, less than 25%, less than 20%, less than 15%, less than 10%, less than 5%, less than 4%, less than 3%, less than 2%, or less than 1% during amplifying the sample.

Amplifying the sample may comprise a first amplification cycle, and fewer than 50%, fewer than 45%, fewer than 40%, fewer than 35%, fewer than 30%, fewer than 25%, fewer than 20%, fewer than 19%, fewer than 18%, fewer than 17%, fewer than 16%, fewer than 15%, fewer than 14%, fewer than 13%, fewer than 12%, fewer than 11%, fewer than 10%, fewer than 9%, fewer than 8%, fewer than 7%, fewer than 6%, fewer than 5%, fewer than 4%, fewer than 3%, fewer than 2%, or fewer than 1% of the polydisperse droplets may fuse after the first amplification cycle.

The refractive index of the first fluid may differ from the refractive index of the second fluid by less than 200%, less than 100%, less than 60%, less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

In various aspects, the present disclosure provides methods for performing a digital assay. A plurality of polydisperse droplets may be produced. At least some of the droplets may comprise a sample. The sample may be amplified. The sample may be labeled with a detectable agent. The plurality of polydisperse droplets may be flowed through a flow cytometry channel. The volume of a droplet may be determined as it flows through the flow cytometry channel. The presence or absence of the detectable agent in the droplet may be determined. The concentration of the sample in the plurality of droplets may be determined based on the presence or absence of the detectable agent in the plurality of polydisperse droplets. In some aspects, the size of the droplet and/or concentration of the sample in the droplet may be determined by detecting light scattered from the droplet.

In various aspects, the present disclosure provides compositions for performing digital assays. A composition may comprise a first fluid, a second fluid, a surfactant, and an amplification reagent. The first fluid and the second fluid may be immiscible in each other and may be capable of forming an emulsion when agitated. In some aspects, the composition may further comprise a sample, such as a nucleotide, and/or a detectable agent capable of labeling the sample. The sample may be labeled with the detectable agent.

The composition may further comprise a detectable agent capable of binding a nucleic acid sample.

The amplification reagent of the composition may be selected from a polymerase chain reaction (PCR) reagent, rolling circle amplification (RCA) reagent, nucleic acid sequence based amplification (NASBA) reagent, loop-mediated amplification (LAMP) reagent, or a combination thereof. The amplification reagent may comprise a PCR reagent such as a thermostable DNA polymerase, a nucleotide, a primer, probe or a combination thereof.

The composition may further comprise a third fluid. The third fluid may be immiscible in the second fluid. The composition may be capable of forming a double emulsion. The first fluid may be aqueous. The first fluid may comprise the amplification reagent. The second fluid may comprise an oil. The second fluid may be immiscible with the first fluid and the third fluid. The first fluid may be different from the third fluid. The third fluid may comprise an oil and may be immiscible with the first fluid and the second fluid.

The composition may further comprise a fluid interface modification element. The fluid interface modification element may comprise a surfactant. The fluid interface modification element may be selected from a lipid, phospholipid, glycolipid, protein, peptide, nanoparticle, polymer, precipitant, microparticle, a molecule with a hydrophobic portion and a hydrophilic portion, or a combination thereof.

The composition may further comprise a solidifying or gelling agent capable of converting one or more of the immiscible fluids to a gel or solid.

In some aspects, the present disclosure provides kits for performing a digital assay comprising any of the aforementioned compositions.

In various aspects, the present disclosure provides systems for determining a volume of a droplet(s). The system may comprise a container, an imaging source, and a computing device. The container may be configured for holding the droplet(s). The imaging source may be configured to obtain an image of the droplet(s) in the container. The computing device may comprise a processor and a memory (e.g., a non-transitory, tangible computer-readable storage medium such as a ROM, RAM, flash memory, or the like). The memory may store a set of instructions that when executed by the processor cause (i) the imaging source to obtain an image stack of the droplet(s) and (ii) the processor to determine the volume of the droplet(s) in the sample based on the obtained image stack.

The droplet(s) may comprise a plurality of droplets. The plurality of droplets may be polydisperse. The container may comprise a multi-well plate.

The imaging source may comprise an optical imaging source. The optical imaging source may be configured to perform confocal microscopy, line confocal microscopy, deconvolution microscopy, spinning disk microscopy, multiphoton microscopy, planar illumination microscopy, Bessel beam microscopy, differential interference contrast microscopy, phase contrast microscopy, epiflouorescent microscopy, bright field imaging, dark field imaging, oblique illumination, or a combination thereof.

The image stack for the droplet(s) may comprise a plurality of images taken from separate depths of focus through the droplet. The image stack may comprise 2, 3, 4, 5, 6, 7, 8, 9, 10, 15, 20, 25, 30, 35, 40, 45, 50, 55, 60, 65, 70, 75, 80, 85, 90, 95 or 100 images taken from separate depths of focus for the droplet.

The set of instructions when executed by the processor may cause the processor to determine the volume of the droplet(s) by (i) identifying a pixel set(s) in an individual image of the image stack, (ii) identifying the pixel set(s) as at least a part of at least one droplet, (iii) identifying an individual droplet(s) from the pixel set(s) based on the correspondence, and (iv) determining the volume of the identified droplet(s) based on the pixel set(s). The at least at part of the at least one droplet may comprise a single droplet, parts of multiple droplets, a single whole droplet, a plurality of whole droplets, or combinations thereof.

The set of instructions when executed by the processor may cause the processor to determine a plurality of volumes of a plurality of droplets based on the obtained image stack. The set of instructions when executed by the processor may further cause the processor to determine the presence or absence of a detectable agent in at least some of the plurality of droplets. The set of instructions when executed by the processor may further cause the processor to determine the concentration of a sample in the plurality of droplets based on the presence or absence of the detectable agent in the plurality of droplets and the determined plurality of volumes of the plurality of droplets. The sample may comprise a nucleotide. The detectable agent may be fluorescent or luminescent. The detectable agent may comprise fluorescein, a derivative of fluorescein, rhodamine, a derivative of rhodamine, or a semiconducting polymer.

The plurality of droplets may comprise a sample comprising a nucleotide. The sample in the plurality of droplets may have been amplified. The sample in the plurality of droplets may have been amplified by performing polymerase chain reaction (PCR), digital polymerase chain reaction (dPCR), rolling circle amplification (RCA), nucleic acid sequence based amplification (NASBA), loop-mediated amplification (LAMP), or a combination thereof. The sample may have been amplified by isothermal amplification of nucleotides or variable temperature amplification of nucleotides. The set of instructions when executed by the processor may cause a concentration of the detectable agent to be determined over a dynamic range of at least three orders of magnitude or over a dynamic range of at least six orders of magnitude.

In various aspects, the present disclosure provides methods for determining a volume of a droplet. An image stack of the droplet may be obtained. A pixel set(s) in an individual image of the image stack may be identified. The pixel set(s) may be identified as corresponding to at least a part of at least one droplet, which may comprise a part of a single droplet, parts of multiple droplets, a whole droplet, a plurality of whole droplets, or combinations thereof. Individual droplet(s) may be identified from the pixel set(s) based on the correspondence. The volume of the identified individual droplet(s) may be determined based on the pixel set(s).

The image stack of the sample may be obtained by obtaining a plurality of images taken from separate depths of focus through a droplet(s). 2, 3, 4, 5, 6, 7, 8, 9, 10, 15, 20, 25, 30, 35, 40, 45, 50, 55, 60, 65, 70, 75, 80, 85, 90, 95 or 100 images may be taken from separate depths of focus for the droplet(s).

The volume of the identified droplet(s) may be determined by determining the diameter of the identified droplet(s) by using at least one image of the image stack in the following ways, alone or in various combinations. One, the identified droplet(s) may be correlated between a plurality of images of the image stack and a largest diameter of the identified droplet(s) in the plurality of images may be measured. Two, a curve may be fit to a boundary of the identified droplet(s) and the diameter of the identified droplet(s) may be interpolated based on the fitted curve. Three, the diameters of the identified droplet(s) may be correlated between a plurality of images of the image stack, the diameter of the identified droplet(s) may be identified in each image, and the diameter of the identified droplet(s) may be determined from its diameters in the plurality of images of the image stack. Four, the identified droplet(s) may be correlated between a plurality of images of the image stack, the diameter of the identified droplet(s) may be determined in each image, and the diameter of the identified droplet(s) may be determined from its diameters in the plurality of images of the image stack and a difference in image depth between the plurality of images. Other ways of determining the diameter of the identified droplet(s) are also contemplated and are within the scope of the present disclosure.

The volumes of a plurality of droplets may be determined. The presence or absence of a detectable agent in the plurality of droplets may be determined from the image stacks. The concentration of a sample in the plurality of droplets may be determined based on the presence or absence of the detectable agent in the plurality of droplets and the determined volumes of the plurality of droplets.

The sample may comprise a nucleotide. The sample in the plurality of droplets may be amplified in many ways such as by performing polymerase chain reaction (PCR), rolling circle amplification (RCA), nucleic acid sequence based amplification (NASBA), loop-mediated amplification (LAMP), or a combination thereof. Alternatively or in combination, the sample may be amplified by isothermal amplification of nucleotides or variable temperature amplification of nucleotides.

The concentration of the detectable agent may be determined over a dynamic range of at least three orders of magnitude or over a dynamic range of at least six orders of magnitude. The detectable agent may be fluorescent or luminescent. The detectable agent may comprise fluorescein, a derivative of fluorescein, rhodamine, a derivative of rhodamine, or a semiconducting polymer.

The image stack may be obtained by optical imaging. The optical imaging may be performed by confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epifluorescence microscopy, bright field imaging, dark field imaging, oblique illumination, or a combination thereof.

An image stack of a plurality of polydisperse droplets may be obtained. The plurality of polydisperse droplets may comprise a first fluid and a second fluid. The first fluid may be immiscible in the second fluid. An emulsion of polydisperse droplets may be formed by agitating a solution comprising a first fluid and a second fluid. To obtain the image stack, the formed emulsion may be imaged. The first fluid may comprise water and the second fluid may comprise oil.

Furthermore, an emulsion of polydisperse droplets may be formed by agitating a solution comprising a first fluid and a second fluid. The first fluid may be immiscible in the second fluid. And, the emulsion may be agitated in a third fluid. The third fluid may be immiscible in the second fluid, thereby forming a double emulsion. The first fluid may comprise water, the second fluid may comprises oil, and the third fluid may comprises water. The fluid(s) may be agitated in many ways such as by shaking, vortexing, sonicating, mixing with magnets, extruding, flow focusing or a combination thereof. The agitation may be sufficient to form an emulsion. The extrusion, for example, may comprise pipetting the fluid, wherein the pipetting is sufficient to produce an emulsion. The agitating may occur in a microfluidic device.

The emulsion may comprise an aqueous phase and a non-aqueous phase. The polydisperse droplets may comprise a plurality of emulsions. The polydisperse droplets may comprise a plurality of emulsions. The plurality of emulsions may be prepared by combining three or more immiscible fluids. The three or more immiscible fluids may comprise a first fluid, a second fluid, and a third fluid. The first fluid may be aqueous. The second fluid may comprise an oil. The second fluid may be immiscible with the first fluid and the third fluid. The immiscible first, second, and/or third fluid(s) may be converted into a gel or solid. The first fluid may be different from the third fluid. The third fluid may comprise an oil. The third fluid may be immiscible with the first fluid and the second fluid. The immiscible third fluid may be converted into a solid or gel. The first fluid may comprise a sample for detection. The refractive index of the first fluid may differs from the refractive index of the second fluid by less than 200%, less than 100%, less than 60%, less than 50%, less than 45%, less than 40%, less than 35%, less than 30%, less than 25%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

The plurality of polydisperse droplets may further comprise a fluid interface modification element. The fluid interface modification element may comprise a surfactant. The fluid interface modification element may be selected from a lipid, phopholipid, glycolipid, protein, peptide, nanoparticle, polymer, precipitant, microparticle, a molecule with a hydrophobic portion and a hydrophilic portion, or a combination thereof. For example, the fluid interface modification element may comprise a PEG-based surfactant.

The distribution of droplet diameters may have a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the median droplet diameter. The distribution of droplet diameters may have a standard deviation greater than 1000%, greater than 500%, greater than 100%, greater than 50%, greater than 30%, greater than 20%, greater than 15%, greater than 10%, greater than 9%, greater than 8%, greater than 7%, greater than 6%, or greater than 5% of the mean droplet diameter.

The volumes in the polydisperse droplets may vary by more than a factor of 2, by more than a factor of 10, by more than a factor of 100, by more than a factor of 1000, by more than a factor of 10000, by more than a factor of 100000, by more than a factor of 1000000, by more than a factor of about 2, by more than a factor of about 10, by more than a factor of about 100, by more than a factor of about 1000, by more than a factor of about 10000, by more than a factor of about 100000 or by more than a factor of 1000000.

The polydisperse droplets may have a volume distribution of from 100 nanoliters (nL) to 1 femtoliters (fL), from 10 nL to 10 fL, from 1 nL to 100 fL, from 100 nL to 1 pL, from 10 nL to 10 pL, or from 1 nL to 1 pL, from about 500 pL to about 50 fL, from about 100 pL to about 100 fL.

The sample may be amplified for detection in the polydisperse droplets.

The mean volume of the polydisperse droplets may change by less than 50%, less than 40%, less than 35%, less than 30%, less than 25%, less than 20%, less than 15%, less than 10%, less than 5%, less than 4%, less than 3%, less than 2%, or less than 1% during amplifying the sample.

Amplifying the sample may comprise a first amplification cycle, and fewer than 50%, fewer than 45%, fewer than 40%, fewer than 35%, fewer than 30%, fewer than 25%, fewer than 20%, fewer than 19%, fewer than 18%, fewer than 17%, fewer than 16%, fewer than 15%, fewer than 14%, fewer than 13%, fewer than 12%, fewer than 11%, fewer than 10%, fewer than 9%, fewer than 8%, fewer than 7%, fewer than 6%, fewer than 5%, fewer than 4%, fewer than 3%, fewer than 2%, or fewer than 1% of the polydisperse droplets may fuse after the first amplification cycle.

Further, the pixel set(s) in an individual image of the image stack may be identified by obtaining a plurality of line scans within the individual image, setting a threshold level, and identifying an area in the plurality of the line scans outside the threshold level as the pixel set(s) (e.g., the area may be outside the threshold level if it is below or above the threshold level). While line scans are generally discussed herein, other methods of generating scans are also contemplated. These methods may include confocal scanning, line illumination and collection, Nipkow disc type scanning, or the like.

To identify one or more droplets in an image, the Simple Boundary method may be used. To perform the Simple Boundary Method, one or more pixel sets of the individual image of the image stack above a threshold may be identified. The pixel set may include a part of a single droplet, parts of multiple droplets, a whole droplet, whole droplets, or combinations thereof. The pixel set may be identified as corresponding to one droplet by determining an aspect ratio of the pixel set. The pixel set may be identified as corresponding to one droplet when the aspect ratio of the pixel set is less than or equal to a threshold value. The threshold value may be 1, 1.1, 1.2, 1.3, 1.4, 1.5, 1.6, 1.7, 1.8, 1.9, or 2.

To identify droplet(s) in an image, a Reverse Watershed Method may be performed. Performing the Reverse Watershed Method may comprise generating a map based on pixel intensities of the individual image of the image stack, identifying one or more pixel sets in the generated map, identifying an individual pixel set as a region of interest, and fitting a boundary of the region of interest with a best-fit circle. The pixel set may include a part of a single droplet, parts of multiple droplets, a whole droplet, a plurality of whole droplets, or combinations thereof. The individual image of the image stack may be smoothed before generating the map. The map generated based on pixel intensities of the individual images of the image stack may comprise a topological map. To identify the one or more pixel set(s), whether an individual pixel comprises a background pixel or a droplet pixel may be determined based on the pixel intensity of the individual pixel and one or more threshold values. The individual pixel set may be identified as a region of interest when the individual pixel set has an area above a minimum required area. Further, whether the individual pixel set comprises a plurality of regions of interest may be determined and the plurality of regions of interest may be combined into a single region of interest. The region of interest may include a part of a single droplet, parts of multiple droplets, a whole droplet, a plurality of whole droplets, or combinations thereof.

To identify one or more droplets in an image, a Circle Detection Method may be performed. To perform the Circle Detection Method, one or more pixel sets of the individual image of the image stack above a threshold may be identified, a plurality of circles may be superimposed over the identified one or more pixel sets, one or more circles of the superimposed plurality of circles may be rejected when the one or more circles do not meet at least one predetermined criteria, and one or more remaining circles may be identified as corresponding to the droplet. The pixel set may include a part of a single droplet, parts of multiple droplets, a whole droplet, a plurality of whole droplets, or combinations thereof.

To identify one or more droplets in an image, a Combined Reverse Watershed and Circle Detection Method may be performed. To perform the Combined Reverse Watershed and Circle Detection method, a map based on pixel intensities of the individual image of the image stack may be generated, one or more pixel sets in the map may be identified, an individual pixel set may be identified as a region of interest, a plurality of circles may be superimposed over the region of interest, one or more circles of the superimposed plurality of circles may be rejected when the one or more circles do not meet at least one predetermined criteria, and one or more remaining circles may be identified as corresponding to one droplet. The pixel set may include a part of a single droplet, parts of multiple droplets, a whole droplet, a plurality of whole droplets, or combinations thereof. The individual image of the image stack may be smoothed before generating the map. The map based on pixel intensities of the individual images of the image stack may comprise a topological map. To identify the one or more pixel sets, an individual pixel may be identified as a background pixel or a droplet pixel based on the pixel intensity of the individual pixel and one or more threshold values. The region of interest may include a part of a single droplet, parts of multiple droplets, a whole droplet, a plurality of whole droplets, or combinations thereof.

An individual pixel set may be determined to comprise a region of interest if the individual pixel set has an area above a minimum required area. The at least one predetermined criteria may comprise one or more of (i) selecting one or more circles that include a largest fraction of external boundary pixels of the region of interest, (ii) selecting one or more circles that include a largest fraction of an area of the region of interest, (iii) rejecting one or more circles that include pixels from a different pixel group than the region of interest, (iv) rejecting one or more circles that include a substantial number of non-group pixels, or (v) discriminating against one or more circles that have a substantial fraction of their circumference in the interior of the pixel group.

To reject the one or more circles, the plurality of superimposed circles may be examined in pairs. The examined circles may comprise a first circle and a second circle. Further, one of the first or second circles may be rejected based on a vote which may be user-defined.

The one or more remaining circles may be identified as corresponding to one droplet by assigning the one or more remaining circles to one droplet. The one or more circles may be assigned to one droplet based on one or more of (i) assigning the to the droplet the circle with the best goodness of fit statistic to the droplet or (ii) assigning the region of interest to the droplet having a largest overlap in area with the one or more circles of the region of interest.

To determine the volume of the identified droplet based on the region of interest, one or more diameters of the one or more identified circles corresponding to the droplet may be determined.

In various aspects, the present disclosure provides systems for performing digital assays. The system may comprise a container, an imaging source, and a computing device. The container may be configured for holding a plurality of polydisperse droplets. At least some of the droplets may comprise a sample labeled with a detectable agent. The imaging source may be configured to obtain an image stack of the plurality of polydisperse droplets held in the container. The computing device may be configured to operate the imaging source. The computing device may comprise a processor and a memory (e.g., a non-transitory, tangible computer-readable storage medium such as a ROM, RAM, flash memory, or the like). The memory may store a set of instructions that when executed by the processor cause (i) the imaging source to obtain the image stack of the plurality of polydisperse droplets held in the container, (ii) the processor to determine the volumes of the plurality of polydisperse droplets based on the obtained image stack, (iii) the processor to determine the presence or absence of the detectable agent in the plurality of polydisperse droplets, and (iv) the processor to determine the concentration of the sample in the plurality of droplets based on the presence or absence of the detectable agent in the plurality of polydisperse droplets and the volumes of the plurality of polydisperse droplets.

The container may comprise a multi-well plate. The imaging source may comprises an optical imaging source. The optical imaging source may be configured to perform one or more of confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epiflouorescent microscopy, bright field imaging, dark field imaging, oblique illumination, or a combination thereof.

The obtained image stack may comprise a plurality of images taken from separate depths of focus through a single droplet. The image stack may comprise 2, 3, 4, 5, 6, 7, 8, 9, 10, 15, 20, 25, 30, 35, 40, 45, 50, 55, 60, 65, 70, 75, 80, 85, 90, 95 or 100 images taken from separate depths of focus for the single droplet.

The set of instructions when executed by the processor may cause the processor to determine the volumes of the plurality of polydisperse droplets by (i) identifying a pixel set(s) in an individual image(s) of the image stack, (ii) identifying the pixel set(s) as corresponding to at least a part of at least one droplet (which may comprise a part of a single droplet, parts of multiple droplets, a whole droplet, a plurality of whole droplets, or combinations thereof), (iii) identifying individual droplets from the pixel set or sets and (iv) determining the volume of the identified droplet(s) based on the pixel set(s).

The sample may comprise a nucleotide. The sample may have been amplified. The detectable agent may be fluorescent or luminescent. The plurality of polydisperse droplets may comprise a first fluid and a second fluid, the first fluid being immiscible with the second fluid.

The systems of the present disclosure further include a detection system configured to analyze the volumes and the presence or absence of sample in the plurality of droplets. The detection systems can include detectors for analyzing the contents of the volumes, determining volumes of droplets, and/or other characteristics of interest. The methods described herein will be generally compatible with any known systems capable of detecting and analyzing volumes (e.g., droplets and/or wells).

In various aspects, the present disclosure provides systems and methods for performing digital measurements of samples. In certain aspects, droplets can be identified and their volumes measured using the presently described systems and methods. In some aspects, the volume of a droplet is measured by obtaining an image stack for a given droplet. Each image in the image stack corresponds to a measurement taken in a single plane. Obtaining images for two or more planes in a given droplet enables the determination of droplet volume. If the droplet is sufficiently small, it may be possible to determine its volume from its appearance in a single image of the image stack. The image stack can also be referred to as a "z-stack" since typically the focal planes are separated by a user-chosen distance in the z-direction of the microscope's optical system. The height of a given z-stack can be as large as the working distance of the microscope objective being used. In further aspects, the presence or absence of sample in a given droplet can be determined for a given droplet. In certain aspects, the droplet volume and determination of the presence or absence of sample in each of a plurality of droplets can be used to determine the probability that any given droplet in the plurality of polydisperse droplets would contain sample, which can then be used to determine the concentration of sample.

In various aspects, the present disclosure provides systems for using digital measurements to determine a concentration of a sample. The systems can include a sample holder containing a plurality of polydisperse droplets having a volume distribution; a detector for detecting droplet size (i.e., volume) and a detectable agent contained in at least one droplet of the plurality of polydisperse droplets; and a computer comprising a memory device with executable instructions stored thereon, the instructions, when executed by a processor, cause the processor to: analyze a plurality polydisperse droplets having a volume distribution to determine the volumes of the droplets and whether they contain a detectable agent to determine the concentration of the sample. In some aspects, the concentration of the detectable agent in the sample is used to calculate the sample concentration. In various aspects, the concentration of detectable agent is directly correlated with the concentration of sample.

In various aspects, droplet diameter and the presence of a detectable agent is detected by an optical detection method. Any detector, or component thereof, that operates by detecting a measureable optical property, such as the presence of light, comprises an optical detector. Examples of optical detectors include, but are not limited to, cameras, photomultiplier tubes, photodiodes and photodiode arrays, and microscopes, and associated components thereof, such as objectives, optical filters, mirrors, and the like.

In certain aspects, the signal detected by an optical detector, or other suitable detector, is processed in order to interpret the signals being measured by the detector. In certain aspects, the measured information is processed by a device, apparatus, or component thereof that stores and/or processes information acquired by a detector, such as, e.g., an optical detector. Examples of an information processor include, but are not limited to, a personal computing device that stores information acquired by a detector, and software running on the personal computing device that processes the information. In other aspects, an information processor or component thereof can be embedded in a detector, such as in a chip embedded in a camera that stores optical information acquired by the camera either permanently or temporarily. In other aspects, an information processor and a detector can be components of a fully integrated device that both acquires and processes optical information to perform a digital assay.

In yet another aspect, the systems can include a computer-readable storage medium for conducting digital measurements. The computer-readable storage medium has stored thereon instructions that, when executed by one or more processors of a computer, cause the computer to: analyze a plurality of droplets having a volume distribution to determine a number of droplets in the plurality that contain the detectable agent; and use the number of droplets in the plurality of droplets, the volumes of some or all of the droplets in the plurality and the number of droplets in the second plurality containing one or more detectable agents to determine a concentration of the detectable agent in the sample.

In another aspect, systems are provided for analyzing volumes to detect and calculate information for a given droplet. The system includes one or more processors, and a memory device including instructions executable by the one or more processors. When the instructions are executed by the one or more processors, the system at least receives a user input to analyze volumes (e.g., a plurality of droplets). The system can be configured to carry out aspects of the methods of the present disclosure, such as counting a number of volumes (e.g., droplets), determining volumes of a plurality of droplets in a volume distribution and use the number of the droplets containing one or more detectable agents to determine a concentration of the detectable agent in the sample. The system also provides data to a user. The data provided to the user can include the concentration of the detectable agent in the sample or a sample concentration.

In some aspects of the present disclosure, the presence of one or more target molecules within a droplet is indicated by an increase of fluorescence in a particular wavelength range. In some aspects, a PCR reaction product indicates the presence of the target molecule by an increase in the fluorescence in a particular wavelength range (indicator fluorescence). In some aspects, a reference agent can be utilized in parallel with the target molecule. According to this aspect, the droplets emit fluorescence (i.e., reference fluorescence) in a wavelength range separate from that of the target molecule regardless of whether the target molecule is present. For a given set of droplets, separate sets of images of the indicator fluorescence and reference fluorescence are obtained and the droplets in each are identified and measured. The indicator and reference fluorescence from a given droplet can be compared. In some aspects, the ratio of the indicator to reference fluorescence can be used to indicate whether that particular droplet contains the target molecule. In other aspects, the absolute intensity of the indicator fluorescence would be sufficient to indicate if the droplet contained target. In some aspects, the average value of the background pixels or a multiple thereof can be subtracted from the pixel intensities within the droplets before the fluorescence intensities of the indicator and reference intensities are compared. By performing this analysis, a list of droplet diameters is obtained, and for each measured droplet, a binary measure is obtained defining whether the droplet is occupied (contains one or more target molecules) or not. The list of droplet sizes and the total number of occupied droplets can then be used to obtain the target concentration of the sample.

There are many possible ways to measure the size, contents, and/or other aspects of polydisperse droplets in an emulsion while applying the methods of the present disclosure. In some aspects, droplets can be measured optically by an optical detector comprising a flow cytometer. According to this aspect, droplets can flow through a large flow channel where droplet shapes are not distorted and their volumes can be determined by computer software, based on measurements of light scattering patterns acquired by an optical detector, such as a photomultiplier tube, as the droplets pass a source of light excitation. In other aspects, droplets can pass through a narrow flow channel where the droplets conform to the channel width. According to this aspect, the volume of the disperse droplets can be determined by using the channel width and the length of the individual droplets in the channel to define their volume.

A variety of signal detection methods can be used according to the present disclosure. In various aspects, the present methods and systems provide for detection of droplet aspects using optical detection methods and optical detectors. In some aspects, the emulsion system can be measured optically by an optical detector comprising a fluorescence microscope and its associated components. Images can be acquired with, for example, a confocal laser scanning microscope, a spinning-disk (Nipkow disk) confocal microscope, or a microscope that uses programmable arrays of mirrors or spatial light modulators to acquire data from multiple focal depths. In other aspects, images can be acquired with an epifluorescence microscope. In some aspects, images acquired with an epifluorescence microscope can be processed subsequently using 3D deconvolution algorithms performed by computer software. In other aspects, images can be acquired with a multi-photon microscope, such a two-photon microscope. In other aspects images can be acquired using planar illumination microscopy, Bessel beam microscopy, differential interference contrast microscopy, phase contrast microscopy, bright field imaging, dark field imaging, or oblique illumination. In some aspects, images can be acquired using a combination of the imaging devices and methods listed herein, or any other suitable imaging devices and methods that can reasonably be applied to the present methods.

The method of droplet imaging provides information on both the droplet size and whether the droplet contains a target molecule of interest, which are used according to the present method for the determination of sample concentration. In some aspects, droplet size and signal intensity can be determined based on optical information acquired using confocal fluorescence microscopy. According to this aspect, the emulsion can be stored in a well, chamber, or other container and multiple sets of image stacks can be acquired from it. In some aspects, for each sample area in a given polydisperse droplet sample, an image stack is collected, consisting of at least two images taken at approximately the same XY-position (same sample area) but different Z-positions (different depths). Droplet(s) in the sample area that are larger than the spacing in Z will appear in multiple frames at approximately the same XY position, but with different diameters. The image stack enables the determination of various parameters, including the droplet size and the presence of absence of a target analyte in the droplet.

In some aspects, droplet diameters are determined by an information processor based solely on droplets' boundaries determined in the frame of a Z-stack that contains the largest diameter. In other aspects, droplet diameters are determined by an information processor based on droplet boundaries determined at multiple images in a Z stack, and the relative positions of the images in the Z dimension. This method can include an assumption of spherical droplet shape, or some other modified shape, depending on multiple factors including the refractive indices of the two fluids, the relative density of the two fluids and the surface tension.

There are numerous methods to identify and select individual droplets according to the present disclosure. In one aspect, line scans are obtained within the image and, after setting an appropriate threshold level, the diameter of regions of interest are measured. In another aspect, a threshold for each image is chosen, and the areas above the threshold are evaluated as possible single droplets. If the area is sufficiently round (i.e., has an aspect ratio below a selected threshold level), then the area is considered to be a single droplet. A list of droplets is generated for each image.

In some aspects, once droplets in an image have been identified, they are correlated between different frames of the image stack. The largest droplets will appear in more than one image so it is necessary to identify the trail of circles through the frames of the image stack. Droplet correlation can be readily accomplished by using any number of suitable tracking algorithms as would be known to one of ordinary skill in the art. Tracking is generally facilitated by the fact that droplets do not move significantly between frames and because the droplets of interest are fairly large (in pixels). According to the present disclosure, the diameter of a particular droplet can be assumed to be that of the largest circle associated with it in the image stack. Alternatively, a curve can be fit to the circle diameters of a particular droplet and the largest diameter interpolated from that curve. That largest diameter would then be used as the diameter of the droplet. In various aspects of the present disclosure, a plurality of images in the image stack are obtained and used to determine the various parameters of interest for a given droplet, and the droplet itself is not required to undergo additional assaying.

The present methods are amenable to automation and any suitable method can be used for the identification, selection, and analysis of droplets and the samples contained within those droplets. Exemplary methods include the Line Scan Method, Simple Boundary Method, Reverse Watershed method, Modified Reverse Watershed Method, Circle Detection Method, Circle Hough Transform Method, and Combined Reverse Watershed and Circle Detection Method. Other methods are also contemplated and within the scope of the present disclosure. Each of these methods is described below.

Line Scan Method. In one aspect of the present disclosure, the Line Scan Method can be used to analyze droplets in a polydisperse droplet system. According to this aspect, line scans are obtained within the image and, after setting an appropriate signal threshold level, the diameter of regions of interest are measured.

Simple Boundary Method. In one aspect of the present disclosure, the Simple Boundary Method can be used to analyze droplets in a polydisperse droplet system. According to this aspect, a threshold for each image is initially chosen. Pixel sets in a given sample that are above the threshold are evaluated as possible single droplets. If the pixel set is sufficiently round (i.e., has an aspect ratio below a chosen level) then the area is considered to be a single droplet. A list of droplets is subsequently generated for each image.

Reverse Watershed Method. In one aspect of the present disclosure, the Reverse Watershed Method can be used to analyze droplets in a polydisperse droplet system. In the standard watershed method, the pixel intensities of the image are treated as elevations in a 3D topographical map. "Water" is introduced at the local minima where the height of the water relative to a global zero point is the same for all "pools." As the water height is raised uniformly, the water in different pools will merge. The pixel locations at which different pools merge is used to construct separate regions within the image.

In the Reverse Watershed Method, the pixels are treated the same, but the "water" level is initially placed above the tallest "peaks" in the image and then the water is drained, maintaining the same height of water throughout the image. As the water level falls, the most intense pixels will protrude above the water as small islands. These are noted as potential centroids of droplets and the size of each "island" is tracked as the water level falls. This process continues until the water level has fallen to a predetermined threshold. The islands are treated as regions which can be all or part of a single droplet. Due to measurement noise, it is possible for a single droplet to have two or more peaks within it having emerged during the above process. FIG. 1 represents a typical image shown in gray scale. The Reverse Watershed Method can be performed by any suitable means fitting within these parameters. Example 3 below describes an exemplary set of steps by which the Reverse Watershed Method can be performed according to an aspect of the present disclosure.

According to some aspects of the present disclosure, the Reverse Watershed Method can be performed by first determining the standard deviation of the signal within the background of each image and multiplying it by a signal-to-noise-ratio (typically 2.5 to 3.5, however, the signal-to-noise ratio can be adjusted by the user depending on the quantity of noise present in the images) and adding the result to the average intensity of a background pixel. This process can proceed iteratively and an initial estimate of the background cutoff is used to identify probable background pixels (those pixels whose intensity is less than the initial estimate). The intensities of these pixels are in turn used to calculate the average and standard deviation of the intensity of the background pixels. The new average and standard deviation are then used to estimate a new background cutoff. If the new background cutoff is significantly different from the original, then the process is repeated until the original background cutoff and the new background cutoff are in agreement.

Other methods for determining the background cutoff can also be used. In some aspects the user can choose to define a cutoff to identify background pixels and forgo the iterative method described above. In some aspects, the user can choose to identify certain pixels within the image as background pixels and calculate the background and standard deviation from those pixels. In other aspects, the user can calculate the average and standard deviation of pixels in an image taken that has no sample in it (i.e., a dark image). As described below, the average value of the background pixels can be used in analyzing the fluorescence to determine which droplets contain the target molecule.

According to some aspects of the present disclosure, a cutoff threshold is then selected. The cutoff threshold is typically selected at or nearly at the largest pixel intensity of the image. This cutoff threshold is lowered in steps until it reaches a smallest cutoff threshold (SCT). In some aspects, the SCT is equivalent to the background threshold (BT). In other aspects, the SCT can be a different value calculated from the average and standard deviation of the background pixel intensities. In other aspects, the SCT can be a user-defined value. Once the SCT is determined, the user selects the number of steps and the spacing between successive cutoff thresholds. The SCT is chosen to identify pixels that are part of droplets. The BT is chosen to identify pixels that are part of the background. In some aspects the BT can be less than the SCT, in which case, there can be some pixels that are not assigned to either a droplet or the background.

According to some aspects of the present disclosure, imaging analysis software can then be used at each step to find sets of connected pixels (hereafter referred to simply as a "pixel set") in the image above the current step's cutoff threshold. In some aspects the user can require the set of pixels to be either 4-connected or 8-connected. A set of pixels in a square array are considered "4-connected" if each pixel is horizontally or vertically adjacent to at least one other pixel in the set. A set of pixels in a square array are considered "8-connected" if each pixel is horizontally, vertically or diagonally adjacent to at least one other pixel in the set. In some aspects, a different form of connectivity can be used to define connected sets of pixels in the image. In some aspects, a user-defined structuring element can be used to morphologically close the connected sets of pixels determined by the cutoff. If the area of such a pixel set exceeds a user-defined criterion (i.e., a "minimum required area," or "MRA"), then it is marked as a region of interest (ROI). By using a MRA before a given pixel set is accepted as a ROI, it is possible to discriminate against noise in the background pixels. Noise can cause isolated pixels in the background to have an intensity that is larger than a desired SCT. The user-defined MRA can be used to exclude such isolated pixels. The MRA is chosen such that the probability that a given set of connected background pixels having an area larger than the MRA can all have intensities larger than the SCT is small enough that the user is satisfied that the objects found are in fact droplets and not noise in the background. The size of the MRA can be chosen based on the quantity of noise within the droplet area and the area of the smallest droplet in the image that the user wishes to be able to identify.

Once a ROI appears in a particular location of the image, its area can be tracked as the cutoff threshold is decreased. The location of the maximum intensity pixel within each ROI and the values of the pixels within the ROI can also be tracked. The pixel sets that are identified with the SCT are referred to as "Groups." If a Group contains more than one droplet, regions of pixels inside the Group can actually represent space between the droplets. If three or more droplets are contained in a single Group, it is possible that there could be gaps between the droplets that would appear as holes in the interior of the Group. In some aspects a hole-threshold (HT) to identify holes is applied to find possible holes composed of connected pixels inside a single Group. A user-specified minimum size for holes is specified to distinguish holes from noise in the image. Only sets of connected pixels whose areas equal or exceed the minimum size for holes would be marked as holes. In some aspects the HT would equal the SCT. In other aspects, the user can choose a HT which was not equal to the SCT.

The external boundary of a Group is composed of pixels within the group that are adjacent to a pixel that is outside the Group with intensity below the SCT and/or in the Group's interior and adjacent to a pixel in a hole. These pixels are referred to as non-group pixels. The Reverse Watershed procedure then identifies external boundary pixels that are part of the same droplet and a best-fit circle to those external boundary pixels is determined using existing optimization methods.

According to some aspects of the present disclosure, as the cutoff threshold is lowered, two or more ROIs can merge. A pixel set that is above a particular cutoff threshold level can include two or more ROIs that were separate for a larger cutoff threshold. This can happen because either the different ROIs represent different droplets that are so close together that the boundary region between them has a larger pixel intensity than the current cutoff threshold, or the amplitude of noise in the sample is sufficiently large that two or more regions within a single droplet exhibit local maxima. These maxima can appear to the algorithm as separate ROIs at larger cutoff thresholds.

According to further aspects of the present disclosure, a user-defined criteria can be used to decide if different ROIs whose areas are contained within the same pixel set of the current step should (a) be merged and thereafter be treated as one ROI or (b) not be merged and tracked as separate ROIs. These criteria can include, without limitation: (i) the distance between the maximum intensity pixels of the different ROIs, and/or (ii) the values of the maximum intensity pixels of the different ROIs as compared to the smallest intensity pixels that separate them in the pixel set, and/or (iii) the values of the maximum intensity pixels after smoothing of the different ROIs.

For criterion (i) above, a smoothed version of the image can be used instead of the actual image. Smoothing the image can reduce the influence of noise in assessing the distance between the "peaks" of the two ROIs. Additionally, for criterion (i) above, the centroids or another estimator of center of the ROI can also be used. Examples of this include an unweighted centroid where each pixel contributes equal weight to determining the centroid or a weighted centroid where each pixel contributes a weight equal to some function of its intensity to the centroid.

For criterion (ii) above, if the ROIs are parts of separate droplets, it would be expected that they would be separated by a region of pixels that are significantly smaller in intensity than the peaks of the two ROIs. If instead the intensities of the pixels that lay between the two peaks are similar to the intensity of the peaks, then it can be concluded that the two ROIs are in fact part of the same droplet and should be combined. The user-defined criteria can be based on a function that depends on any property of the image that can include: (a) the maximum peak intensity of the ROI, (b) the maximum peak intensity of the ROI after smoothing, (c) the average background intensity, (d) the standard deviation of the background intensities, (e) the cutoff level used to determine the current pixel set or (f) any arbitrary user-specified value.

For criterion (iii) above, in some aspects noise in the image can result in a single pixel containing the maximum intensity of the ROI surrounded by pixels of much smaller intensities. This can be revealed in some cases by smoothing because the maximum pixel intensity of the ROI after smoothing would be significantly lower. If such smoothing reduces the maximum intensities of the two ROIs below a user-defined level, then the two ROIs would be determined to be part of the same droplet and combined. The user-defined level can be a function that depends on any property of the image that can include: (a) the maximum peak intensity of the ROI, (b) the maximum peak intensity of the ROI after smoothing, (c) the average background intensity, (d) the standard deviation of the background intensities, (e) the cutoff level used to determine the current pixel set or (f) any arbitrary user-specified value.

According to certain aspects of the present disclosure, if different ROIs whose areas are contained within the same pixel set of the current step are not merged, then the pixels of that pixel set that were not previously assigned to a ROI must be assigned by one of a few methods, such as the following two possible methods. First, a list of unassigned pixels within the pixel set is sorted by intensity, and the pixel with the largest intensity that is immediately adjacent to one and only one of the ROIs is assigned to that ROI. This process is repeated until the only unassigned pixels remaining are those that are immediately adjacent to two or more different ROIs, in which case, those pixels remain unassigned. Second, the unassigned pixels can be left unassigned until after the last step (i.e., the SCT has been used and the pixel set is then referred to as a Group). In that case, the first method described in this paragraph above is then applied to all the unassigned pixels of the Group.

According to certain aspects of the present disclosure, the result of the procedure to this point can be applied to a droplet image. According to this aspect, the droplet image can be divided into Groups that are separated by pixels whose intensity is below the SCT. Some of the Groups contain only a single ROI and some contain two or more ROIs. The boundary pixels are those pixels belonging to a Group that are adjacent to a non-group pixel.

According to certain aspects of the present disclosure, if a Group consists of only a single ROI, then it is considered to be a single droplet and its boundary pixels are fit to a circle to obtain a droplet diameter.

According to further aspects of the present disclosure, if a Group consists of two or more ROIs, then sets of ROIs (i.e., sets comprising one or more ROIs) from that group are analyzed. The boundary pixels that are part of the set being analyzed are fit to a circle. User-defined criteria are then applied to the best-fit circle to determine whether the ROIs of the set should be combined and considered to be part of a single droplet. This procedure can be applied iteratively, piecing together a droplet one ROI at a time. Possible criteria that can be used to decide which combinations of ROIs to check include, but are not limited to: (i) checking pairs of ROIs that are adjacent to each other (their internal boundaries within the Group are near each other); (ii) checking pairs of ROIs whose best-fit circles have centers that are close to each other; and (iii) checking ROIs whose areas lie substantially inside the best-fit circle of another ROI or set of ROIs. Possible criteria that can be used to determine if two or more ROIs should be combined and classified as a single droplet include, but are not limited to: (i) the quality of the fit (as defined by mean squared error or some other statistical measure of the goodness of a given fit); (ii) how much of the area of the ROIs from the set lie within the best-fit circle; (iii) how much of the area within the best-fit circle consists of pixels in the image background; and (iv) the circularity of the boundary pixels included in the fit.

In another aspect, the above protocol can include additional modifications. Possible modifications to this procedure can include examining the boundary pixels of a Group and not including in any fit those pixels that appear to be noise. An example of a criterion that can be used is that any boundary pixel that is not adjacent to an interior pixel of the Group would not be included in any fit of the boundary to a circle. In this example an interior pixel can be a pixel that is a member of the Group, but that is not a boundary pixel, i.e., is not adjacent to a non-group pixel.

Another possible modification to the above-described Reverse Watershed Method can be that the BT and SCT can be different. A background threshold that is less than the smallest cutoff threshold can be used to eliminate from the set of background pixels those areas that contain objects too faint to be characterized. These areas can contain signal from different focal planes of droplets either above or below the focal plane of the sample being analyzed. A typical example of this occurs when the sample is imaged with fluorescence microscopy. Due to the limitations of the microscope's resolution in the z-direction, fluorescence from one focal plane can bleed through into images of other focal planes.

Other modifications to the Reverse Watershed Method described above are possible according to the present disclosure. Possible modifications to this procedure can include examining the boundary pixels of a Group and not including in any fit those pixels that appear to be noise. An example of a criterion that can be used is, for example, adopting a presumption that any boundary pixel that is not adjacent to an interior pixel of the group would not be included in any fit of the boundary to a circle. According to this assumption, an interior pixel can be a pixel that is a member of the Group, but that is not a boundary pixel, i.e., is not adjacent to a non-group pixel.

In certain aspects, the Reverse Watershed Method can be modified such that the BT and SCT are permitted to be different. A BT that is less than the SCT can be used to eliminate from the set of background pixels those areas that contain objects that are too faint to be characterized. These areas can contain signal from different focal planes of droplets either above or below the focal plane of the sample being analyzed. A typical example of this occurs when the sample is imaged with fluorescence microscopy. Due to the limitations of the microscope's resolution in the z-direction, fluorescence from one focal plane can bleed through into images of other focal planes.

Circle Detection Method. In one aspect of the present disclosure, the Circle Detection Method can be used to analyze droplets in a polydisperse droplet system. According to this method, a threshold (determined as for the Reverse Watershed Method above) is applied to the image. As described in the Reverse Watershed Method, the SCT can be used to identify Groups, however, ROIs are not identified. The hole-threshold can also be applied to identify holes within single Groups as described in the Reverse Watershed Method. After identifying the hole-threshold, the external boundary of each Group can be determined as described in the Reverse Watershed Method. In some aspects, the boundaries of the Groups formed can then be analyzed by the Circle Hough Transform. The Circle Hough Transform is a generalization of the original Hough Transform (i.e., as used to detect lines in images) to detect shapes for which an analytical description exists (in this case circles). According to certain aspects of the present disclosure, the Circle Detection Method analyzes the coordinates of the external boundary pixels (also known as "feature pixels") to find sets of boundary pixels that form all or part of a circle. Identification of the boundary pixels results in a large number of potential circles that are analyzed and only the ones likely to be droplets are retained.

According to this method, circles identified by the Circle Detection Method can be superimposed upon an image, such as is described in Example 5 below. Regions not meeting the criteria set forth in the Circle Detection Method can be discarded. For instance, a circle formed from some or the entire external boundary of one Group cannot include pixels from a different, separate Group. Possible criteria that can then be applied according to this method can include, but are not limited to: (i) selecting potential circles that overlap or lie adjacent to a maxim possible percentage of the group's boundary pixels; (ii) selecting potential circles for which the fraction of its circumference pixels that overlap or lie adjacent to a boundary pixel is as close to one as possible; (iii) rejecting potential circles that have significant amount of their circumference entirely within a group; (iv) rejecting potential circles whose areas include a significant number of non-group pixels; (v) rejecting potential circles whose areas include pixels in a different Group; (vi) for a particular Group, rejecting potential circles whose areas include a significant number of pixels in a hole of that Group; and/or (vii) rejecting potential circles if the best-fit circle for given feature pixels are judged to be of a low quality (i.e., wherein the degree of quality is a user-defined measure of the goodness of a given fit that is statistically calculated and a low quality fit is one in which the fit failed a user-defined criteria).

In certain aspects, there may be overlapping circles at this point. Such pairs would be examined to determine if either should be rejected. Criteria that can be applied to such pairs include, but are not limited to: (i) if the amount of unique area in one of the circles (i.e., the area in one circle that is not in the other) is less than a user-defined fraction of the total area, then one of the circles is removed and (ii) if the number of unique feature pixels (i.e., feature pixels for one circle that are not feature pixels for the other) is less than a user-defined fraction of the total number of feature pixels, then one of the circles is removed. If one circle of a pair is to be removed, then possible criteria used to determine which circle will be removed can include, but are not limited to: (i) removing the circle with the smaller number of feature pixels; (ii) removing the circle with the smallest area; or (iii) removing the circle that contains the larger number of pixels that are not part of the Group (i.e., the largest number that are in the background) or that has the larger fraction of its area not included as part of the Group.

After applying the above criteria, there can still be circles that overlap with each other significantly. Deciding whether to accept such circles as droplets would depend on the nature of the emulsion. In some emulsion systems, it can be common to find droplets pushed together in such a way as to flatten the surfaces in contact, which can have the effect of distorting the droplets (i.e., causing them to take a shape other than strictly spherical). In this instance, the user can decide whether to include or exclude those droplets, depending on the requirements for accuracy in the determination of the size of such droplets. In some systems, small droplets can overlap with much larger droplets. In that case, the circles that describe the smaller droplets can have a significant fraction of their area inside a much larger circle. If enough of the small droplet's boundary is part of its Group's external boundary, the user can choose to accept the small droplet and include it in the analysis. In some aspects, circles can have a significant fraction of their circumference in the interior of a Group. In certain aspects, a user-defined criteria can be used to exclude droplets with more than a specified fraction circles of their boundary in the interior of the Group on the grounds that the circle is an artifact due to noise in the image distorting the exterior boundary of the Group. In some aspects, two possible droplets of similar size have a significant amount of overlap. This can be due to a distortion due to droplets being pushed together as noted above. Or, this can be due to an optical distortion that results in a spherical droplet assuming an elliptical shape in the image. User criteria can be used to mark such circles and exclude them from further analysis.

In some aspects, the user can apply a quality-of-fit test to the droplets and reject those that are deemed not accurately sized. A goodness-of-fit statistic can be calculated for the best fit of a circle to the feature pixels of a droplet and the droplet can be rejected if it failed to meet a user-defined standard. In other aspects, the intensity within the droplet can be examined and the droplet can be rejected if by some measure the overall droplet intensity is too low. One way this can occur is due to the limited resolution of the microscope in the z-direction. Fluorescence from droplets at one position in the z-direction can show up at greatly reduced intensity in images of the sample taken for a different position in the z-direction. A test of overall intensity can be used to identify and reject such faint objects.

In another aspect, the above protocol can include additional modifications. Possible modifications to this procedure can include examining the boundary pixels of a Group and not including in any fit those pixels that appear to be noise. An example of a criterion that can be used is that any boundary pixel that is not adjacent to an interior pixel of the Group would not be included in any fit of the boundary to a circle. In this example, an interior pixel can be a pixel that is a member of the Group, but which is not a boundary pixel, i.e., is not adjacent to a non-group pixel.

Another possible modification to the above-described Circle Detection Method can be that the BT and SCT can be different. A BT that is less than the SCT can be used to eliminate from the set of background pixels those areas that contain objects too faint to be characterized. These areas can contain signal from different focal planes of droplets either above or below the focal plane of the sample being analyzed. A typical example of this occurs when the sample is imaged with fluorescence microscopy. Due to the limitations of the microscope's resolution in the z-direction, fluorescence from one focal plane can bleed through into images of other focal planes.

Other modifications to the Circle Detection Method described above are possible according to the present disclosure. Possible modifications to this procedure can include examining the boundary pixels of a Group and not including in any fit those pixels that appear to be noise. An example of a criterion that can be used is, for example, adopting a presumption that any boundary pixel that is not adjacent to an interior pixel of the Group would not be included in any fit of the boundary to a circle. According to this assumption, an interior pixel can be a pixel that is a member of the Group, but which is not a boundary pixel, i.e., is not adjacent to non-group pixel.

Another possible modification to the Circle Detection Method is that the BT and SCT are permitted to be different. A BT that is less than the SCT can be used to eliminate from the set of background pixels those areas that contain objects that are too faint to be characterized. These areas can contain signal from different focal planes of droplets either above or below the focal plane of the sample being analyzed. A typical example of this occurs when the sample is imaged with fluorescence microscopy. Due to the limitations of the microscope's resolution in the z-direction, fluorescence from one focal plane can bleed through into images of other focal planes.

After sorting the circles, the ones that best define the droplets are used to find which boundary pixels should be used to describe the droplet. These pixels are then fit to a circle to obtain a collection of best-fit circles corresponding to droplets.

In other aspects, the Circle Hough Transform Method can be replaced by a different feature extraction method that would be used to detect circular objects by analyzing the boundary pixels in the image.

Combined Reverse Watershed and Circle Detection Method. In yet another aspect of the present disclosure, aspects of the Reverse Watershed and Circle Detection Methods are combined to yield the Combined Reverse Watershed and Circle Detection Method for the analysis of droplets in a polydisperse droplet system. According to this method, the ROIs and the boundary pixels of Groups (i.e., pixel sets found for the SCT) are determined using the procedure described in the Reverse Watershed Method. Then for each ROI, the Circle Hough Transform is applied to the external boundary pixels of the ROI that are also external boundary pixels of the Group that contains the ROI. The circles for a particular ROI are sorted according to user-determined criteria to find the smallest number of circles that describe the boundary of that ROI. In most cases there will be one circle per ROI. Possible criteria that can be used include, but are not limited to: (i) selecting circles that include the largest fraction of the ROI's external boundary pixels; (ii) selecting circles that include the largest fraction of the ROI's area; (iii) rejecting circles that include pixels from a different Group; (iv) rejecting circles that include a substantial number of non-group pixels; (v) discriminating against circles that have a substantial fraction of their circumference in the interior of the Group.

According to certain aspects of the present disclosure, the initial set of circles for a ROI can be examined in pairs, with one of the two circles being rejected in favor of the other. Possible criteria that can be used here include, but are not limited to: (i) if the centers of two circles of the same or similar size are in close proximity to one another, then rejecting the circle with the smaller number of votes or (ii) if two circles have more than a user-defined fraction of their votes in common, then rejecting the circle with the smaller number of votes. For example if a possible Hough Transform circle includes external boundary pixels from a particular ROI, then the circle would be rejected unless it encompassed at least some user-defined fraction of that ROI's area. In this case, the minimum required fraction can depend on how many boundary pixels of the ROI are associated with the Hough Transform circle.

Also, in cases where there are multiple droplets in close proximity to one another, the intensities of pixels that are close to two or more droplets, but not actually part of any of the droplets, can have an elevated intensity relative to the background and can be included as part of the Group and form part of the external Group boundary. In the Reverse Watershed method, this can lead to difficulties, since the additional pixels included in the Group will cause portions of the external boundary to be non-circular. The inclusion of external boundary pixels that are not actually part of the droplet can result in a best-fit circle that is a less accurate description of the droplet. The problem of the region between two droplets having elevated pixel intensities leading to a non-circular boundary can be mitigated by the use of the Circle Hough Transform, since it discriminates against including pixels in the fit that would form a non-circular boundary.

The circle or circles associated with an ROI are estimates of the size of the droplet the ROI can be a part of. This information is used to group the ROIs into droplets. For example, if the circles associated with two ROIs in the same Group have similar radii and have centers that are close together, then the two ROIs will be considered to be part of the same droplet. User-defined criteria would be used to decide how similar the radii of the circles must be and how close the centers of the circles must be in order for the two ROIs to be combined into one droplet. The criterion relating to how close the centers must be can depend on the size of the two circles.

It is possible that an ROI can be assigned to two or more droplets, or considered for assignment to two or more droplets. In some aspects, possible criteria to determine which droplet the ROI should be assigned to include, but is not limited to: (i) calculating a goodness of fit statistic to the feature pixels of just the ROI being considered using the parameters the best-fit circle for each of the droplets and assigning the ROI to the droplet whose circle is the best fit to the feature pixels of the ROI or (ii) assigning the ROI to the droplet with which it has the largest overlap in area.

In some aspects, after all the ROIs with circles are assigned to droplets, any remaining external boundary pixels that are not part of any circle are checked to see if they lie within a user-defined distance of the boundary of an existing circle. If so those external boundary pixels are included in the boundary of the droplet. Unassigned external boundary pixels that still lie on a droplet's boundary can occur if the external boundary of a ROI is distorted by noise such that the Circle Hough Transform finds no acceptable circles for that ROI. Then the external boundary pixels for each droplet are fit to a circle to obtain a size and a position. Droplets that overlap significantly can be accepted or discarded depending on user-defined criteria for the amount of such overlap that is allowed and that can depend on the properties of the emulsion. Droplets that appear to have a significant fraction of its boundary in the interior of a group can be accepted or discarded depending on user-defined criteria. In addition, if the user is willing to accept slightly distorted droplets, the Hough Transform can be used to detect ellipses in the image, and those ellipses that satisfy a user-set criterion (such as having an aspect ratio less than a user selected limit) can be accepted as droplets.

This method can include additional modifications. Possible modifications to this procedure can include examining the boundary pixels of a Group and not including in any fit those pixels that appear to be noise. An example of a criterion that can be used is that any boundary pixel that is not adjacent to an interior pixel of the Group would not be included in any fit of the boundary to a circle. In this example an interior pixel can be a pixel that is a member of the Group, but which is not a boundary pixel, i.e., is not adjacent to a non-group pixel.

Another possible modification to the above-described Combined Reverse Watershed and Circle Detection Method can be that the BT and SCT can be different. A BT that is less than the SCT can be used to eliminate from the set of background pixels those areas that contain objects too faint to be identified. These areas can contain signal from different focal planes of droplets either above or below the focal plane of the sample being analyzed. A typical example of this occurs when the sample is imaged with fluorescence microscopy. Due to the limitations of the microscope's resolution in the z-direction, fluorescence from one focal plane can bleed through into images of other focal planes.

Other modifications to the Combined Reverse Watershed and Circle Detection Method described above are possible according to the present disclosure. Possible modifications to this procedure can include examining the boundary pixels of a Group and not including in any fit those pixels that appear to be noise. An example of a criterion that can be used is, for example, adopting a presumption that any boundary pixel that is not adjacent to an interior pixel of the Group would not be included in any fit of the boundary to a circle. According to this assumption, an interior pixel can be a pixel that is a member of the Group, but which is not a boundary pixel, i.e., is not adjacent to a non-group pixel.

Another possible modification is that the BT and SCT are permitted to be different. A BT that is less than the SCT can be used to eliminate from the set of background pixels those areas that contain objects that are too faint to be characterized. These areas can contain signal from different focal planes of droplets either above or below the focal plane of the sample being analyzed. A typical example of this occurs when the sample is imaged with fluorescence microscopy. Due to the limitations of the microscope's resolution in the z-direction, fluorescence from one focal plane can bleed through into images of other focal planes.

In another aspect, the Circle Hough Transform can be replaced by a different feature extraction method that identifies circles. In that case the information produced by the alternate feature extraction method would be used to identify droplets.

In yet another aspect, this method can be used to search for non-circular objects in an image. The Circle Hough Transform would be replaced by a feature extraction method that identifies objects of the desired shape.

Determination of Occupancy. In some aspects, after the droplets have been identified and their size determined, the fluorescence intensity is used to determine if the droplet contained the target molecule.

In some aspects, the presence of the target molecule would result in an increase of the fluorescence from the droplet. In those cases, an intensity cutoff standard can be imposed wherein a droplet whose intensity exceeds the cutoff is considered to be occupied and the remainder would be considered empty. In systems where the presence of the target molecule results in a decrease of fluorescence, droplets whose intensities exceed the cutoff are considered to be empty and the others would be considered occupied. In both cases, the intensity of a droplet being compared to the cutoff can be: (i) the average intensity within the droplet; (ii) the peak intensity within the droplet or (iii) any user-chosen function of the intensities of the pixels within the droplet (for example the median intensity or a percentile of the intensities can be used).

In some aspects the method for determining occupancy would use two fluorescence images of each droplet. In one of the images the intensity of the fluorescence would depend measurably on whether the droplet was occupied. In the other image, the intensity of the fluorescence would be unchanged or little changed by the presence of the target molecule. A function of the intensities of the droplet from the two images such as the ratio can be used to decide the occupancy of the droplet. Using a ratio or some other function instead of the intensity from a single image can correct for the possible instrumental artifacts. Furthermore, for larger droplets, fluorescence from focal planes in the sample above the plane being imaged can appear in the image causing an increase in the measured intensities of the pixels within that droplet. Using the intensities of a droplet from two different images would allow the user to avoid these problems. The intensities of a droplet being analyzed can be: (i) the average intensity within the droplet; (ii) the peak intensity within the droplet or (iii) any user-chosen function of the intensities of the pixels within the droplet (for example the median intensity or a percentile of the intensities can be used). The intensities can, at the user's discretion, be background subtracted. In some aspects, the average background used to identify the Groups is subtracted from the intensity of each pixel in the image.

In some aspects, a corrected set of background pixels is determined at this stage. One method for determining the corrected set is to start with the set of pixels that are inside the Groups (that may include pixels in holes interior to the Groups). At the user's discretion, these sets of pixels can be dilated (i.e., enlarged) by one or more pixels. The pixels that were not included in these sets of pixels would form the set of corrected background pixels.

Figure 2A:
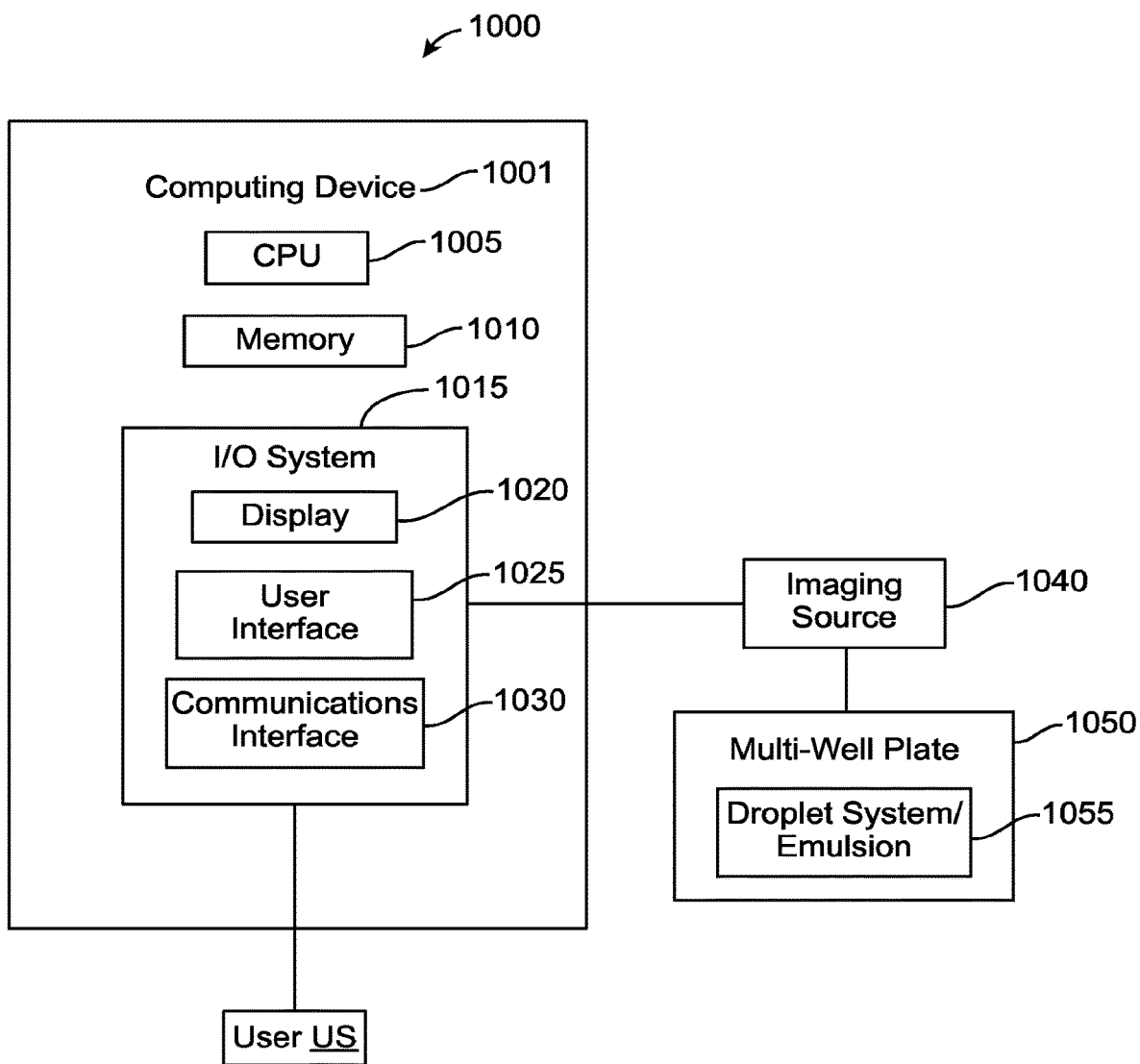
FIG. 2A schematically illustrates an exemplary detection system configured to analyze the presence or absence of sample in a plurality of droplets.

Exemplary Analysis System and Methods. As discussed herein, the present disclosure includes detection systems configured to analyze the volumes and the presence or absence of sample in the plurality of droplets of an emulsion system. FIG. 2A schematically illustrates an exemplary detection system 1000. The detection system may comprise a computing device 1001 configured to be operated by a user US, an imaging source 1040 configured to be operated by the computing device 1001, and a multi-well plate 1050 configured to be imaged by the imaging platform or source 1040 and which may contain a droplet system or emulsion system 1055 to be imaged and analyzed.

The computing device 1001 may be programmed to implement one or more of the methods described herein. The computing device 1001 may comprise a personal computer, a workstation, or a server, for example. The computing device 1001 includes a processor, computer processor, central processing unit, or CPU 1005, which can be a single core or multi-core processor, or a plurality of processors for parallel processing.

The computing device 1001 may also include a memory 1010 (e.g., random-access memory, read-only memory, flash memory, a hard disk, or the like). The memory 1010 can store files, such as computer readable image files taken by the imaging source 1040. The computing device 1001 in some cases can include one or more additional data storage units that are external to the computing device 1001, such as located on a remote server that is in communication with the computing device 1001 through the one or more networks.

The computing device 1001 may further comprise an input/output or I/O system 1015 which can be used by the computing device 1001 to communicate with one or more of the user US, one or more other computing devices or systems, one or more networks (e.g., a local area network (LAN), an extranet, an intranet, the Internet, a telecommunications network, a data network, a cellular data network, or the like), or one or more peripheral devices including the imaging source 1040, external memory, various adapters, etc. The I/O system 1015 may comprise a display 1020, a user interface 1025, and a communications interface 1030. The display 1020 may comprise a touch screen display through which the user interface 1025 is projected to the user US, for example. The communications interface 1030 may comprise a network adaptor for the computing device 1001 to connect to the one or more networks. The user US, for example, may operate the computing device 1001 through the one or more networks remotely. For instance, the computing device 1001 may comprise a computing system based in the cloud such a distributed computing system which operates the imaging source 1040 which may be local to the user US. The computing device 1001 can be in communication with the imaging source 1040 through the one or more networks or by direct communication.

Methods as described herein can be implemented by way of machine (or computer processor) executable code (or software) stored on an electronic storage location of the computing device 1001, such as, for example, on the memory 1010 or other electronic storage unit. During use, the code can be executed by the processor 1005. In some cases, the code can be retrieved from the storage unit and stored on the memory 1010 for ready access by the processor 1005. In some situations, the electronic storage unit can be precluded, and machine-executable instructions are stored on memory 1010. Alternatively, the code can be executed on a remote computer system. The code executed may operate the imaging source 1040 to image and analyze the multi-well plate 1050 in accordance with any of the methods described herein. The code may be executed automatically by the computing device 1001 or may be executed in accordance with instructions provided by an operator such as the user US.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computing device 1001, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The results of methods of the disclosure can be displayed to a user on the user interface or UI 1025 or other user interface, which may include a graphical user interface (GUI), of an electronic device of the user US or other operator. The other UI, such as GUI, can be provided on a display of an electronic device of the user such as a tablet computer, a smartphone, a wearable computer, or the like. The display can be a capacitive or resistive touch display, for example. Such displays can be used with other systems and methods of the disclosure.

The imaging source 1040 may comprise any of the imaging devices and sources described herein. The imaging source 1040 may comprise, for example, an optical imaging source. The imaging source 1040 may be configured to perform one or more of confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epiflouorescent microscopy, bright field imaging, dark field imaging, oblique illumination, or a combination thereof.

The multi-well plate 1050 may comprise any multi-well plate known in the art. The droplet system or emulsion system 1055 may be generated by any of the methods described herein.

Figure 2B:
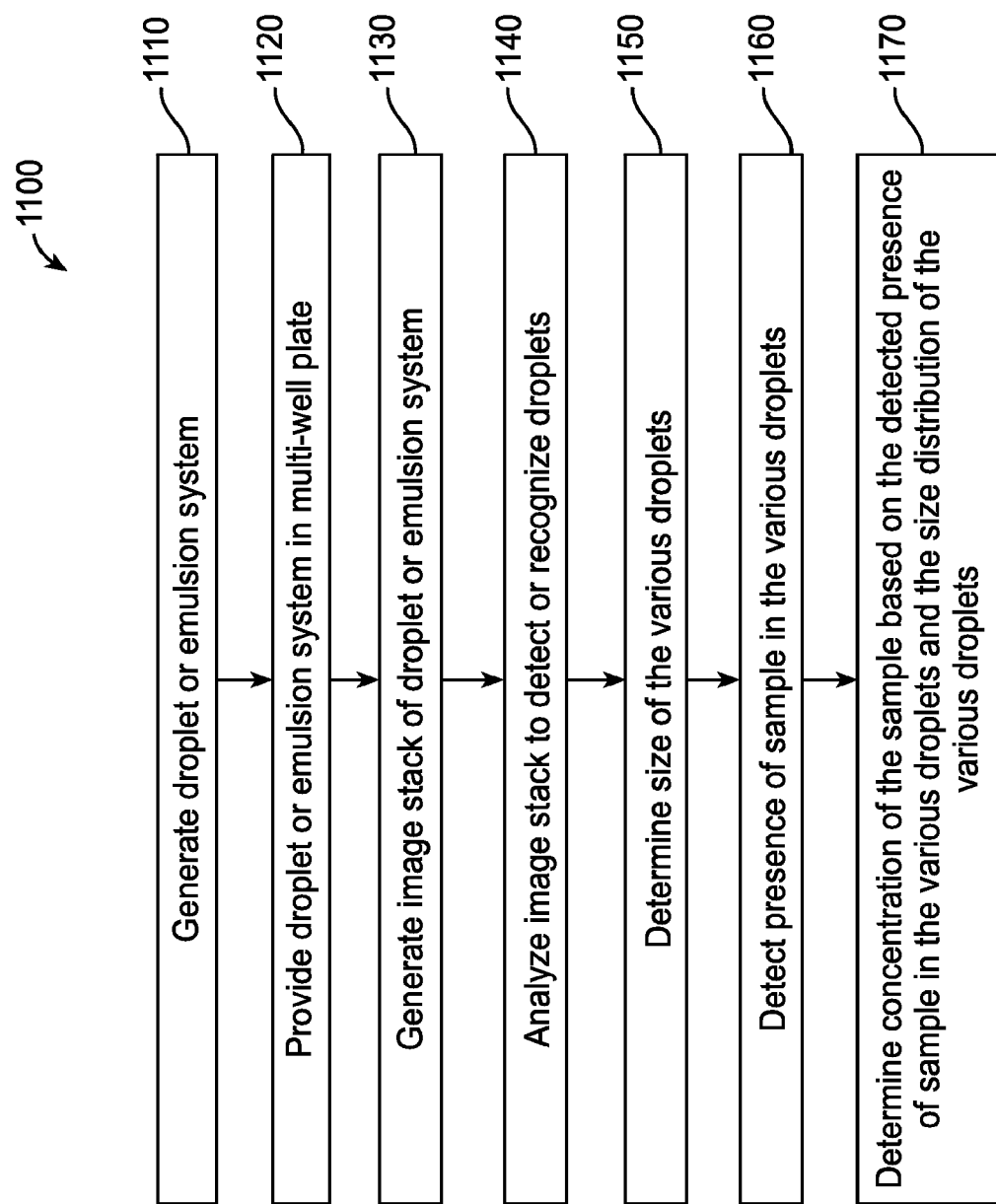
FIG. 2B schematically illustrates an exemplary detection method to analyze the presence and or absence of sample in a plurality of droplets.

The exemplary detection system 1000 may be operated by the user US to implement any of the methods described herein. For example, the detection system 1000 may be operated by the user US to implement an exemplary detection method 1100 schematically illustrated in FIG. 2B or an exemplary detection method 100 schematically illustrated in FIG. 2C. The detection method 1100 of FIG. 2B may comprise various steps as follows. In a step 1110, a droplet or emulsion system may be generated. The droplet or emulsion system may be generated in the many ways as described herein such as by shaking, vortexing, or other agitation. In a step 1120, the droplet or emulsion system may be provided on a multi-well plate in many ways as described herein. In a step 1130, an image stack of the droplet or emulsion system may be generated in the many ways as described herein. In a step 1140, the image stack may be analyzed to detect or recognize droplets in the many ways as described herein. For example, one or more of the Line Scan Method, the Simple Boundary Method, the Reverse Watershed Method, the Circle Detection Method, the Combined Reverse Watershed and Circle Detection Method, or combinations thereof may be used to detect or recognize the droplets. In a step 1150, the presence of sample may be detected in the various droplets (i.e., occupancy may be determined) in the many ways as described herein. In a step 1170, the concentration of the sample may be determined based on the detected presence of the sample in the various droplets and the size distribution of the various droplets in the many ways as described herein (e.g., with the statistical methods described herein).

Figure 2C:
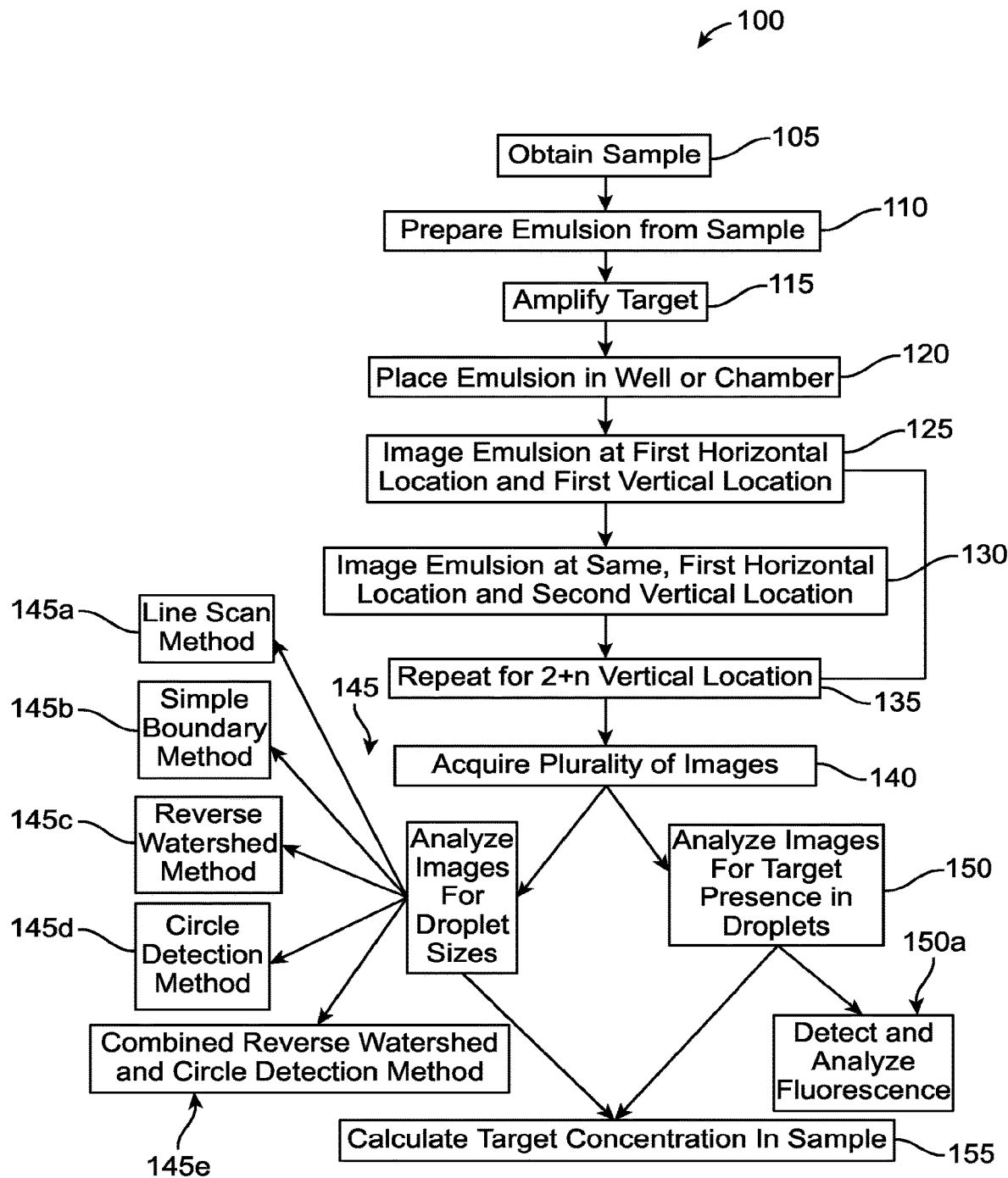
FIG. 2C schematically illustrates another exemplary detection method to analyze the presence and or absence of sample in a plurality of droplets.

The detection method 100 of FIG. 2C may comprise various steps as follows. In a step 105, a sample may be obtained. The sample may be obtained in any of the ways described herein. In a step 110, an emulsion is prepared from the sample. The emulsion may be prepared in any of the ways described herein. In a step 115, the target may be amplified. The target may be amplified in any of the ways described herein. In a step 120, the emulsion is placed in a well or chamber. In some embodiments, the steps 110 and 120 may occur concurrently and the emulsion may be prepared in the well or chamber. In a step 125, the emulsion may be imaged at a first horizontal location and a first vertical location. In a step 130, the emulsion may be imaged at the same, first horizontal location and a second vertical location different from the first vertical location. In a step 135, the imaging steps may be repeated for 2+n vertical locations. In a step 140, a plurality of images may be acquired such as by performing the previous steps 125, 130, and 135. In a step 145, the acquired images are analyzed for droplet sizes. The acquired images may be analyzed in any of the ways described herein. For example, the acquired images may be analyzed by one or more of using a Line Scan Method in a step 145a, using a Simple Boundary Method in a step 145b, using a Reverse Watershed Method in a step 145c, using a Circle Detection Method in a step 145d, using a Combined Reverse Watershed and Circle Detection Method in a step 145e, or using a combination of two or more of the aforementioned. A droplet may appear in more than one image of a Z-stack. In this case, the information in those images may be combined by methods described herein above to determine the diameter of that droplet. In a step 150, the acquired images may be analyzed for the presence of the target in the droplets. The analysis for the presence of the target may be performed in any of the ways described herein. The step 150 may, for example, comprise a step 150a of detecting and analyzing for fluorescence. The step 150 may occur after the images are analyzed for droplet sizes in the step 145 or may occur as a parallel step to step 145. The step 150 may include a step 150a of detecting and analyzing for fluorescence. In a step 155, the target concentration in the sample may be calculated. The target concentration in the sample may be calculated in any of the ways described herein. For example the calculation may be based on the image analysis for droplet size from the step 145 and the image analysis for the target presence in the droplets from the step 150.

Although the above steps show the methods 1100 and 100 for target detection in accordance with many aspects and embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial.

One or more of the steps or sub-steps of the methods 1100 and 100 may be performed with processing elements or circuitry as described here, for example one or more of the processor or CPU 1005 of the computing device 1001 of the system 1000 described herein. Instructions for the CPU 1005 may be stored on the memory 1010 of the system 1000. These instructions, when executed by the CPU 1005, may perform one or more of the steps or sub-steps of the methods 1100 and 100.

In various aspects, the disclosure provides many methods for detecting or recognizing droplets such as the Line Scan Method, the Simple Boundary Method, the Reverse Watershed Method, the Circle Detection Method, the Combined Reverse Watershed and Circle Detection Method, or combinations thereof described herein. In some aspects, the methods of detecting or recognizing the droplets may be independent of the methods to determine sample concentration. That is, the methods of detecting or recognizing the droplets may be used for many purposes other than performing digital assay described herein.

FIGS. 2D, 2E, 2F, 2G, and 2H schematically illustrates exemplary droplet recognition methods 1200, 1300, 1400, 1500, and 1600, respectively. The step 1140 may apply one or more of the methods 1200, 1300, 1400, 1500, and 1600 to analyze an image stack to detect or recognize droplets, for example.

Figure 2D:
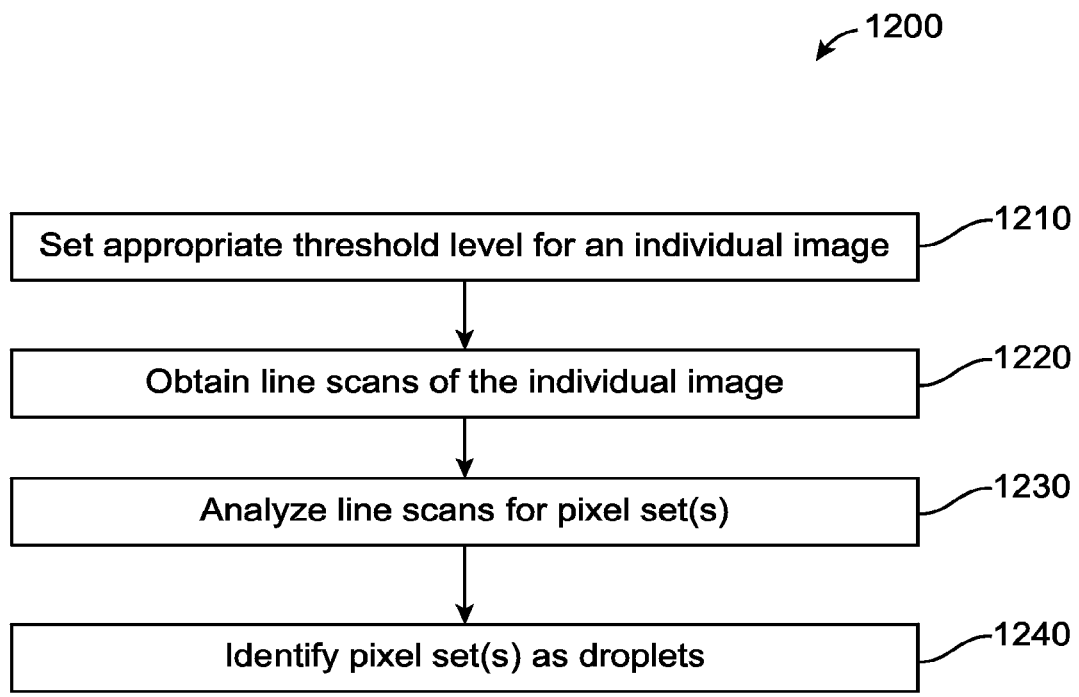
FIG. 2D schematically illustrates an exemplary scan detection method to identify droplets in a volume, which may be used with the system of FIG. 2A to implement the methods of FIGS. 2B and 2A.
Figure 2E:
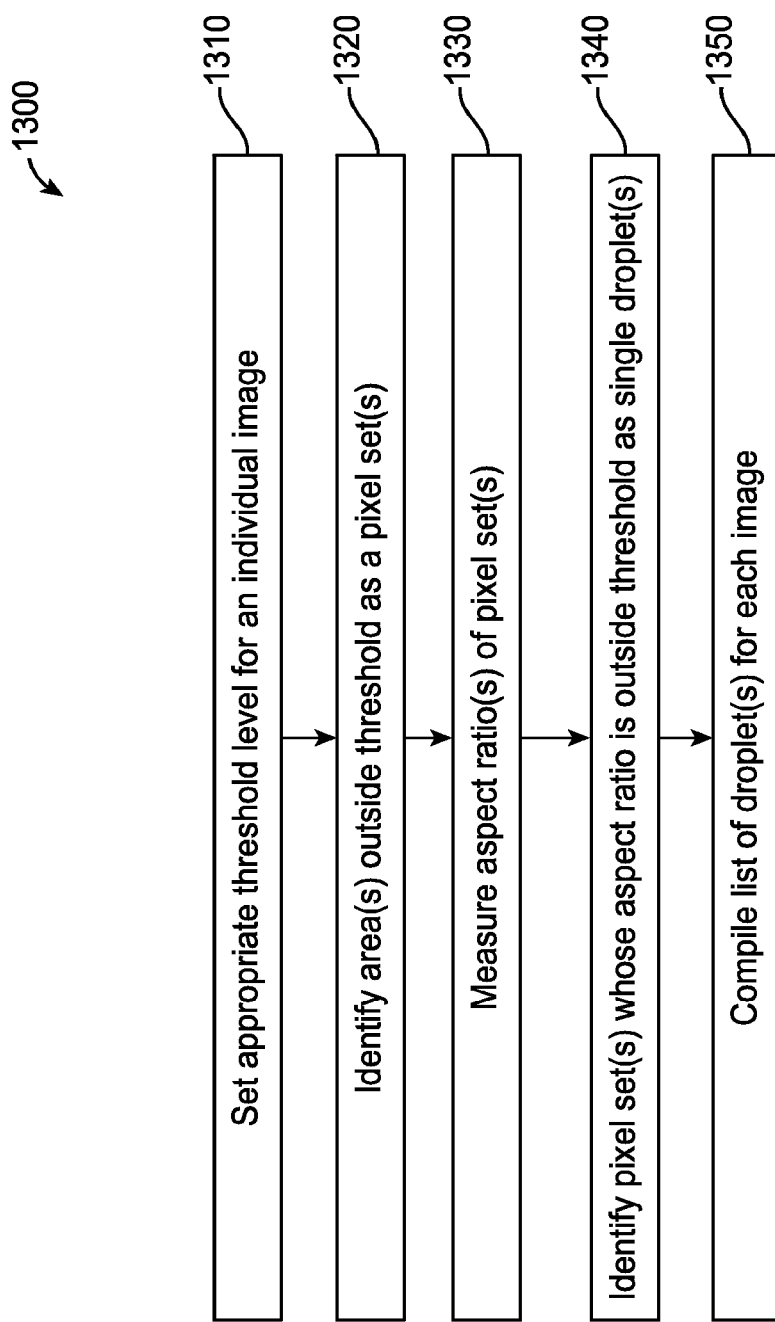
FIG. 2E schematically illustrates an exemplary Simple Boundary Method to identify droplets in a volume, which may be used with the system of FIG. 2A to implement the methods of FIGS. 2B and 2A.

As shown in FIG. 2D, the droplet recognition method 1200 may be similar to or comprise the Line Scan Method described above and may comprise various steps as follows. In a step 1210, an appropriate threshold level for an individual image may be set. The appropriate threshold level may be a pixel intensity threshold for example. In a step 1220, line scans may be obtained within the image. In a step 1230, the line scans may be analyzed for pixel sets. These pixel sets may comprise, for example, segments of the line scans which are at or outside the set threshold level (e.g., above or below) and which are contiguous between adjacent line scans. In a step 1240, droplets may be identified from the pixel sets. For example, the longest segment of a line scan for a pixel set can be regarded as the diameter of a droplet and the size of the droplet can be calculated from the diameter. While line scans are generally discussed herein, other methods of generating scans are also contemplated. These methods may include confocal scanning, line illumination and collection, Nipkow disc type scanning, or the like As shown in FIG. 2E, the droplet recognition method 1300 may be similar to or may comprise the Simple Boundary Method described above and may comprise various steps as follows. In a step 1310, an appropriate threshold level is set for an individual image. In a step 1320, areas at or outside the threshold level (e.g., above or below) may be identified as a pixel set(s). In a step 1330, the aspect ratios of the pixel set(s) may be measured. In a step 1340, pixels set(s) whose aspect ratio is outside (e.g., generally below but may be above alternatively) a threshold aspect ratio are identified as single droplets. The threshold aspect ratio may be 1, 1.1, 1.2, 1.3, 1.4, 1.5, 1.6, 1.7, 1.8, 1.9, or 2.0, for example. In a step 1350, a list of droplet(s) for each image can be compiled.

Figure 2F:
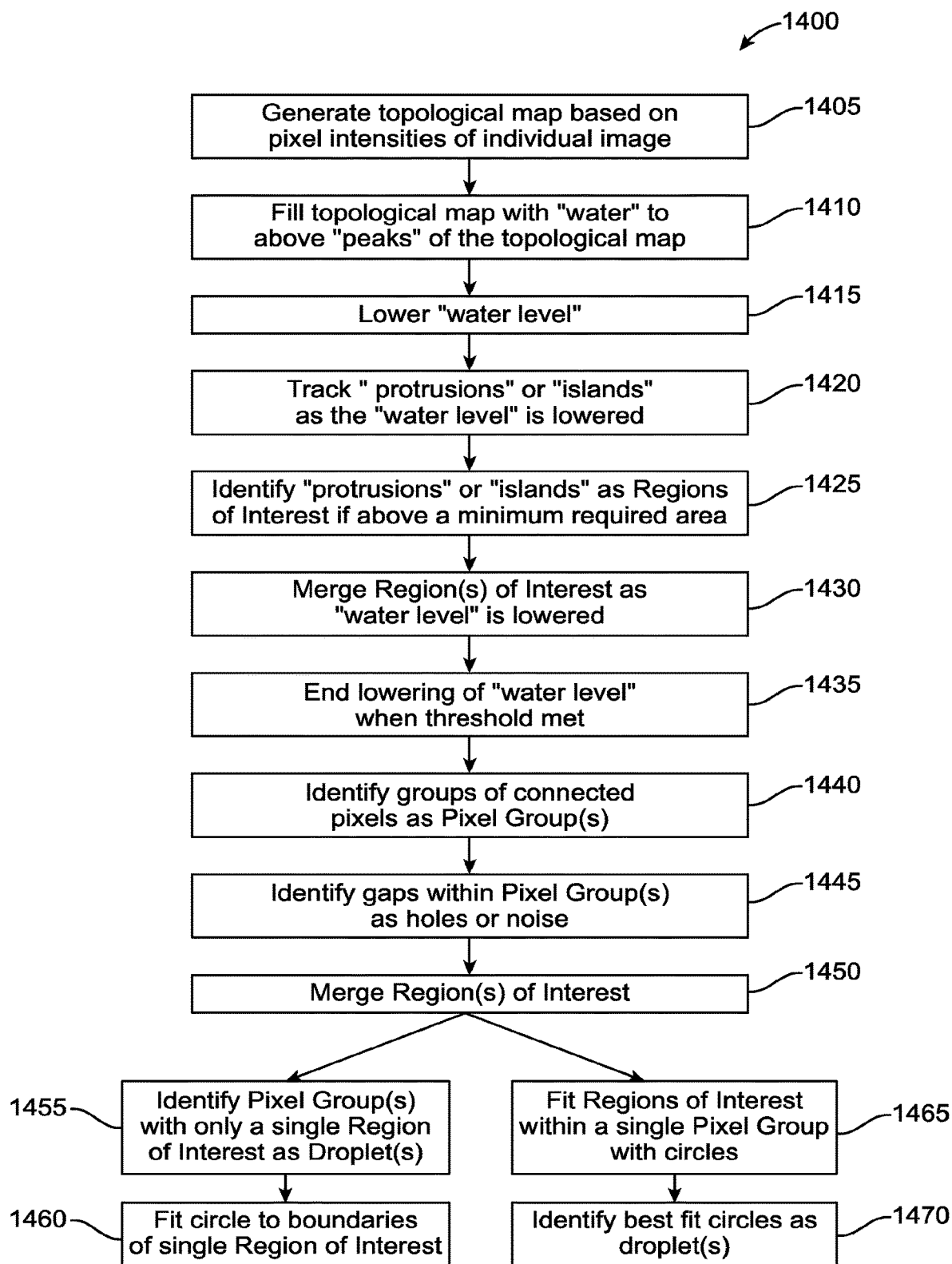
FIG. 2F schematically illustrates an exemplary Reverse Watershed Method to identify droplets in a volume, which may be used with the system of FIG. 2A to implement the methods of FIGS. 2B and 2A.

As shown in FIG. 2F, the droplet recognition method 1400 may be similar to or may comprise the Reverse Watershed Method described above and may comprise various steps as follows. In a step 1405, a 3D topological map based on the pixel intensities of an individual image may be generated. In a step 1410, the topological map may be filled with "water" (i.e., a computerized, synthetic representation of water or other fluid) to above the "peaks" of topological map. The topological map can be filled with "water" in many ways as described herein above. For example, the standard deviation of the signal within the background of each image can be determined, multiplied with a signal-to-noise ratio, and then added to the average intensity of a background pixel. In a step 1415, the "water level" may be lowered. The "water level" of the topological map may be lowered in many ways described herein above. For example, a maximum pixel intensity cutoff threshold may be established and lowered until it reaches the background pixel intensity threshold. In a step 1420, "protrusions" or "islands" (i.e., highest intensity pixels) may be tracked as the "water level: is lowered. In a step 1425, such "protrusions" or "islands" may be identified as Region(s) of Interest if they satisfy a user defined criteria such as a minimum required area. The user-defined criterion may be defined in many ways as described herein above. In a step 1430, the Region(s) of Interest may be merged as the "water level" is lowered depending if certain criteria, for example as described herein above, are met. As described herein above, the image may be smoothed prior to making the determination of whether to merge two or more Regions of Interest. In a step 1435, the lowering of the "water level" may end when a threshold is met. The threshold may comprise a background intensity threshold or cutoff as described herein and may be determined in many ways as described herein above.

In a step 1440, group(s) of connected pixels may be identified as Pixel Group(s). Such identification can be made in many ways as described herein above. In a step 1445, gaps within the Pixel Group(s) may be identified as holes or noise, such as by applying a hole threshold as described herein above. The holes may comprise gaps between droplets, for example. In a step 1450, the Region(s) of Interest may be merged as the "water level" is lowered or after the lowering of the "water level" is ended depending if certain criteria, for example as described herein above, are met. As described herein above, the image may be smoothed prior to making the determination of whether to merge two or more Regions of Interest.

In a step 1455, a Pixel Group comprising only a single Region of Interest may be identified as a droplet. In a step 1460, a circle may be fit to the boundaries of the single Region of Interest. The circle may be analyzed to obtain a droplet diameter as described herein above. Pixel Groups having multiple Regions of Interest may be identified in accordance with the methods described herein above to identify most probably droplets. In a step 1465, the Regions of Interest within a single Pixel Group may be fit with circles. In a step 1470, the best fit circles may be identified as droplets. The best fit circles may be analyzed to obtain droplet diameters as described herein above.

Figure 2G:
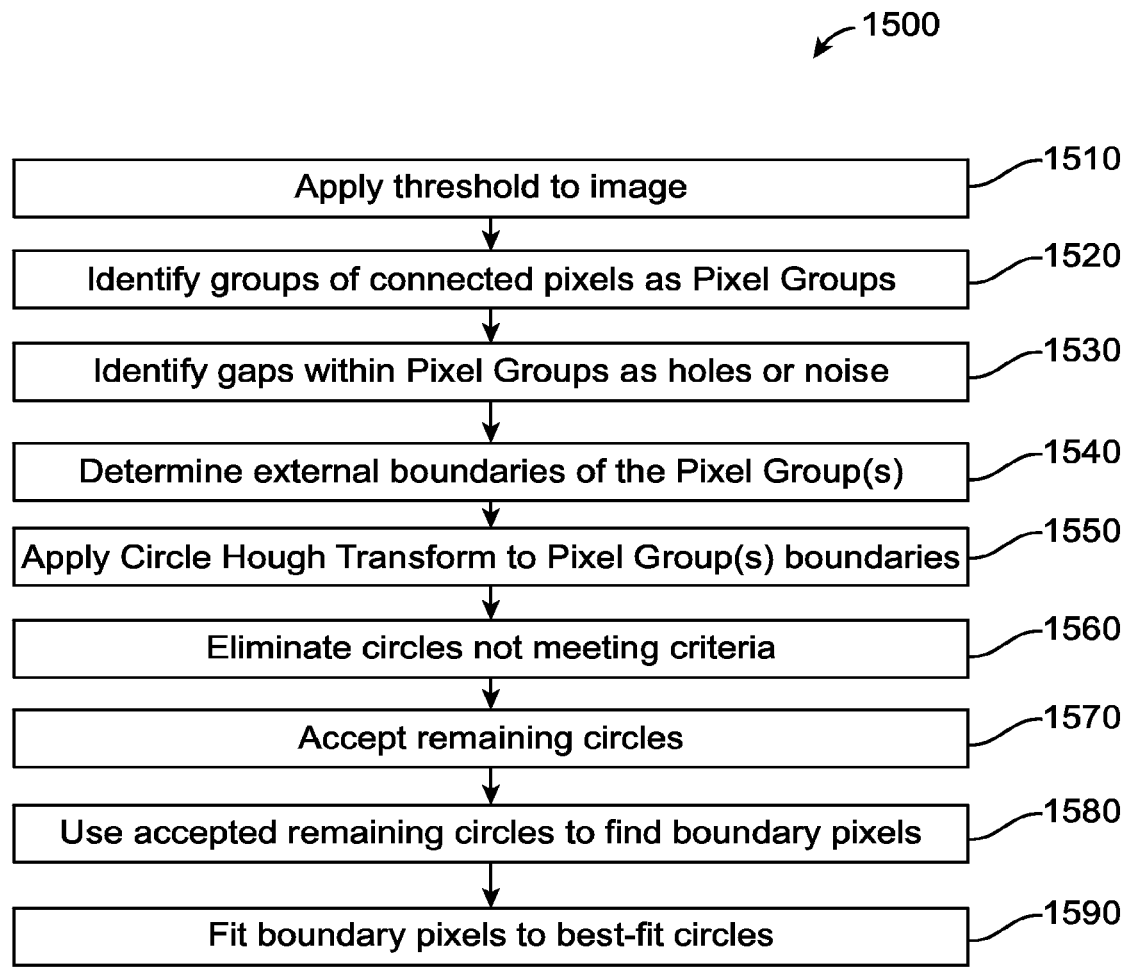
FIG. 2G schematically illustrates an exemplary Circle Detection Method to identify droplets in a volume, which may be used with the system of FIG. 2A to implement the methods of FIGS. 2B and 2A.

As shown in FIG. 2G, the droplet recognition method 1500 may be similar to or may comprise the Circle Detection Method described above and may comprise various steps as follows. In a step 1510, a threshold may be applied to an individual image. The threshold may be determined as in the Reverse Watershed Method described herein above. In a step 1520, groups of connected pixels may be identified as Pixel Groups. Such identification may be made as in the Reverse Watershed Method described herein above. In a step 1530, gaps within the Pixel Group(s) may be identified as holes or noise such as by applying a hole threshold as described herein above. In a step 1540, the external boundaries of the Pixel Group(s) may be determined. In a step 1550, the Circle Hough Transform is applied to the boundaries of the Pixel Group(s). In a step 1560, circles not meeting certain criteria may be eliminated. The criteria may be any of the criteria described herein above. In a step 1570, one or more of the remaining circles may be accepted. Criteria may be applied as described herein above to determine whether to accept the remaining circle(s). In a step 1580, the accepted remaining circles are used to find the best boundary pixels for a droplet. In a step 1590, the boundary pixels are fit to a circle to obtain a collection of best-fit circles corresponding to the droplet(s). These best fit circles may be used to determine the diameters and sizes of the droplet(s).

Figure 2H:
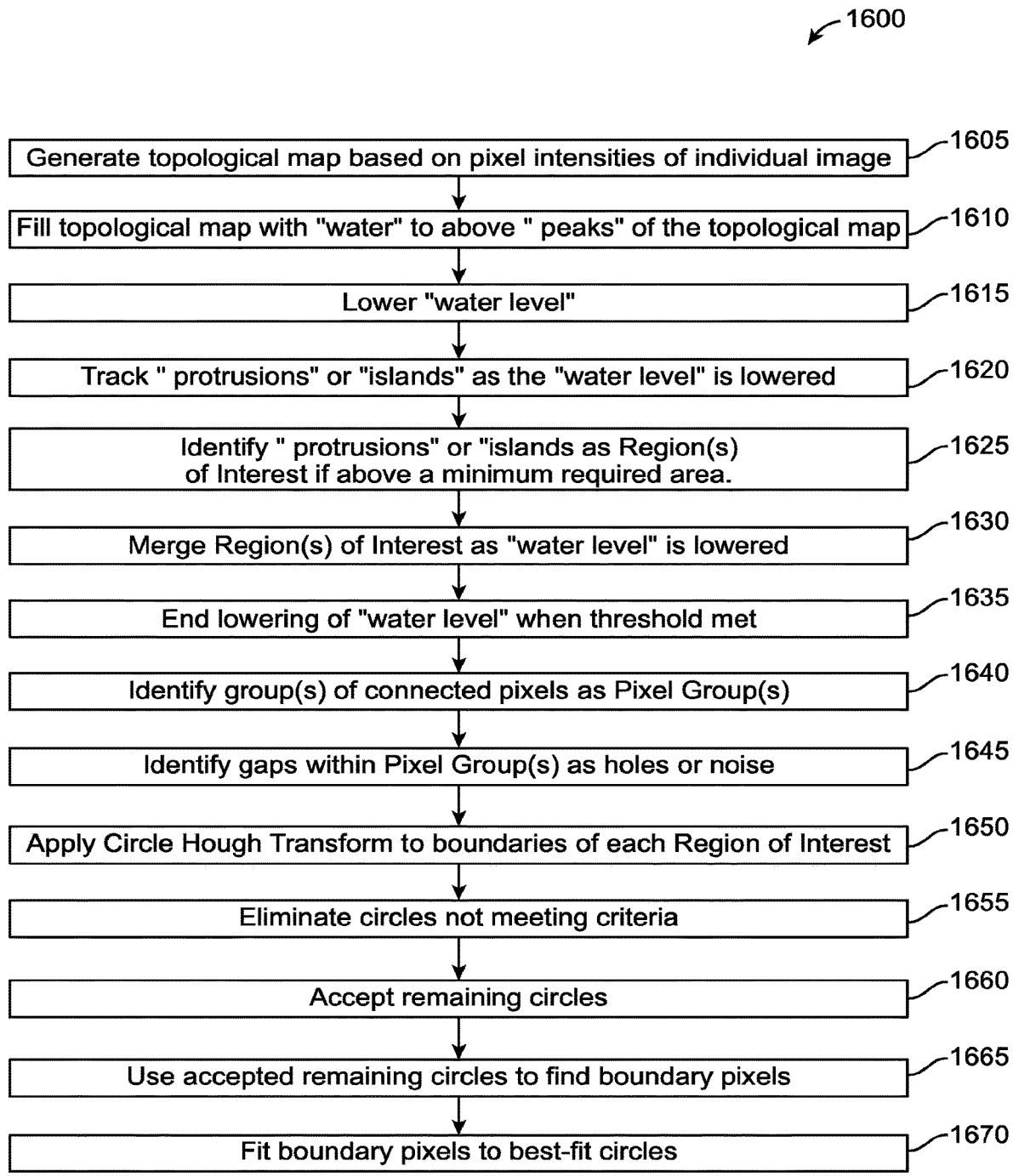
FIG. 2H schematically illustrates an exemplary combined reverse watershed and Circle Detection Method to identify droplets in a volume, which may be used with the system of FIG. 2A to implement the methods of FIGS. 2B and 2A.

As shown in FIG. 2H, the droplet recognition method 1600 may be similar to or may comprise the Combined Reverse Watershed and Circle Detection Method described above and may comprise various steps as follows. The steps 1605, 1610, 1615, 1620, 1625, 1630, 1635, 1640, and 1645 may be similar to the steps 1405, 1410, 1415, 1420, 1425, 1430, 1435, 1440, and 1445, respectively of the Reverse Watershed method 1400 described above. In a step 1605, a 3D topological map based on the pixel intensities of an individual image may be generated. In a step 1610, the topological map is filled with "water" (i.e., a computerized, synthetic representation of water or other fluid) to above the "peaks" of topological map. The topological map can be filled with "water" in many ways as described herein above. For example, the standard deviation of the signal within the background of each image can be determined, multiplied with a signal-to-noise ratio, and then added to the average intensity of a background pixel. In a step 1615, the "water level" may be lowered. The "water level" of the topological map may be lowered in many ways described herein above. For example, a maximum pixel intensity cutoff threshold may be established and lowered until it reaches the background pixel intensity threshold. In a step 1620, "protrusions" or "islands" (i.e., highest intensity pixels) may be tracked as the "water level: is lowered. In a step 1625, such "protrusions" or "islands" may be identified as Region(s) of Interest if they satisfy a user defined criteria such as a minimum required area. The user-defined criterion may be defined in many ways as described herein above. In a step 1630, the Region(s) of Interest may be merged as the "water level" is lowered depending if certain criteria, for example as described herein above, are met. As described herein above, the image may be smoothed prior to making the determination of whether to merge two or more Regions of Interest. In a step 1635, the lowering of the "water level" may end when a threshold is met. The threshold may comprise a background intensity threshold or cutoff as described herein and may be determined in many ways as described herein above. In a step 1640, group(s) of connected pixels may be identified as Pixel Group(s). Such identification can be made in many ways as described herein above. In a step 1645, gaps within the Region(s) of Interest are identified as holes or noise, such as by applying a hole threshold as described herein above. In a step 1650, the Circle Hough Transform is applied to the boundaries of each Region of Interest.

The steps 1655, 1660, 1670, and 1675 may be similar to the steps 1560, 1570, 1580, and 1590, respectively, above. In a step 1655, circles not meeting certain criteria may be eliminated. The criteria may be any of the criteria described herein above. In a step 1660, the remaining circles may be accepted. In a step 1665, the accepted remaining circles may be used to find the best boundary pixels for a droplet. In a step 1670, the boundary pixels are fit to best-fit circles. These best fit circles may be used to determine the diameters and sizes of the droplet(s).

Although the above steps show the methods 1100, 1200, 1300, 1400, 1500, and 1600 of detecting droplets and/or analyzing droplet or emulsion systems in accordance with various aspects of the disclosure, a person of ordinary skill in the art will recognize many variations based on the teaching described herein. The steps may be completed in a different order. Steps may be added or deleted. Some of the steps may comprise sub-steps. Many of the steps may be repeated as often as beneficial.

One or more of the steps of the methods 1100, 1200, 1300, 1400, 1500, and 1600 may be performed with the computing system 1000 as described herein. Alternatively or in combination, the one or more steps of the methods 1100, 1200, 1300, 1400, 1500, and 1600 may be performed with circuitry or logic circuitry such as a programmable array logic for a field programmable gate array, an application-specific integrated circuit, or other programmable or application-specific logic circuitry. The circuitry may be programmed to provide one or more of the steps of the method 1100, 1200, 1300, 1400, 1500, and 1600, and the program may comprise program instructions stored on a non-transient computer readable memory or storage medium or programmed steps of the logic circuitry.

Compositions and Kits for Performing Digital Assays

The present disclosure provides for compositions and kits for performing the digital assays as described herein. In certain aspects, kits and assays are provided for performing digital PCR.

In various aspects, the present disclosure provides compositions and kits for performing a digital assay comprising: a first fluid; a second fluid, wherein the first fluid and the second fluid are immiscible in each other and are capable of forming an emulsion when agitated; a surfactant; and an amplification reagent.

In some aspects, the composition further comprises a sample. In certain aspects, the sample is a nucleotide. In further aspects, the composition further comprises a detectable agent, wherein the detectable agent is capable of labeling a sample. In some aspects, the sample is labeled with a detectable agent. In further aspects, the compositions further comprise a detectable agent capable of binding a nucleic acid sample.

In various aspects, the compositions comprise an amplification reagent selected from a polymerase chain reaction (PCR) reagent, rolling circle amplification (RCA) reagent, nucleic acid sequence based amplification (NASBA) reagent, loop-mediated amplification (LAMP) reagent or a combination thereof. In some aspects, the amplification reagent is a PCR reagent. In certain aspects, the PCR reagent is selected from a thermostable DNA polymerase, a nucleotide, a primer, probe, or a combination thereof.

In some aspects, the compositions further comprise a third fluid, wherein the third fluid is immiscible in the second fluid. In certain aspects, the compositions are capable of forming a double emulsion.

In various aspects, the first fluid is aqueous. In further aspects, the first fluid comprises the amplification reagent. In some aspects, the second fluid is an oil. In further aspects, the second fluid is an oil, and the second fluid is immiscible with the first fluid and the third fluid. In yet further aspects, the first fluid is different from the third fluid. In other aspects, the third fluid is an oil and the third fluid is immiscible with the first fluid and the second fluid.

In some aspects, the compositions further comprise a fluid interface modification element. In certain aspects, the fluid interface modification element is a surfactant. In further aspects, the fluid interface modification element is selected from a lipid, phospholipid, glycolipid, protein, peptide, nanoparticle, polymer, precipitant, microparticle, a molecule with a hydrophobic portion and a hydrophilic portion, or a combination thereof.

In certain aspects, the compositions further comprise a solidifying or gelling agent capable of converting one or more of the immiscible fluids to a gel or solid.

In some aspects, the present disclosure provides compositions and kits for performing a digital assay, the composition or kit comprising: a first fluid; a second fluid, wherein the first fluid and the second fluid are immiscible in each other and are capable of forming an emulsion when physically agitated; a surfactant; and a PCR reagent. In further aspects, the PCR reagents are selected from a thermostable DNA polymerase, a nucleotide, a primer, probe, or a combination thereof. In other aspects, the detectable agent is capable of binding a nucleic acid sample.

In certain aspects, the present disclosure provides compositions and kits for performing PCR comprising a first fluid and a second fluid, wherein the first fluid and the second fluid are immiscible in each other, a nucleic acid primer, deoxyribonucleotides, an enzyme suitable for the extension of the nucleic acid primer, a fluorescent label, and a detectable agent that is capable of binding a nucleic acid sample following amplification.

In further aspects, the compositions and kits can further comprise suitable buffering and stabilizing agents that are compatible with PCR amplification.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges can independently be included in the smaller ranges, and are also encompassed within the disclosure, subject to any specifically excluded limit in the stated range. Where the stated range includes one or both of the limits, ranges excluding either or both of those included limits are also included in the disclosure provided herein.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects, herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

While preferred aspects of the present disclosure have been shown and described herein, it is to be understood that the disclosure is not limited to the particular aspects of the disclosure described below, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims. In this specification and the appended claims, the singular forms "a," "an" and "the" include plural reference unless the context clearly dictates otherwise.

All publications, patents, and patent applications mentioned in this specification are herein incorporated by reference to the same extent as if each individual publication, patent, or patent application was specifically and individually indicated to be incorporated by reference.

EXAMPLES

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Example 1

Method for Generating Droplets of Variable Volumes in a Tube

This Example provides exemplary methods for the production of polydisperse droplets of variable volume according to one aspect of the present disclosure. In this example, PCR tubes are used, however, any suitable vessel can be used according to the present disclosure.

Figure 3:
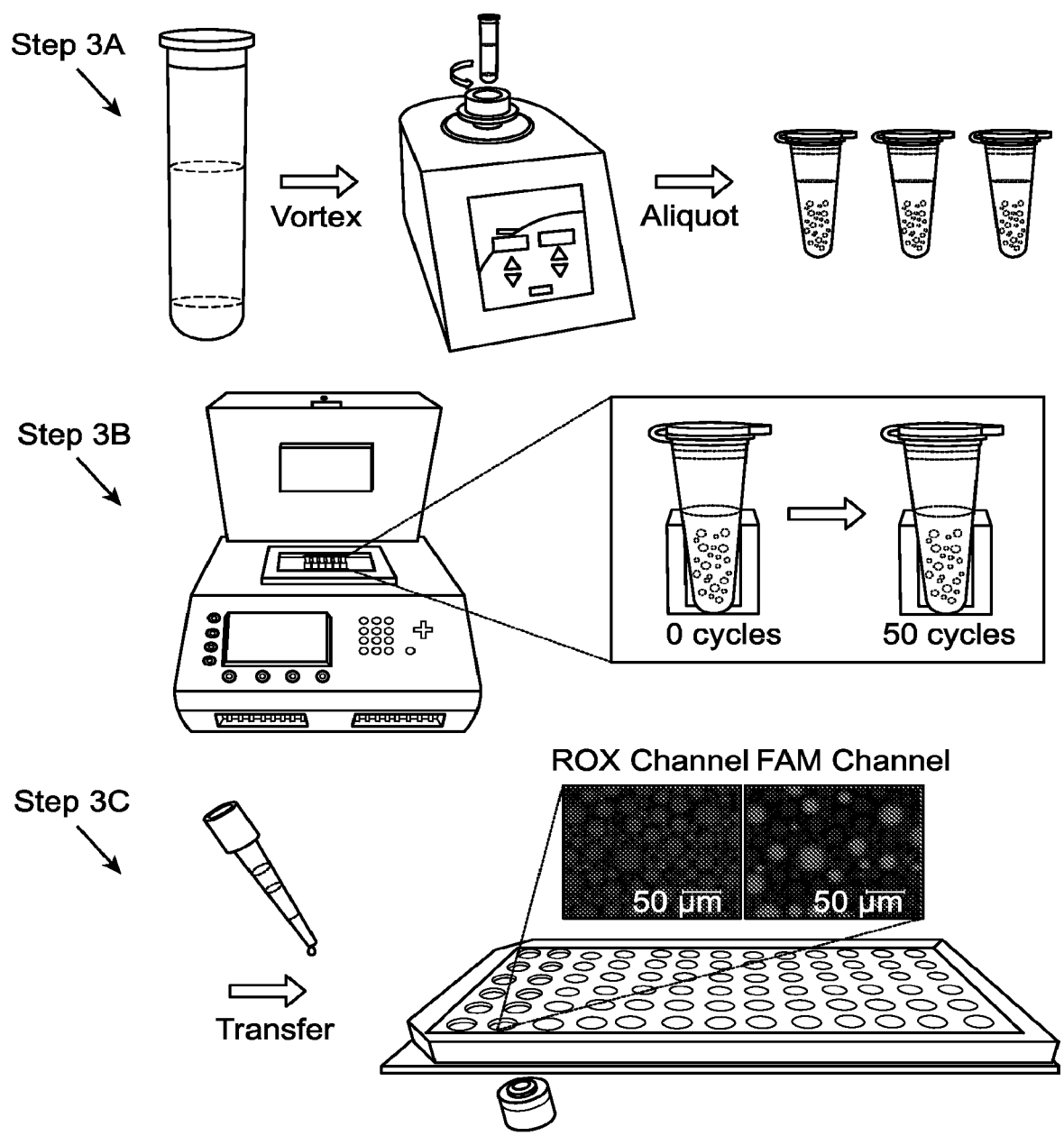
FIG. 3 depicts an exemplary method for performing a digital assay according to one aspect of the present disclosure. According to this aspect, polydisperse droplets containing a nucleotide sample can be produced by vortexing (Step 3A), the nucleotides can be amplified by PCR (Step 3B), and the nucleotide sample can be analyzed in a multi-well plate format (Step 3C).

FIG. 3 depicts the formation of an emulsion system by vortexing individual tubes. In a Step 4A, the aqueous phase containing the reaction mixture was pipetted into a 0.2 mL PCR tube that was prefilled with an appropriate oil-surfactant mixture. The oil phase consisted of 73% Tegosoft DEC, 20% light mineral oil and 7% ABIL WE 09 surfactant, that were freshly mixed and equilibrated for at least 30 minutes before use. Emulsions formed with this mixture showed superior thermostability during standard emulsion PCR. In a Step 4B, after pipetting the aqueous phase to the oil mixture, droplets of variable size were formed by vortexing for about 30 seconds at about 3000 rpm. Emulsification was further enhanced by adding a small stir bar to the mixture, which promoted breakup of the aqueous phase into smaller droplets during vortexing. The presence of the surfactant in the oil stabilized the emulsion, which reduced the frequency of droplet fusion in the mixture.

A system containing both aqueous and oil phases was added to a small collection microtube containing a small stainless steel bead. The tube was subsequently shaken at 15-17 Hz for 20 seconds to generate the emulsion. In a Step 4C, the emulsion was then transferred into a 0.2 mL PCR tube, and PCR was carried out in a Bio-Rad C1000 Thermal Cycler for 3 minutes at 95° C. (a hot start) and 50 cycles of 30 seconds at 95° C., 30 seconds at 54° C., and 30 seconds at 72° C.

Example 2

Method for Generating Droplets of Variable Volume in a Multi-Well Plate

This Example provides a method for the production of polydisperse droplets of variable volume and subsequent modification and analysis according to one aspect of the present disclosure.

Figure 4:
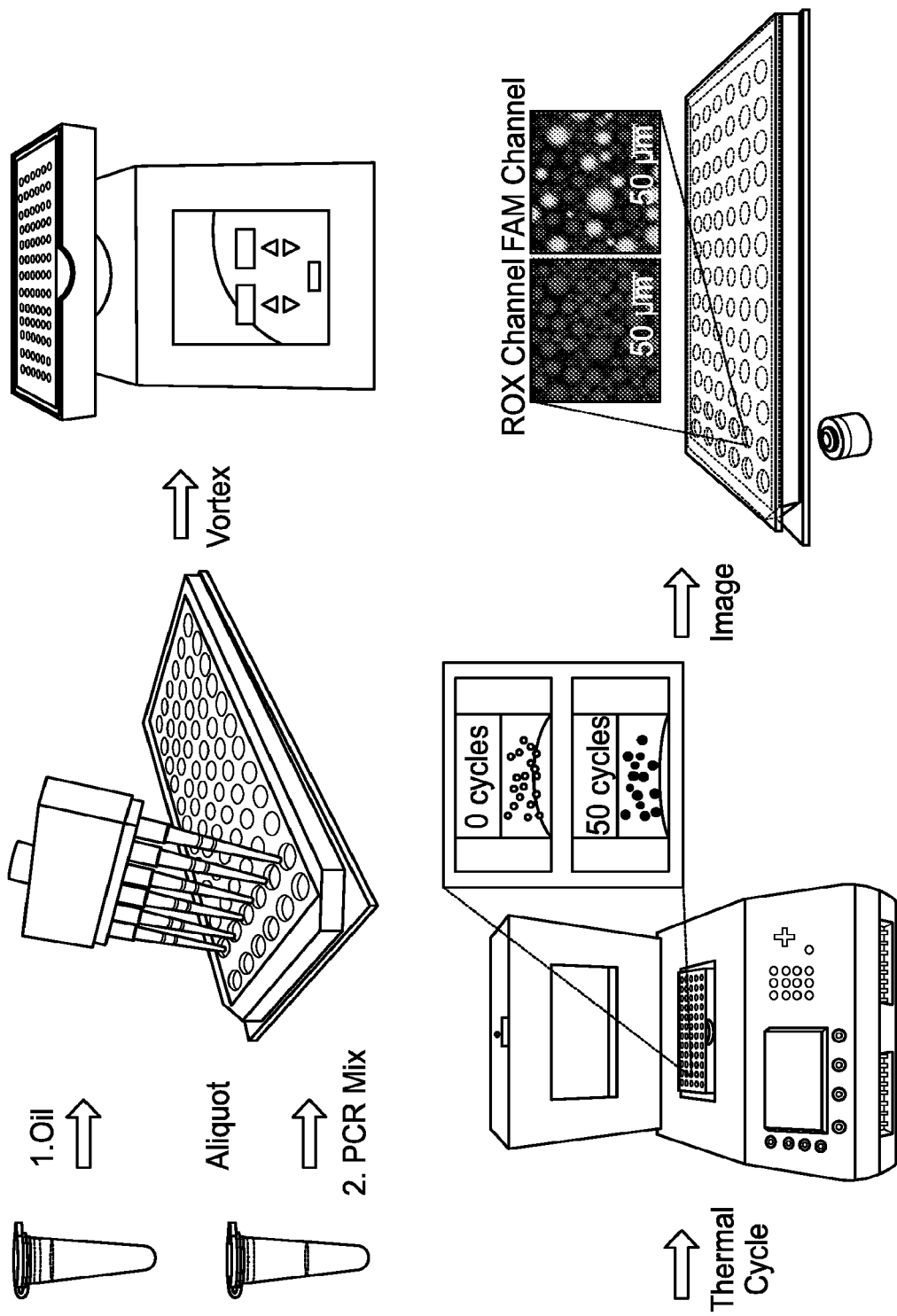
FIG. 4 depicts an exemplary method for performing a digital assay according to one aspect of the present disclosure. According to this aspect, emulsion PCR can be performed as part of an optimized high-throughput system with minimal need for sample transfer. According to this aspect, oil and aqueous PCR components are loaded onto a multi-well plate, the entire multi-well plate is vortexed to induce emulsification, the nucleotide components undergo PCR amplification in a thermal cycler, and the resulting products are imaged with a fluorescence microscope.

FIG. 4 depicts an optimized high-throughput process for droplet-emulsion PCR. After a multichannel pipette loads oil and aqueous PCR reagents onto a multiwell plate, the entire multiwell plate is vortexed for 30 seconds at 3000 rpm to induce emulsification. The multiwell plate is subsequently fitted with a thermal cycler adaptor, and the mixture undergoes PCR amplification for 3 minutes at 95° C. (a hot start) and 50 cycles of 30 seconds at 95° C., 30 seconds at 54° C., and 30 seconds at 72° C. The multiwall plate is then removed from the thermal cycler and imaged with a fluorescence microscope, with no further sample transfer steps required. In this example, any droplet instability (e.g. fusion) following emulsification will be independent of mechanical handling.

Example 3

Determination of Best-Fit Circle

This Example provides a method for determining the best-fit circle for droplets in a polydisperse droplet system. In this aspect, a set of pixels, which are presumed to be some or the entire boundary of a droplet are fit to a circle using an existing optimization algorithm. In this aspect, the Nelder-Mead algorithm as implemented in MATLAB is used. The algorithm minimizes a fit error that is defined as in Equation (1) below:

$$E_{Fit} = \frac{\sum_{p=1}^{N_p}\left[\sqrt{(X_p - X_{trial})^2 + (Y_p - Y_{trial})^2} - R_{trial}\right]^2}{R_{trial}^2} \quad (1)$$

In this equation, $X_{trial}$ and $Y_{trial}$ correspond to the trial location of the center of the circle for the current step in the optimization procedure. $R_{trial}$ is the trial radius of the circle for the current step in the optimization procedure. There are $N_p$ pixels in the set of external pixels being fit with $X_p$ and $Y_p$ being the location of the pth pixel in the set. Therefore, the quantity inside the square root sign is the distance from the trial center to the pth pixel, from which the trial radius is subtracted to obtain an error. The error is squared, summed over all pixels in the set and then divided by the square of the trial radius to obtain the fit error.

As part of the optimization, a count is made of the number of pixels inside the Group that are also inside the current trial circle. If the number of pixels inside the circle ($N_C$) exceeds the number of pixels that are both inside the circle and inside the Group ($N_{C,G}$), then the current trial location and radius are penalized by adding the following (as defined in Equation (2)) to the fit error:

$$(N_C - N_{C,G})^2 \quad (2)$$

Addition the quantity from Equation (2) inhibits the optimization from choosing as a best-fit circle a circle that is too large and extends significantly outside the Group, as can occur when only a fraction of a droplet's boundary is being fit and noise causes that fraction to exhibit a curvature that is unrepresentative of the droplet. In some cases the methods use the fit error per pixel as part of the evaluation of the quality of the fit to droplets. The number of pixels in the fit is $N_p$ and the fit error per pixel is defined in Equation (e) below:

$$E_{PerPixel} = \frac{1}{N_p} \frac{\sum_{p=1}^{N_p}\left[\sqrt{(X_p - X_{trial})^2 + (Y_p - Y_{trial})^2} - R_{trial}\right]^2}{R_{trial}^2} \quad (3)$$

In another aspect of the present disclosure, the mean square error is used in the evaluation of the quality of the fit to the droplets. This is defined in Equation (4) below:

$$E_{ms} = \frac{1}{N_p}\sum_{p=1}^{N_p}\left[\sqrt{(X_p - X_{trial})^2 + (Y_p - Y_{trial})^2} - R_{trial}\right]^2 \quad (4)$$

Examples 4, 5 and 6 each reference the fitting of a circle to external boundary pixels or feature pixels, which relates to the methods described in this example.

Example 4

The Reverse Watershed Method for Identifying Droplets

This Example describes an exemplary process for performing the Reverse Watershed Method according to an aspect of the present disclosure.

According to this aspect, an initial background cutoff for the image was calculated by assuming that 40% of the image was background. For this initial background cutoff, 20% (equal to 40% divided by 2) is the estimated percentile of the image intensities that corresponds to the median of the background pixel intensities. An estimated background standard deviation was calculated by assuming it was one half the difference between the 20% percentile of the image and the 1% percentile of the image. The initial estimate of the background cutoff was then the estimated median plus twice the estimated standard deviation. Pixels with intensities less than the initial estimate of the background cutoff were selected for the next step. The average and standard deviation of the intensity of the selected pixels was calculated and the percentage of image pixels with intensities less than the average was determined and found to be 22%. That percentage was compared with 20%, the initial estimate of the estimated percentile of image intensities that corresponds to the median of the background. These values were judged to be in good agreement and the average and standard deviation of the selected pixels were accepted as the average and standard deviation of the background in the image for the purposes of calculating the SCT and BT. In the event those values had not been in good agreement, then a new initial background cutoff would have been calculated by using 22% as then estimated percentile of the image intensities that corresponds to the median of the background pixel intensities and repeating the procedure starting at the beginning of this paragraph.

The SCT for the image was then determined by multiplying the standard deviation of the background calculated previously by a signal-to-noise-ratio and adding the result to the average intensity of the average background calculated previously. Here, the signal-to-noise ratio was selected as 3.2, however, this value can be adjusted by the user depending on the amount of noise in the images.

A cutoff threshold was then selected that equaled the largest pixel intensity of the image. This cutoff threshold was lowered in 30 steps until it reached the SCT. In this case, the steps were spaced at 904.0, 872.0, 841.2, 811.5, 782.8, 755.1, 728.4, 702.7, 677.8, 653.8, 630.7, 608.4, 586.9, 566.2, 546.1, 526.8, 508.2, 490.2, 472.9, 456.2, 440.1, 424.5, 409.5, 394.5, 379.5, 364.5, 349.5, 334.5, 319.5, and 304.5. The first value was equal to the largest pixel intensity in the image and the last one was equal to the SCT for the image. A copy of the image that was smoothed was created for use in a later step. In this example, the smoothing was performed by MATLAB's conv2( ) function that convoluted the image with a smoothing structure defined (using MATLAB's notation) as '[0.05, 0.10, 0.05; 0.10, 0.40, 0.10; 0.05, 0.10, 0.05]'.

At each step, imaging analysis software was used to find sets of pixels (hereafter referred to simply as a pixel set) in the image above the current step's cutoff threshold. These pixel sets may comprise "protrusions" or "islands" from the "water level." In this example, pixels were required to be 4-connected to be considered to be part of the same pixel set. If the area of such a pixel set equaled or exceeded a user-defined criterion (i.e., 9 in this case), then it was marked as a region of interest (ROI). In this case, the image was closed using the MATLAB routine, imclose( ), with a structuring element defined by the MATLAB expression strel('disk', 1) before determining if the area of the set was of sufficient size. Once a ROI appeared in a particular location of the image, its area was tracked as the cutoff threshold is decreased. The location of the maximum intensity pixel within each ROI and the values of the pixels within the ROI were also tracked.

As the cutoff threshold was lowered, it was possible for two or more ROIs to merge. A pixel set that is above a particular cutoff threshold can include two or more ROIs that were separate for a larger cutoff threshold. This can happen because either: (i) the different ROIs represent different droplets that are so close together that the boundary region between them has a larger pixel intensity than the current cutoff threshold or (ii) the amplitude of noise in the sample is sufficiently large that two or more regions within a single droplet exhibit local maxima. These maxima can appear to the algorithm as separate ROIs at larger cutoff thresholds.

A set of user-defined criteria was used to determine whether different ROIs whose areas were contained within the same pixel set of the current step should be merged and thereafter treated as one ROI or not merged and tracked as separate ROIs. This determination was made depending on: (i) the distance between the maximum intensity pixels of the different ROIs and (ii) the values of the maximum intensity pixels of the different ROIs, and. Other user-defined criteria could be applied as well to make this determination.

In this example, for criterion (i) if the distance in maximum intensity pixels of the smoothed copy of the image was less than 5 pixels, then the two ROIs were merged and thereafter treated as a single ROI. In this example, for criterion (ii), if maximum intensity pixels have intensities within 0.75 times the background standard deviation of the cutoff used to identify the current pixel set, then the two ROIs were merged and thereafter treated as a single ROI. The reasoning is that if two previously separate ROIs appeared in the same pixel set for the current cutoff value, then the pixels in the pixel set that lie between the two maximum intensity pixels must have had intensities above the current cutoff. Therefore if the maximum intensity in each of the two ROIs are both close to the current cutoff, the pixels in the pixel set that lie between the two maxima must have had intensities close to the maxima. Therefore, the two ROIs were combined and were assigned to the same droplet.

After the last step (i.e., the point at which the SCT has been used), the pixel sets were referred to as Pixel Groups. Where different ROIs whose areas were contained within the same Pixel Group were not merged, the unassigned pixels of that Pixel Group were assigned to an ROI. Specifically, a list of unassigned pixels within the Pixel Group was sorted by intensity, and the pixel with the largest intensity that was immediately adjacent to one and only one of the ROIs was assigned to that ROI. This process was repeated until the only unassigned pixels remaining were those that were immediately adjacent to two or more different ROIs. Those pixels were left unassigned.

Figure 5A:
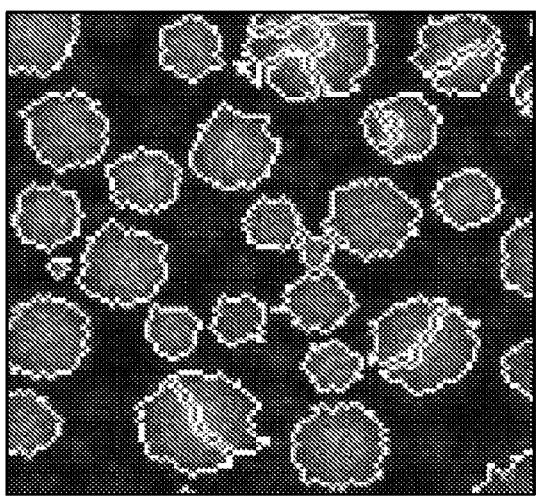
FIGS. 5A and 5B depict the results of the initial steps of the Reverse Watershed Method as applied to the image in FIG. 1, including the identification of regions of interest (ROIs) as shown in FIG. 5A and the final, processed image with optimized circular regions as shown in FIG. 5B, from which information on droplet size and target molecule presence can be determined.

The Reverse Watershed Method was applied to the image in FIG. 1, which is a gray-scale image of a polydisperse droplet emulsion system obtained using confocal fluorescent microscopy. As shown in FIG. 5A, the image was divided into groups that are separated by pixels whose intensity is below the background threshold. Some of the groups contain only a single ROI and some contain two or more. The boundary pixels depicted in FIG. 5A are those pixels belonging to a group that were adjacent to a non-group pixel.

The resulting Pixel Groups were analyzed and the ROIs within them were assigned to droplets and subjected to the following process steps, which need not necessarily occur in the order described below:

Step 1. If a Group contained only a single ROI, then it was considered to be a single droplet and its external boundary pixels were fit to a circle to obtain a droplet diameter.

Step 2. For ROIs not yet assigned to a droplet, a best-fit circle to the external boundary pixels of that ROI was obtained as described in Example 3. Each unassigned ROI was then checked. If the number of pixels of a ROI that were inside of the circle was at least 30% of the area of the circle, then a fit was performed combining the external boundary pixels of the ROI being checked with the external boundary pixels of any adjacent ROI that is not already assigned to a droplet. Two ROIs were considered "adjacent" when an interior boundary of one ROI is separated by zero or one pixel from the interior boundary of the other. In FIG. 5A, the ROIs that were separated by what appears as a double line are considered adjacent. The double line represents the two interior boundaries that lay near each other. The combined set of external boundary pixels were fit to a circle and the results were evaluated to decide if the two ROIs should be combined and considered to part of a single droplet. The criteria for combining the two ROIs were: (i) the fit error per pixel for the combination of two ROIs was less than 0.12 or the fit error per pixel was less than 1.5 times the fit error of the original ROI being checked and (ii) the area of the two ROIs together inside the best-fit circle was at least 85% of the area of the area of the ROIs. If the two ROIs were combined, then they were thereafter denoted as a droplet and treated as a single unit. The external boundary pixels of the droplet were then the set of external boundary pixels of the ROIs assigned to that droplet. This process was repeated with all adjacent ROIs.

Step 3. If an unassigned ROI had no adjacent ROIs that were unassigned, then the method fit the external boundary of that ROI to a circle. The ROI was accepted as a droplet if the fit error per pixel was less than 0.12 and the area of the ROI inside the best-fit pixel was at least 60% of the area of the circle.

Step 4. This method then checked pairs of droplets to determine if they were in fact portions of the same droplet. At this step it required that the best-fit circle of the droplets being checked be similar in size to each other. The method compared the distance between the centers of droplets that had already been found. It is possible that two regions identified as droplets at this stage were actually portions of the same droplet. The distance between the best-fit center of a pair of droplets was calculated and if it was less than 20% of the best-fit radius of each of the droplets, then the pair was tested to see if they were actually portions of the same droplet. The external boundary pixels of the two droplets were combined and the combined set of pixels was fit to a circle. The fit errors of the two droplets being considered was summed and divided by the number of pixels in the combined set of external boundary pixels. The fit error per pixel of the combined set must be less than 1.5 times this quantity and also less than 0.12. In that case, the two droplets were combined and thereafter considered to be one droplet. This process was repeated for all pairs of droplets.

Step 5. Next, each Pixel Group was examined to determine if it had both droplets and unassigned ROIs. If so, then for each droplet, the unassigned ROIs were examined and determined if at least 85% of a given ROI's area sat inside the best-fit circle associated with the droplet. If so, then that unassigned ROI was a candidate to be added to the droplet. Next a combined external boundary pixel set was made by combining the external pixels of the droplet with the external boundary pixels of the ROI. The combined set was then fit to a circle. There were several criteria that needed to be satisfied before it was concluded that the ROI should be assigned to the droplet, these included: (i) the distance between the location of the best-fit circle of the combined set and the location of the best-fit circle of the droplet must be less than 3 pixels (this depends on a number of considerations primarily the size of the pixels in the image); (ii) the distance between the location of the best-fit circle of the combined set and the best-fit circle of the ROI must have been less than 20% of the radius of the best-fit circle of the ROI; (iii) the fit error per pixel of the combined set must have been less than twice the fit error per pixel for the ROI; (iv) the fit error per pixel of the combined set must have been less than 0.12 and (v) the mean squared error of the combined fit must have been less than 1.5 times the mean squared error for the best-fit circle to the ROI. If all of these criteria were fulfilled, then the ROI was assigned to the droplet.

Step 6. In this step, pairs of droplets were examined to determine if they are portions of the same droplet. In some aspects, the droplets making up the pairs can have dissimilar diameters. The distance between the best-fit center of a pair of droplets was calculated and if it was less than 50% of the best-fit radius of each of the droplets, then the amount of overlap of the two droplets area was calculated. If more than 60% of the area of each best-fit circle sat inside the other best-fit circle, then the external boundary pixels of the two droplets were combined and the combined set of pixels was fit to a circle. The list of criteria the fit must satisfy is longer than in the previous step. A multiplier $M_{err}$ was defined to be 1.5. Then, the fit errors of the two droplets being considered was summed and divided by the number of pixels in the combined set of external boundary pixels. The fit error per pixel of the combined set must be less than $M_{err}$ times this quantity and also less than 0.12. Next the mean squared error of the combined fit, $MSE_{combined}$ was calculated. In addition, a new mean squared error was calculated for each of the two droplets being checked, but instead of using the best-fit circle of each droplet, the mean squared error for each droplet was calculated by comparing the best-fit circle of the combined set of pixels to the external boundary pixels assigned to each droplet. $MSE_{combined}$ must be less than $M_{err}$ times the new mean squared error of each droplet. Finally, the best-fit location for the combined set of pixels was invariably shifted from the best-fit location for each of the two droplets being checked. The distance from the best-fit location of the first droplet to the best-fit location of the combined set was determined. The difference must be less than 20% of the best-fit radius of the first droplet. The distance from the best-fit location of the second droplet to the best-fit location of the combined set was determined. The difference must be less than 20% of the best-fit radius of the second droplet. This was repeated for all pairs of droplets in the image. If a pair of droplets was found to have satisfied all of these criteria, then those were combined and thereafter treated as a single droplet. After all of the droplets had been checked, 0.35 was added to $M_{err}$ and this entire step was repeated. Gradually increasing $M_{err}$ led to droplets slowly being combined and reduced the possibility of incorrect combination. This process continued for increasing values of $M_{err}$ up to 2.9.

Step 7. This step involved the checking of pairs of droplets that had significant overlap, regardless of whether they were of similar size. A multiplier $M_{err}$ was defined to be 1.5 and a minimum fraction $F_{min}$ was defined to be 50%. The droplets of an image were ordered from largest to smallest by the ratio of the number of external boundary pixels to the circumference of the best-fit circle. Pairs of droplets (i, j) were checked, where i refers to the droplet with the larger radius and j refers to the droplet with the smaller radius. If at least $F_{min}$ of the area of droplet j was overlapped by the area of droplet i, then the pair was checked to see if they should be combined. The external boundary pixels of the two droplets were combined into a set that was fit to a circle. A number of criteria must be met in order to conclude that the two droplets should be combined, including the following: (i) the fit error per pixel for the combined fit must be less than 0.12; (ii) the fit error per pixel of the combined fit must be less than $M_{err}$ times the fit error per pixel of the best-fit circle for droplet j; (iii) the mean squared error of the combined fit must be less than $M_{err}$ times the mean squared error for the best-fit circle for droplet j and (iv) the distance between the best-fit location of the center of the circle for the combined fit and the best-fit circle for droplet j must be less than 20% of the best-fit radius of droplet j. If all these criteria were met, then droplets i and j were combined and considered one droplet.

Step 8. In this step, each Pixel Group was examined and determined if it had both droplets and unassigned ROIs. If so, then for each droplet, it examined each unassigned ROI and determined if at least 85% of the ROI's area lay inside the best-fit circle associated with the droplet. If so, then that unassigned ROI was a candidate to be added to the droplet. Next a combined external boundary pixel set was made by combining the external pixels of the droplet with the external boundary pixels of the ROI. The combined set was fit to a circle. This step has a set of criteria that must be satisfied if an ROI is to be added to the droplet, including the following: (i) the fit error per pixel of combine fit must be less than 1.2 times the fit error per pixel of the fit error for the ROI and (ii) the distance between the location of the center of the best-fit circle to the combined set and the location of the center of the best-fit circle to the ROI must either be less than 1.4 pixels or less than 20% of the radius of the best-fit circle to the ROI. If these criteria were met, then the ROI was assigned to the droplet.

Step 9. At this stage it was still possible that the ROIs assigned to a droplet do not completely describe the circumference of the droplet. The droplets of an image were ordered from largest to smallest by the ratio of the number of external boundary pixels to the circumference of the best-fit circle. For each Pixel Group, pairs of droplets each of which had a ratio less than 0.5 were examined. This step had some criteria that were required to be met before the droplets were considered further for consolidation. The amount of overlap between the best-fit circles of the two droplets was calculated. The distance between the centers of the two best-fit circles was calculated. The criteria included the following: (i) the size of the overlap must exceed 30% of the area of both circles; (ii) the distance between the two circles must be less than 20% of the best-fit radius of whichever best-fit circle is larger and (iii) the difference in best-fit radius between the two best-fit circles must be less than 30%. If these criteria were satisfied, then the external boundary pixels of the two droplets were combined and circle was fit to the combined set. This procedure was repeated for all pairs of droplets.

Step 10. For each droplet, the ratio of the number external pixels to the circumference of the best-fit circle was then calculated and any droplet for which this ratio does not exceed 0.65 was removed from consideration.

Step 11. For each Pixel Group, a list of all ROIs that were still not assigned to a droplet was prepared. Then for each unassigned ROI, the method searched for the droplet with which it had the greatest overlap. If the size of that overlap exceeded 50% of the area within the ROI, then the method examined whether the ROI should be assigned to the droplet. It calculated the area inside the best-fit circle of the droplet that was not occupied by a ROI assigned to the droplet. If the area of the unassigned ROI was less than 1.05 times the area of the unoccupied area inside the droplet's best-fit circle, then external boundary pixels of the droplet and the unassigned ROI were combined to make a combined set of external boundary pixels. This combined set was then fit to a circle. This step has a set of criteria which must be satisfied before an ROI can be added to the droplet including the following: (i) the fit error per pixel of combine fit must be less than 1.2 times the fit error per pixel of the fit error for the ROI; (ii) the distance between the location of the center of the best-fit circle to the combined set and the location of the center of the best-fit circle to the ROI must either be less than 1.4 pixels or less than 20% of the radius of the best-fit circle to the ROI or (iii) the fit error per pixel of the fit error per pixel for the combined set must be less than 0.12. If these criteria were met, then the ROI was assigned to the droplet.

Step 12. Any ROIs without any external boundary pixels were then assigned to that droplet if they were inside the best-fit circle of a droplet.

Figure 5B:
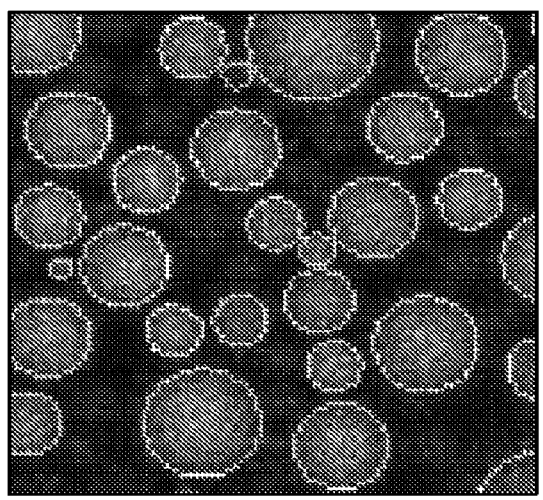

FIG. 5B shows the final, processed image prepared by the methods in this example. The image in FIG. 5B corresponds to FIGS. 1 and 5A and includes the best-fit boundaries for those droplets that can be identified as droplets. The image of FIG. 5B can then be used to determine droplet size and target molecule presence for each given identified droplet.

Example 5

Circle Detection Method for Identifying Droplets

This Example describes an exemplary process for performing the Circle Detection Method according to an aspect of the present disclosure.

According to this aspect, the SCT was calculated as described above in Example 4 for the Reverse Watershed Method, except that the signal-to-noise ratio was 2.5 (rather than 3.2 in Example 4). This SCT was applied to an image to define Pixel Groups within the image. The value of the SCT was also used to identify holes within each Pixel Group. The Pixel Group was checked for 8-connected sets of pixels whose intensity was below the SCT inside the Pixel Group. If the set contained 9 or more pixels it was denoted a Hole. The list of any pixels within a Pixel Group that were adjacent to a Hole was added to the list of external boundaries of the Pixel Group. The external boundaries of the Pixel Groups were trimmed to eliminate noise pixels. The list of trimmed external boundary pixels includes only those external boundary pixels of the Pixel Group that were adjacent to at least one interior pixel. The trimmed external boundary pixels will also be referred as feature pixels in this example. The Circle Hough transform was applied to the list of feature pixels of each Group.

The transform was performed for circle radii ranging from 3 to 60 pixels for each Pixel Group. According to this aspect, the standard transform method was modified to account for significant levels of noise in the image. This modification can optionally be performed, depending upon the noise characteristics of the images used. The number of votes assigned to a pixel was the weight assigned to the possibility that the pixel was the center of a circle of radius R. Ordinarily, for a given radius R, this value is simply the number of feature pixels within a distance R of the pixel. In this method it was the number of feature pixels within a distance R−1 to R+1 of the center of the circle. The number of votes for a particular center location and the list of feature pixels voting for each center location were calculated for each value of R. The circles found by the Circle Hough Transform will be referred to as "H-circles" in this example to distinguish them from best-fit circles that were obtained when a list of external pixels is fit to a circle. The latter are referred to as "circles."

The list of H-circles generated for each Pixel Group was reduced as follows. H-circles with fewer than 9 votes were discarded. Also H-circles for which the ratio of the number of votes to the circumference of the H-circle was less than 0.40 were discarded. H-circles that contained any Hole pixels were discarded. Next the pixels that comprised the circumference of the H-circle were identified and the number of them that were in the image was counted (a H-circle can extend outside of the image). The criteria applied at this point were as follows: (i) the number of circumference pixels in the image, $N_{CI}$, must exceed 14; (ii) the ratio of $N_{CI}$ to the number of pixels in the circumference must exceed 0.60 and (iii) the ratio of the number of votes for the H-circle to $N_{CI}$ must exceed 0.50. If the H-circle passed these criteria, then the fraction of the circumference that was in the background of the image was checked. If that fraction was less than 0.15, then the H-circle was accepted at this stage. If the fraction was not less than 0.15, but the radius was 5 or less, then the fraction of the H-circle's area that lays more than 1 pixel away from a pixel in the group was calculated. If the H-circle's radius was 4 or 5 and the fraction is 0.15 or less, then the H-circle was accepted at this stage. If the H-circle's radius was 3 and the fraction is 0.20 or less, then the H-circle was accepted at this stage.

Figure 6A:
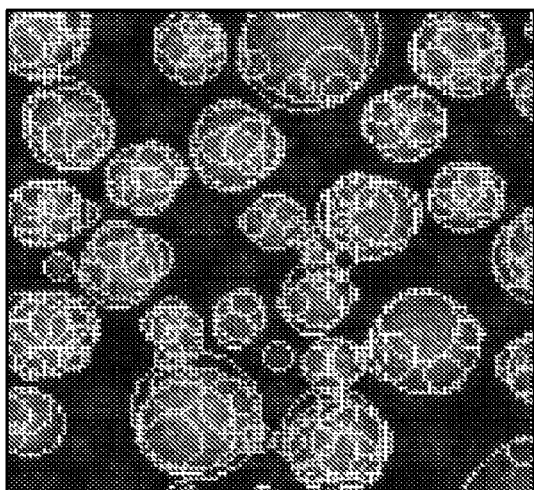
FIG. 6A shows a processed image produced after performing the initial steps of the Circle Detection Method as applied to the image of FIG. 1.

The ratio of the number of votes for an H-circle to the number of circumference pixels in the image was calculated for the H-circles still accepted at this stage. The H-circles were sorted by this ratio starting with the largest and then descending in size. Each H-circle was compared against all the H-circles with a smaller value of that ratio. If the centers of the H-circles were within $\sqrt{10}$ pixels of each other and the radii of the H-circles differ by less than four, then the H-circle with the smaller value of the ratio was rejected. The image in FIG. 1 was analyzed by this method and the results to this stage are shown in FIG. 6A. There were overlapping H-circles at this stage.

In this example, the next step was to reject H-circles that were a poor representation of any droplet and then combine circles that were judged to represent portions of the same droplet. Each H-circle was associated with the set of external boundary pixels that voted for that H-circle. The list of feature pixels for each H-circle was fit to a circle and the mean squared error for the fit was calculated. At this point each H-circle defined a set of pixels that were fit to obtain a best-fit circle (BF-circle). For the additional analyses in this example, if a BF-circle was rejected, then the H-circle associated with it was also rejected. If a BF-circle was assigned to a droplet, then the associated H-circle was assigned to the same droplet. If the mean squared error exceeded 0.70, then the BF-circle was rejected. It was observed that some of the larger droplets in the sample had extremely irregular external boundaries. This was ascribed to the refractive index mismatch between the contents of the droplets and the continuous medium that surrounded them. Small droplets located between the large droplet and the microscope objective are capable of acting as lenses and thus distort the image of the large droplet's boundary. To prevent this from causing a premature rejection of larger BF-circles, the above criterion was relaxed for larger BF-circles. If the number of votes (i.e., $N_F$ external boundary pixels fit to a circle) was greater than 30, then the BF-circle was rejected if the mean square error of the fit exceeded $0.70+0.03\times(N_F-30)$.

Next, the amount by which the area of pairs of BF-circles overlapped was calculated and a list compiled of pairs where the area of overlap was greater than 65% of the area of one of the two BF-circles. For each pair, the fraction of area inside the circle that was part of the Pixel Group was calculated, and the fraction of votes for each circle that were unique (were not also votes for the other circle) was calculated. If the fractions calculated for one BF-circle were both smaller than the corresponding fractions for the other, then the first BF-circle was rejected.

For the pairs for which neither BF-circle had been rejected and that had different areas, another test was applied. The number of pixels that are inside the smaller BF-circle but not inside the larger BF-circle was calculated. If that number was less than half the number of votes for the smaller BF-circle, then the smaller BF-circle was rejected.

For the pairs for which neither BF-circle had been rejected to this point the distance between the centers of the BF-circles was calculated and the difference between the radii of the two BF-circles was calculated. If the distance between the centers was less than 2.1 pixels and the difference between the radii was less than 2.1 pixels, then the BF-circle with the smaller number of votes was rejected.

Next, for each BF-circle, the number of unique votes was calculated. Unique votes are votes that are not also a vote for any other BF-circle that had not itself been rejected previously. If the number of unique votes was less than 10 or the ratio of unique votes to the total number of votes was less than 0.40, then that BF-circle was rejected.

For each Pixel Group a list of external Pixel Group boundary pixels that were not assigned to any H-circle (unassigned) was compiled. If the fraction of unassigned pixels was less than 10% of the total number of external Pixel Group boundary pixels then the rejected H-circles were reexamined. For each of them, a list of unique votes (votes that were not part of any accepted H-circle) was compiled. If the number of such votes exceeded 60% of the circumference of the rejected H-circle, the rejected H-circle was restored to the list of accepted H-circles. All H-circles accepted at this point were provisionally considered to be droplets.

Next, each possible pair of droplets in a Pixel Group was examined, these are referred to respectively as "droplet one" and "droplet two" below. The number of unique votes (i.e., votes for one droplet that are not votes for the other) was calculated for every droplet in every pair. The number of unique votes are denoted $N_{U1}$ and $N_{U2}$ for droplet one and droplet two, respectively. If either of these numbers were less than 9, then the pair was subjected to additional tests. For these tests. the distance (d) between the best-fit centers of the droplets was calculated. Also, for these tests, the area-inside denotes the pixels that are both inside the best-fit circle and also in the Pixel Group. Then four additional quantities were calculated. These were the ratio of d to the best-fit radius of droplet one ($D_1$), the ratio of d to the best-fit radius of droplet two ($D_2$), the fraction of the area-inside droplet one that is not inside droplet two ($F_1$), and the fraction of the area-inside droplet two that is not inside droplet one ($F_2$). It should be noted that the terminology used in this example applies only to this example.

The following additional Conditions and Tests were applied:

Condition A: if $N_{U1}$ and $N_{U2}$ were both less than 9, then Test A was performed. Test A. If both $D_1$ and $D_1$ were both less than 0.3, then the droplet with the smaller best-fit radius was rejected.

Condition B: if Condition A did not apply and $N_{U1}$ was less than 9, then Test B was performed. Test B: if $F_1$ was less than 0.4, then droplet one was rejected.

Condition C: if Conditions A and B did not apply and $N_{U1}$ was less than 9, then Test C was performed. Test C: if $F_2$ was less than 0.4, then droplet two was rejected.

Condition D: if none of Conditions A, B or C applied, then a two-part Test D was applied. Test D, Part 1: if $N_{U1}$ was less than $N_{U2}$, and if $D_1$, $D_2$ and $F_1$ were all less than 0.3, then droplet one was rejected. If not, then Test D, Part 2 was applied. Test D, Part 2: if $N_{U2}$ was less than $N_{U1}$ and if $D_1$, $D_2$ and $F_2$ were all less than 0.3, then droplet two was rejected.

Condition E: if none of Conditions A, B, C or D applied, then Test E was applied. Test E: the fraction of unique area pixels was calculated that, for the purposes of this test, was defined as the fraction of the area inside a droplet that is not inside any other droplet in the Pixel Group. The fraction of overall unique votes was calculated, which for the purposes of this test was defined as the fraction of votes for a droplet that were not votes for any other droplet in the Pixel Group. If both fractions for droplet one were smaller than the corresponding fractions for droplet two, then droplet one was rejected. If both fractions for droplet two were smaller than the corresponding fractions for droplet one, then droplet two was rejected.

Next each droplet in the Pixel Group was examined individually. A list of pixels that are part of the best-fit circumference of the droplet and within the image was constructed. The fraction of those pixels that were inside the Pixel Group, but not coincident with or adjacent to an external boundary pixel ($F_C$) was calculated. If $F_C$ exceeded 60%, then the droplet was rejected.

If $F_C$ exceeded 0.3 and the number of pixels that were inside the Pixel Group, but not coincident with or adjacent to an external boundary pixel was greater than 2, then a different test was performed. Two sets were created from the list of pixels that were part of the best-fit circumference of the droplet. The first set (set one) consisted of those pixels that were coincident with or adjacent to a vote assigned to the droplet. The second set (set two) consisted of those pixels that were inside the Pixel Group, but not in set one. The average ($A_1$) and standard deviation ($S_1$) of the intensities of the pixels in set one were calculated. The average ($A_2$) of the intensities of the pixels in set two were calculated. If $A_1+(2-F_C)\times S_1 < A_2$, then the droplet was rejected. In some cases, noise distorting the external boundary of a droplet results in H-circles that are significantly smaller than the droplet. In those cases, the portion of the BF-circle's circumference that lies in the interior of the droplet can have an average intensity that is significantly larger than the portion that lies near the external boundary of the Pixel Group. This test was used to identify and reject those H-circles.

Next, for each droplet, the list of pixels-inside (i.e., pixels that are inside the best-fit circle and inside the droplet) was constructed and the intensities of those pixels were analyzed. If the 90th percentile of those intensities was less than the average background intensity plus 5 times the standard deviation of the background intensities, then the droplet was rejected. If the number of pixels-inside that had intensities greater than the average background intensity plus 3.5 times the standard deviation of the background intensities ($N_{3.5}$) was fewer than 4, then the droplet was rejected. The fraction of pixels-inside whose intensity was above the average background intensity plus 3.5 was also calculated ($F_{3.5}$). If $F_{3.5}$ was less than 0.10, the droplet was rejected. If $F_{3.5}$ was less than 0.15 and $N_{3.5}$ was less than 20, the droplet was rejected.

The droplets were reexamined at that point. If the number of unique votes (votes for a droplet that are not also votes for a different droplet) was less than 5, the droplet was rejected. If the number of unique votes was less than 9 and the mean squared error of the fit was more than 0.25 and the fit error is more than 0.4, then the droplet was rejected.

An attempt was then made to assign any external Pixel Group boundary pixels to droplets. For each droplet, any external Pixel Group boundary pixels that were inside or adjacent to the best-fit circle of a droplet were provisionally added to the list of votes (pixels that were used to obtain a best-fit circle) of that droplet. Pixels that were added to more than one droplet by this procedure were removed from the list of votes assigned to those droplets.

A best-fit circle was then obtained using the revised list of votes for each droplet.

Next each droplet in the Pixel Group was examined individually. A list of pixels that are inside the best-fit circle of a droplet, part of the Group, but not part of another droplet was compiled. If the number of those pixels was less than 75% of the total number of pixels inside the best-fit circle of a droplet and inside the Pixel Group, then the following two tests (Tests F and G) were applied.

Test F: a list of pixels that were part of the best-fit circumference of the droplet and within the image was constructed. The fraction of those pixels that were inside the Pixel Group, but not coincident with or adjacent to an external boundary pixel ($F_C$) was calculated. If $F_C$ exceeded 60%, then the droplet was rejected.

Test G: if $F_C$ exceeded 0.3 and the number of pixels that were inside the Pixel Group, but not coincident with or adjacent to an external boundary pixel, was greater than 2, then a different test was performed. Two sets were created from the list of pixels that were part of the best-fit circumference of the droplet. The first set (set one) consisted of those pixels that were coincident with or adjacent to a vote assigned to the droplet. The second set (set two) consisted of those pixels that were inside the Pixel Group, but not in set one. The average ($A_1$) and standard deviation ($S_1$) of the intensities of the pixels in set one were calculated. The average ($A_2$) of the intensities of the pixels in set two were calculated. If $A_1+(2-F_C)\times S_1 < A_2$, then the droplet was rejected. In some cases, noise distorting the external boundary of a droplet results in best-fit circles that are significantly smaller than the droplet. In those cases, the portion of the best-fit circle's circumference that lies in the interior of the droplet can have an average intensity that is significantly larger than the portion that lies near the external boundary of the Pixel Group. This test was used to identify and reject those droplets.

If the mean squared error exceeded 1.0, then the BF-circle was rejected. However, if the number of votes ($N_F$ external boundary pixels fit to a circle) was greater than 30, then this requirement was relaxed and droplet was rejected if the mean square error of the fit exceeded $1.0+0.03\times(N_F-30)$.

If the max fit error per pixel exceeded 0.10, then the droplet was rejected.

The fraction of the votes for a droplet whose distance to the best-fit center is within ±1.16 pixels of the best-fit radius is calculated ($F_G$). Also the ratio of votes for a droplet to the size of that portion of the best-fit circumference that lay in the image was calculated ($F_{VC}$). If $F_G$ was less than 0.5 and $F_{VC}$ was less than 0.575, the droplet was rejected.

For each droplet, the list of pixels-inside (pixels that are inside the best-fit circle and inside the Pixel Group) was constructed and the intensities of those pixels was analyzed. If the 90th percentile of those intensities was less than the average background intensity plus 5 times the standard deviation of the background intensities, then the droplet was rejected. If the number of pixels-inside that had intensities greater than the average background intensity plus 3.5 times the standard deviation of the background intensities ($N_{3.5}$) was fewer than 4, then the droplet was rejected. The fraction of pixels-inside whose intensity was above the average background intensity plus 3.5 was also calculated ($F_{3.5}$). If $F_{3.5}$ was less than 0.10, the droplet was rejected. If $F_{3.5}$ was less than 0.15 and $N_{3.5}$ was less than 20, the droplet was rejected.

Figure 6B:
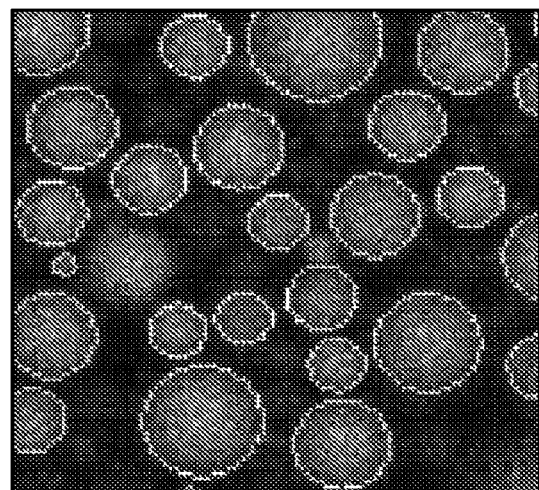
FIG. 6B shows the final results obtained after sorting circles in FIG. 6A to identify and locate droplets.

The procedure of this example was applied to the image in FIG. 1. The intermediate result of this method is shown in FIG. 6A and the best-fit circles for the droplets accepted is shown in FIG. 6B.

Example 6

Combined Reverse Watershed and Circle Detection Methods for Identifying Droplets This Example describes an exemplary process for performing the Combined Reverse Watershed and Circle Detection Methods according to an aspect of the present disclosure.

According to this aspect, the ROIs, Pixel Groups, and external boundary pixels were determined using the Reverse Watershed Method, after which the Circle Hough Transform was applied to the boundary pixels. By performing these methods in combination, additional criteria were applied in sorting the ROIs within a group into droplets. Three different cutoffs were defined for this example. The average and standard deviation of the background were calculated as described in Example 4. These will be referred to in this example as the initial average and initial standard deviations. The SCT for this example was the initial average plus 2.5 times the initial standard deviation. The cutoff for holes was the initial average plus 2.75 times the initial standard deviation. One further cutoff was applied to determine which pixels were parts of the background. The background cutoff was the initial average and 2.3 times the initial standard deviation of the background. The use of a smaller cutoff to define the background was to eliminate areas of the image that contained fluorescence that originated from other focal planes in the sample. All pixels whose intensities were less than the background cutoff were considered to be part of the final background.

In addition, all 4-connected sets of pixels with intensities greater than the background cutoff were examined. If the area of the set was less than 10 pixels, then those pixels were included in the final background. The pixels in the final background were used to calculate the final average background intensity that was used to obtain background subtracted intensities.

In this example the cutoff using the SCT was applied first to define groups, as in Example 5. In addition each Pixel Group was checked for 8-connected sets of pixels whose intensity was below the hole cutoff (HT) inside the Pixel Group. If the set contained nine or more pixels it was denoted a Hole. The list of any pixels within a Pixel Group that were adjacent to a Hole was added to the list of external boundaries of the Pixel Group. Then the Reverse Watershed method was applied to the image as in Example 4. By determining the Pixel Groups first, any ROIs found by the Reverse Watershed method were then immediately collected into the Pixel Group to which they belong. This was done for bookkeeping purposes and was not essential. The external boundaries of the ROIs were trimmed to eliminate noise pixels. The list of trimmed external boundary pixels includes only those external boundary pixels of the ROI that are adjacent to at least one interior pixel. An interior pixel is one that part of a Pixel Group, but is not adjacent to a non-group pixel.

The list of trimmed external boundaries is referred to below as the list of feature pixels. In contrast to Example 4, the Reverse Watershed method, the trimmed external boundary pixels of each ROI were not fit to a circle at this stage. Instead, the Circle Hough transform was applied to the list of feature pixels of each ROI. The transform was performed for circle radii ranging from 2 to 60 pixels for each Pixel Group. A modified method for performing the transform was used in this example due to the elevated level of noise in the image. The number of votes assigned to a pixel in this aspect was the weight assigned to the possibility that the pixel is the center of a circle of radius R. Ordinarily, for a given radius R, the number of votes assigned to a pixel would instead be the number of feature pixels within a distance R of the pixel. In this method it was the number of feature pixels within a distance R−1, R or R+1 of the center of the circle. The number of votes for a particular pixel and the list of feature pixels voting for each pixel were calculated for each value of R.

The list of circles generated for each ROI was reduced as follows: (i) if the fraction of the circle occupied by pixels that are not part of the Pixel Group to that the ROI belongs (non-Pixel Group pixels) exceeds 30% the circle is rejected; (ii) if the ratio of the number of non-Group pixels inside the circle to the circumference of the pixel exceeds 0.40 the circle is rejected; (iii) if the fraction of the circumference of the circle that are non-Pixel Group pixels exceeds 70% the circle is rejected and (iv) if the ratio of the non-Pixel Group pixels inside the circle to Pixel Group pixels inside the circle exceeds 0.30 the circle is rejected.

The pairs of circles with the same radius were then examined. If the distance between the centers of the circles was less than 50% of the radius (or less than 2 pixels for radii <5 pixels) then the lists of pixels voting for each of the two circles were compared. If there was an overlap of more than 30% (the number of votes in common with both circles is 30% or more of either of the two lists), then the circle with the smaller number of votes was rejected.

Next, the pairs of circles that could have different radii were examined. If the distance between the centers of the circles was less than 50% of the radius of the larger circle, then the lists of pixels voting for each of the two circles were compared. If there was an overlap of more than 30% (the number of votes in common with both circles is 30% or more of the list for the circle with the smaller radius) then the circle with the smaller radius was rejected.

The circles associated with an ROI at that point were sorted by the number of votes, starting with the largest number of votes. Then each circle was compared with all other circles associated with the ROI with fewer votes (referred to below as the circle A and B, respectively). If 50% or more of the votes for the circle B were also votes for circle A, then two additional checks were performed for that pair of circles. If 60% or more of the area inside the circle B was also inside circle A, then the circle B was rejected. If either circle overlapped the edge of the image, then the areas considered was only that portion of the area of the circle that was in the image. For the additional inquiry, the distance between the centers of the two circles was calculated. If this distance was less than 89% of the radius of the larger of the two circles, then circle B was rejected. The next step according to this aspect was to group ROIs into droplets using the circles identified for them.

If a Pixel Group had only a single ROI circle left at this point, then that circle was used to identify the external boundary pixels used to size the droplet.

If there were two or more circles a set of tests was then performed. For each circle the distance from its center to the centers of all other circles in the Pixel Group was calculated and then divided by the radius of the first circle ($\Delta C_{scaled}$) A list of all circle pairs was created and sorted by $\Delta C_{scaled}$ starting with the smallest. If $\Delta C_{scaled}$ for a pair of circles was less than 0.10 and the ratio of the difference in radius for the two circles to the radius of the smaller circle was less than 0.20, then the two circles (and the ROIs they are associated with) were assigned to be part of the same droplet. Any remaining circles at this stage that had not been assigned to a droplet were each assigned to a separate droplet. Next, a list of the votes associated with a droplet was created. This list of votes included all the votes for the circles assigned to the droplet. This list was then fit to a circle.

It is possible that a single ROI could have been assigned to more than one droplet. This was checked for and in those instances, the distance from the best-fit center of each droplet to the center of the circle associated with the ROI was calculated. The ROI was assigned to the droplet for which this distance was smallest and removed from the list of circles assigned to the droplet for which this distance was largest. This step of the example assumes that the each ROI found by the Reverse Watershed Method was only part of one droplet. If this step leaves a droplet without any ROIs assigned to it, then that droplet was rejected. A list of droplets associated with a Pixel Group was created and sorted by radius, starting with the largest radius. Then all pairs of droplets within a Pixel Group were compared. If 75% or more of the pixels inside the best-fit circle with the smaller radius were also inside the best-fit circle with the larger radius, then the droplet with the smaller best-fit radius was rejected and any ROIs assigned to the rejected droplet were assigned to the droplet with the larger radius.

Next, if there were any unassigned ROIs in the Pixel Group, they were checked to see if they should be assigned to an existing droplet. The pixels for circumference of a droplet (determined by fitting a circle to the droplet's votes) was dilated using MATLAB's imdilate( ) function and a structuring element defined by the MATLAB expression strel('square', 3) to produce a mask. For each unassigned ROI, if 50% or more of its trimmed external boundary pixels was within that mask, then that ROI was assigned to the droplet. The pixels of the ROI that were inside the mask were added to the votes for that droplet. Any droplet whose list of assigned ROIs was changed by these steps was refit to a circle. If a Pixel Group was then found to have no droplets associated with them at all, then the trimmed external boundary pixels were fit to a circle and the entire Pixel Group treated as one droplet.

In other aspects, alternate methods could be used to locate additional droplets within the image. If a Pixel Group had a significant number of pixels that were not inside a droplet, the external boundary pixels of any ROIs that were not already assigned to a droplet could be fit to a circle. Additional constraints can be applied in that in addition to not having a significant overlap with the non-group pixels, these additional circles can be constrained to not have significant overlap with existing droplets within the group.

The problem of the region between two droplets having elevated pixel intensities leading to a non-circular boundary was mitigated by the use of the Circle Hough Transform, since it discriminated against pixels that form a non-circular boundary.

Figure 7A:
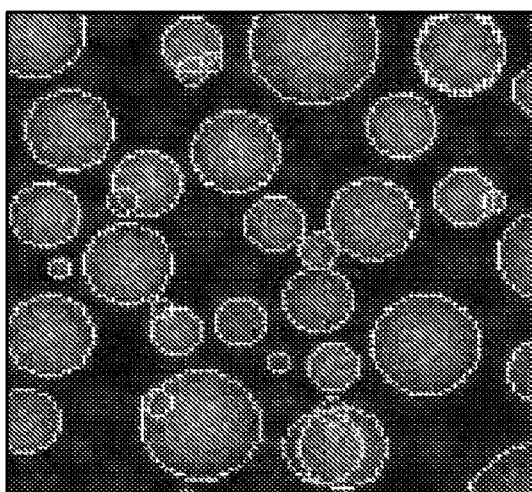
FIG. 7A shows a processed image produced after performing the initial steps of the combined reverse watershed and Circle Detection Method as applied to the image of FIG. 1.
Figure 7B:
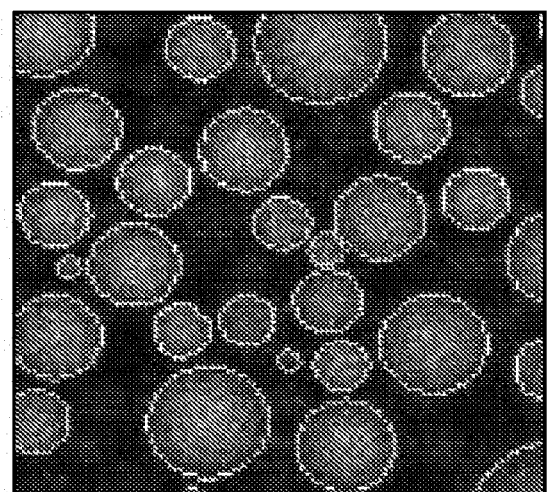
FIG. 7B shoes the final results obtained after sorting circles in FIG. 7A to identify and locate droplets.

FIG. 7A shows a processed image produced after the Reverse Watershed and Circle Hough Transform methods were applied to the image of FIG. 1 and unwanted circles rejected. FIG. 7B shows the final results obtained after sorting those circles to identify and locate droplets.

Example 7 dPCR Amplification and Analysis

This Example describes a method for dPCR amplification and analysis of a nucleotide sample using a polydisperse droplet emulsion system.

In order to visualize the presence of amplification products within a droplet, a fluorescence probe was added to the reaction mixture that specifically recognized the presence of the amplicon. A small amount (1-2 µM) of the red fluorescent dye 6-carboxy-X-rhodamine (ROX) was used as a reference dye in the reaction mix. The spectral signature of ROX is readily distinguished from that of a green fluorescence probe used to report amplification. Furthermore, the ROX fluorescent signal is insensitive to amplification or other reaction or reagent conditions. The ratio of two intensities, one measured from the reference dye and one measured from the probe, is used to make a binary measurement from each measured droplet. The intensity ratio is not affected by changes in droplet volume due to fusion or shrinkage, or unwanted changes in light excitation power, since each of these will affect fluorescence intensity of both dyes comparably, leaving the ratio unchanged.

In order to build a profile of the distribution of droplet sizes, the emulsion was transferred onto a 96-well plate, the surface of which was silanized, and covered with an excess volume of the oil-surfactant mixture. Emulsions were imaged using a Zeiss LSM 510 confocal microscope in multi-track mode with a PLAN APO 20×, 0.75 NA objective. Laser-source excitation wavelengths of 543 nm (LP 610) and 488 nm (BP 500-530) were used to collect fluorescence signals from the ROX and FAM dyes. For each field of view, a series of optical sections (z-stacks) were imaged at varying depths along the z-axis to build a 3D profile of droplet dimensions.

FIGS. 8A-8C illustrate a rapid method for verifying the presence of PCR amplification products in droplets during data acquisition. Circles in FIGS. 8A and 8B indicate identified droplets. Graphs on the right of FIGS. 8A and 8B depict fluorescence intensities along the straight lines depicted in the images on the left. Fluorescence intensity was measured across a line through the center of two droplets with similar diameters in the red fluorescent (ROX) and green fluorescent (FAM) channels (FIGS. 8A and 8B, respectively). Some, but not all, of the ROX-labeled droplets were also labeled with a green fluorescent DNA reporter. Both droplets had similar red fluorescence intensities whereas the green fluorescence intensity of droplet (2) was about 2.5 times greater than droplet (1). The lower signal of droplet (1) was consistent with background intensities generated by the TaqMan probe, which comprises the FAM fluorophore, indicating the absence of target DNA in droplet (1). The higher signal in droplet (2) observed in the FAM channel indicated that amplification took place in that droplet.

FIG. 8C shows the distribution of droplet diameters of 489 droplets measured after emulsification using the ROX fluorescence signal.

Figure 9:
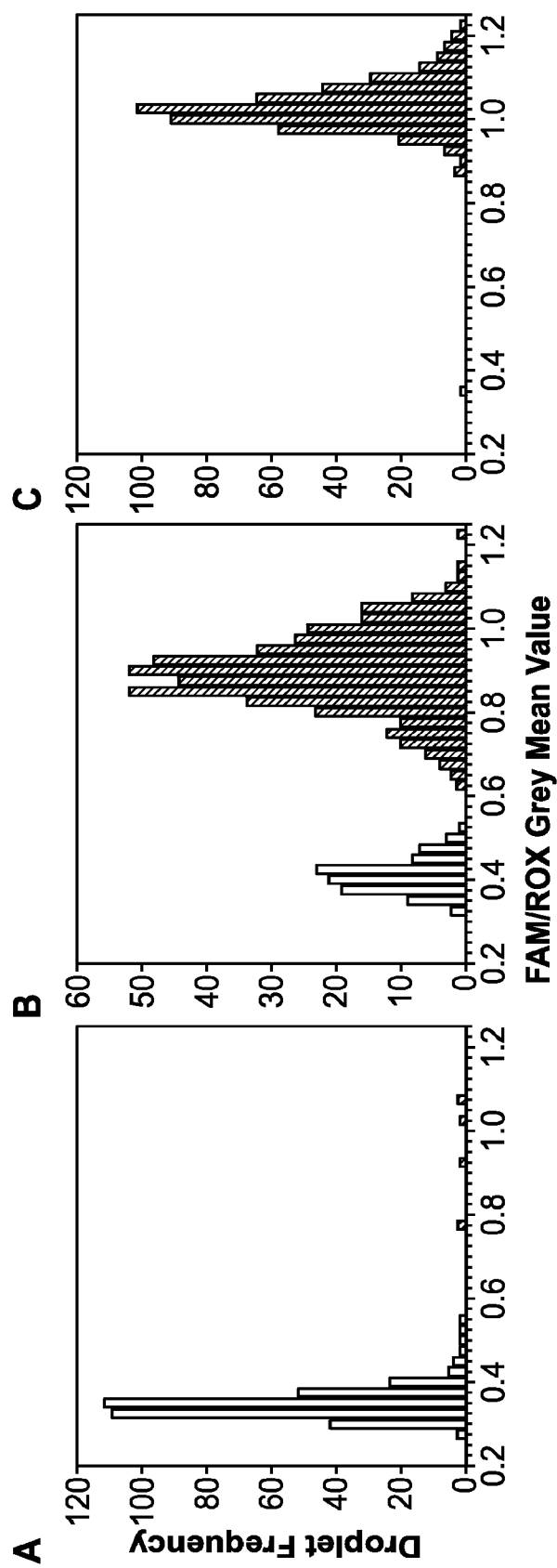
FIG. 9 shows the frequency distributions of the ratio of green-to-red fluorescence intensities for populations of polydisperse droplets loaded with three different starting concentrations of dsDNA (~$2\times10^3$ dsDNA copies/µL in Histogram 9A, ~$2\times10^6$ dsDNA copies/µL in Histogram 9B, and ~$2\times10^7$ dsDNA copies/µL in FIG. Histogram 9C).

FIG. 9 shows frequency distributions of the ratio of green-to-red fluorescence intensities for populations of polydisperse droplets loaded with three different starting concentrations of dsDNA (i.e., ~2×10³ dsDNA copies/µL in Histogram 10A, ~2×10⁶ dsDNA copies/µL in Histogram 10B, and ~2×10⁷ dsDNA copies/µL in Histogram 10C). At the lowest concentration, essentially no droplets contain an amplified DNA sample following PCR (Histogram 10A). This distribution consists mostly of droplets lacking amplified products with a mean FAM/ROX ratio of 0.35 (N=1701 droplets). At the middle concentration some droplets contain an amplified DNA sample following PCR, whereas others do not (Histogram 10B). At this initial target molecule concentrations (~2×10⁶ molecules/pL), two clear distributions are visible (Histogram 10C), corresponding to non-amplified droplets (white bars) similar to those shown in Histogram 10A, and amplified droplets (black bars) having FAM/ROX ratios greater than 0.625. This value is over 1.5 times greater than the mean of the non-amplified droplets, making it an appropriate threshold for distinguishing between droplets that do or do not contain amplified sample. At the highest concentration, essentially all droplets contain an amplified DNA sample following PCR (Histogram 10C). At even higher initial target molecule concentrations (~2× 10⁷ molecules/pL), almost all of the emulsion droplets have FAM/ROX ratios above the threshold for detection of amplified sample (Histogram 10C).

Example 8

Method for Droplet Analysis Following dPCR

This Example describes a digital amplification analysis method using continuous variable droplet volumes, such as digital PCR in a polydisperse droplet emulsion system. Using this method, a target sample concentration, $C_S$, can be accurately determined using digital assays with polydisperse droplets.

The sample is distributed into droplets of variable size and the distribution of target molecules into the droplets follows Poisson statistics. Although this example provides a method for calculating sample concentration, it will be understood that other suitable methods can be used to determine sample concentration. In this example, initial sample concentration ($C_S$) is expressed as a number of molecules in a given volume. The sample is distributed into discrete partitions or "droplets" of variable volumes, where the distribution of target molecules into the droplets follows Poisson statistics. For each droplet in the digital array, and as shown in Equation (5), the average number of targets depends on its volume, $V_i$, and the initial sample concentration, $C_S$:

$$P(n, C_S V_i) = \frac{(C_S V_i)^n}{n!} \exp(-C_S V_i) \quad (5)$$

$P(n, C_S V_i)$ is the probability of finding n molecules in a droplet of volume $V_i$ for a given concentration $C_S$ of target molecules in solution. The amplification reaction will cause a droplet containing one or more molecules to be distinguishable from empty droplets by means of a reporter, such as the fluorescence reporter described in Example 7. In this method, it is only known whether a droplet is empty (n=0) or occupied (n>0). The associated probabilities are shown in Equations (6) and (7) below:

$$P(0, C_S V_i) = \exp(-C_S V_i)$$

$$P(n>0, C_S V_i) = 1 - \exp(-C_S V_i) \quad (6) \, \& \, (7)$$

In order to determine the concentration, $C_S$, of target molecules, $P(n>0, C_S V_i)$ can be summed over a large number of droplets with respective volumes, $V_i$.

For each analysis step, a fixed number of droplets, $N_d$, is present, and those droplets have a given concentration of target molecules, $C_S$. Droplet diameters vary randomly and the size distribution for those droplets is shown in FIG. 10. This distribution is comparable to the experimental distribution measured in FIG. 8C. The distribution is a lognormal distribution in which only diameters between 8 and 64 microns are included.

The various droplets have a concentration, $C_S$, of target molecules, and in some instances, the concentration, $C_S$, can be zero, which is indicative of a lack of target analytes in a given droplet. The total number of droplets determined to contain target analyte, $N_S$, is counted and subsequently compared to the expected number of occupied droplets, $N_E$ as described in Equation (8) below:

$$N_E = \sum_{i=1}^{N_d} (1 - \exp(-CV_i)) \qquad (8)$$

The most probable value of $N_E$ is obtained for $C=C_S$. Using the volumes of the $N_d$ droplets, Equation (8) can be fit to $N_S$ to obtain a best-fit value of the concentration, with C being the only adjustable parameter. A Newton-Rhapson algorithm was used to find the zero of $N_S-N_E$. The initial value of C is obtained by replacing $V_i$ in Equation (8) with the median volume of the distribution and solving for C. The algorithm then typically takes 5-11 iterations for the changes in C to fall below one part in $10^5$. The value of C at that point is taken to be the best-fit value of C.

These calculations seek to determine how accurately this procedure estimates a given $C_S$, and if two different samples yield different best-fit values of C, then attempts to calculate the degree of confidence that the samples have different concentrations.

This method includes the measurement of the volume of each droplet and its associated error. Errors in droplet diameter can be approximated by a Gaussian-distributed error, which is applied to any given diameter measurement. Droplet diameters are used to calculate droplet volumes, and thus the error in the droplet diameters give rise to corresponding errors in the droplet volumes, $\hat{V}_i$, which are substituted into Equation (9) to yield the expected number of occupied droplets based on measured volumes.

$$\hat{N}_E = \sum_{i=1}^{N_d} \left(1 - \exp\left(-C\hat{V}_i\right)\right) \qquad (9)$$

In this example, droplet diameters are determined by microscopy. The accuracy of this method can depend on the numerical aperture (NA) of the objective lens used as well as other components of the imaging system. For imaging a large number of stationary droplets on a surface, the NA would likely be less than one and the error in diameter measurements is typically 0.5 to 1.0 microns, independent of the size of the droplet. Two different magnitudes of measurement error are considered and are denoted as $E_1$ and $E_2$. For $E_1$, the standard deviation of the Gaussian-distributed error added to a droplet diameter and is the larger of 1 micron or 8% of that droplet's diameter. The relative error is included so that the calculation includes a non-negligible measurement error for the largest droplets. For $E_2$, the standard deviation of the Gaussian-distributed error added to a droplet diameter is the larger of 2 microns or 15% of that droplet's diameter. In both cases there is one limit placed on the measured diameters. If a particular droplet diameter with measurement error results in the diameter being less than 0.5 microns, then that measurement error is discarded and a new one is generated for that droplet. The result is an unbiased measurement error.

$C_S$ is the actual, unknown concentration that the procedure is attempting to determine, and $\hat{V}_i$ s are the volumes measured by the experimenter. C is varied until $\hat{N}_E$ in Equation (9) equals the measured number of occupied droplets to obtain the best-fit concentration.

Calculations are performed with $C_S=4.4\times10^{-5}$ molecules/fL and $N_d$ ranging from 500 to 10000. The droplet sizes were drawn from the distribution of diameters shown in FIG. 10, which depicts a clipped lognormal distribution of droplet diameters used to validate methods for performing digital assays. The calculations are repeated for the case of no measurement error ("0 error") in the droplet diameters and $E_1$ and $E_2$ measurement error. For each number of droplets and amount of error, 1000 calculations are performed and the average best-fit concentration and the standard deviation of the distribution of best-fit concentrations are calculated.

Figure 11:
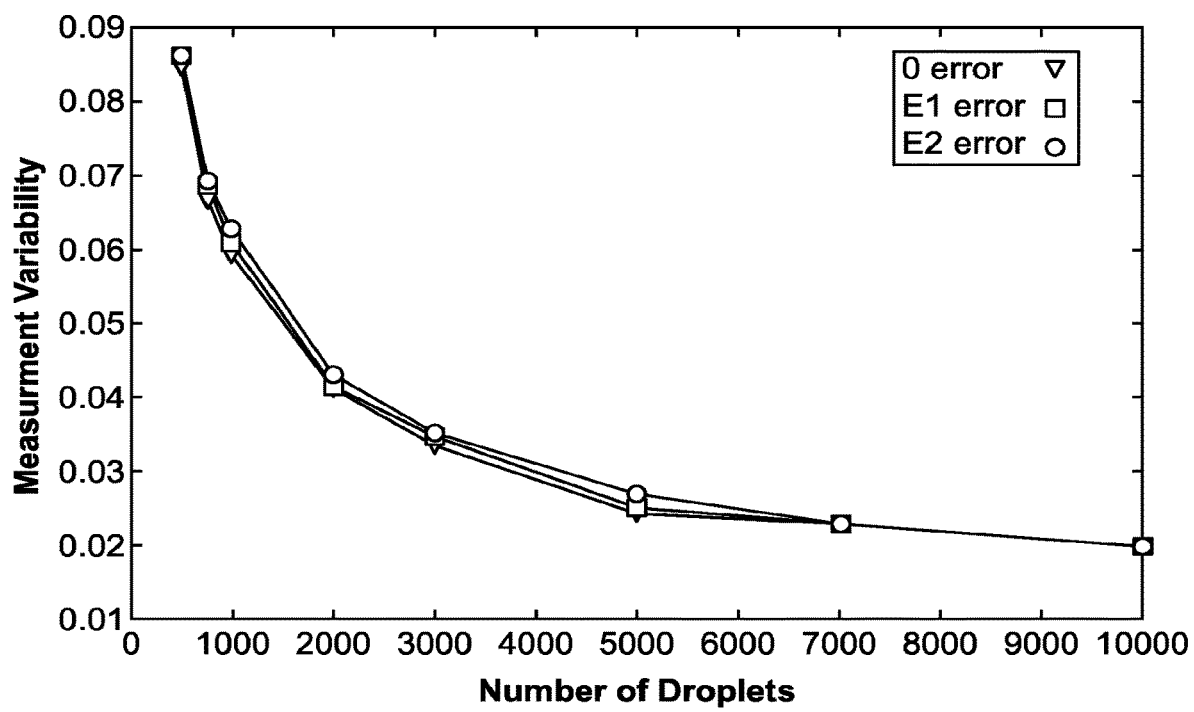
FIG. 11 shows the relationship between sample size (i.e., number of droplets, shown on the horizontal axis), errors in droplet diameter measurements, and errors in the measurement of a sample concentration (measurement variability, shown on the vertical axis). Data were generated using computer simulations of a digital assay performed with the sample concentration set to $4.4\times10^{-5}$ molecules/fL.

The ratio of the standard deviation to the average best-fit concentration is called the "Measurement Variability" and is plotted for the range of droplet numbers and amount of measurement error in FIG. 11. FIG. 11 shows how measurement variability is affected by sample size (i.e., number of droplets). Data are generated for a digital assay performed with the sample concentration set to $4.4\times10^{-5}$ molecules/fL. Measurement variability reflects the accuracy of a digital assay in estimating the true concentration of a sample, with more measurement variability implying less accuracy. For this simulation, measurement variability (vertical axis) is defined as the ratio of the standard deviation divided by the mean of the estimated concentration distribution. Measurement variability is calculated for different numbers of droplets (drawn from the droplet diameter distribution shown in FIG. 10), and for three different amounts of error in the simulated measurement of droplet diameters. In one set of calculations, the measurement of droplet diameters had no errors ("0 error"). In another set of calculations, the standard deviation of the droplet diameter error distribution is the larger of 1 μm or 8% of the true droplet diameter ("$E_1$ error"). In a third set of calculations, the standard deviation of the droplet diameter error distribution is the larger of 2 μm or 15% of the true droplet diameter ("$E_2$ error"). The similarity in the measurement variability for the three different amounts of droplet diameter measurement errors suggests that the measurement variability for any given sample is dominated by the Poisson statistics, which govern the distribution of target molecules among the droplets. As a result, any variability in the best-fit concentration due to droplet-size measurement errors has a small or negligible impact on the concentration determination, so long as it is unbiased.

The ability of a method to distinguish a difference in concentrations can be described in terms of confidence and power. This aspect is described by Lieber, R. L. (1990) "Statistical Significance and Statistical Power in Hypothesis Testing," J. Orthopaedic Research 8, 304-309. The present method enables one to determine the confidence level for a given measurement, which is particularly relevant when measurements on two different samples yield two different best-fit concentrations ($C_1$ and $C_2$). Thus, it would be useful to know how confident one can be in asserting that the concentrations of the two samples are different, and also the probability of being wrong if one concluded that they were not different. The risk of a false positive result (Type I error) is controlled by requiring that the results have a required minimum confidence and the risk of a false negative result (Type II error) is controlled by requiring that the method have a required power.

For the comparison of two best-fit concentrations from two different samples, the null hypothesis would be that the two samples have the same (unknown) concentration. If a is the probability that two samples with the same concentration can result in best-fit concentrations that differ in magnitude by more than $|C_1$ and $C_2|$, then $(1-\alpha)$ is the confidence associated with rejecting the null hypothesis. The acceptable minimum value of $(1-\alpha)$ is chosen to limit false positive results. The use of the power to guard against false negatives is described below.

One method used to estimate confidence levels is the Z-test as shown in Equation (10):

$$Z = \frac{C_1 - C_2}{\sqrt{\sigma_1^2 + \sigma_2^2}} \qquad (10)$$

A confidence level of 95% is a common choice and requires $Z > 1.96$. The value of $C_n$ is derived from the best-fit results of Equation (9), and $\sigma_n^2$ is the variance associated with the measurement of $C_n$. In this example, $\sigma_n^2$ is estimated because it is believed that there is no tractable analytical expression for this term. A second simulation method to estimate the confidence is performed and compared with the Z method results. Hereafter, the two methods are denoted the Z method and the Pairs method (or P method).

For the Z method estimate of the confidence, two different values of $C_S$ are used ($C_{S1}$ and $C_{S2}$). For $C_{S1}$, a set of 5000 droplets is randomly selected from the clipped lognormal distribution and Equation (6) is used to calculate the number of occupied droplets. The $E_1$ size of measurement errors is used to generate volumes, $\hat{V}_i$. A best value of the concentration, $C_1$, is obtained using Equation (8) as described above. The standard deviation is estimated by performing $N_Z=1000$ additional calculations. For each, the amount of variability due to Poisson statistics is determined by taking the set of measured volumes, $\hat{V}_i$ and using Equation (6) to determine which of them is occupied. The number occupied are then fit using Equation (8) to obtain a best-fit concentration for each additional calculation. The standard deviation of the additional $N_Z$ calculations is used for $\sigma_1$ in Equation (9). This process is then repeated for $C_{S2}$. An estimate of the confidence can be calculated from the best-fit concentrations, $C_n$, and the measured droplet volumes $\hat{V}_i$ using Equation (9).

For the P method estimate of the confidence, the null hypothesis is that the two best-fit results ($C_1$ and $C_2$) are each obtained from a sample whose actual concentration, $\overline{C}$, is the average of the two best-fit concentrations. $N_p=500$ additional sets of droplet diameters are determined and for each, the number of occupied droplets are determined for the concentration, $\overline{C}$, and the $E_1$ size of measurement errors are used to generate measured volumes. A best-fit concentration $\overline{C}'$ is obtained for each set. Then $M_p=500$ pairs of values are randomly selected with replacements from the set of $\overline{C}'$ and the absolute value of their differences ($\delta\overline{C}'_p$, p=1, ..., $M_p$) are compared with $\Delta C = C_2 - C_1$. The fraction of the $\delta\overline{C}'_p$ that are greater than $\Delta C$ provides an estimate of $\alpha$, i.e., the probability that two measurements made from a sample with concentration $\overline{C}$ would differ from each other by more than $\Delta C$. The P method estimate of $\alpha$ is used to calculate the confidence, which equals $(1-\alpha)$.

The entire procedure for obtaining two estimates of the confidence is repeated for pairs of $C_S$ values 100 times. For each repetition, a new set of volumes is generated for each $C_S$ and Equations (6) and (7) is used to generate the number of occupied droplets for each $C_S$. Measured volumes are generated and used in Equation (9) to fit the results and obtain a new pair of best-fit concentrations ($C_1$ and $C_2$). The difference between confidences calculated for a given pair of measurements by the Z method and P methods are typically less than 1%, so either method can be used to calculate the power. One advantage of the Z method for analyzing measurements is that it does not require a numerical method for generating distributions of droplets.

Figure 12:
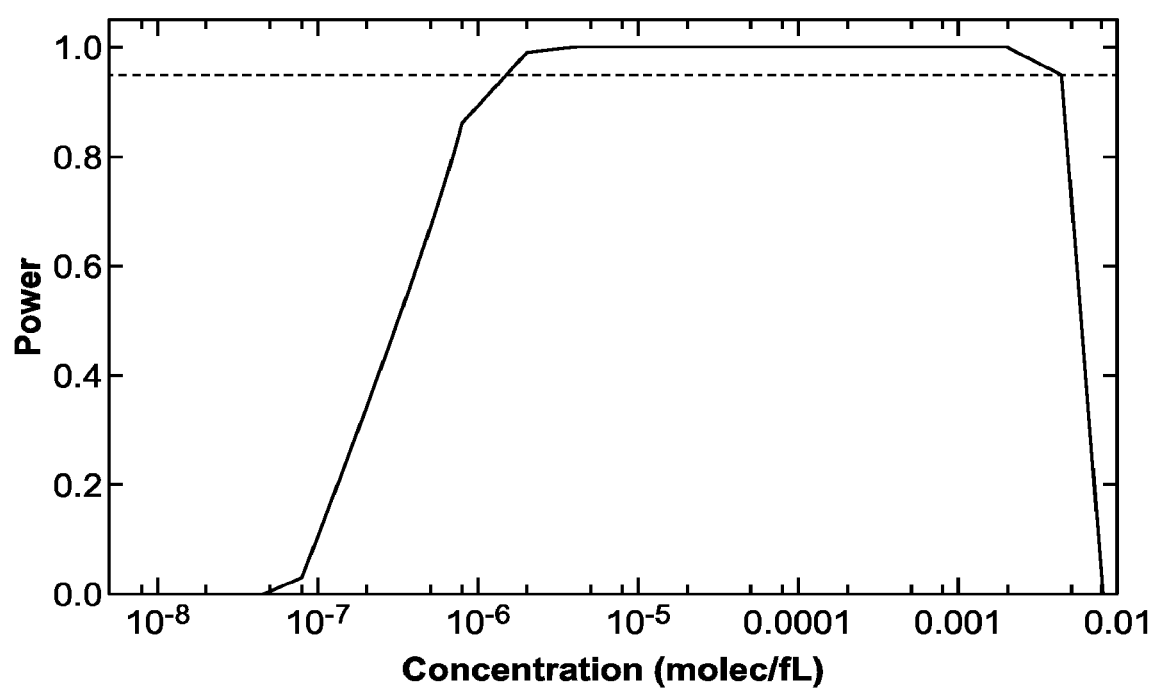
FIG. 12 shows the relationship between sample concentration and the statistical power with which a sample of a given concentration can be distinguished using a digital assay from a second sample having a concentration that is 50% higher.

The P method can also be used to analyze measurement values. For two different concentrations, the power is the fraction of the results that exceeds a desired value of the confidence, $(1-\alpha)$. Determinations of the power in distinguishing two concentrations that differ by 50% are performed using $N_d=5000$ droplets and $E_1$ measurement error. The results are plotted in FIG. 12 as a function of the smaller of the two concentrations. In FIG. 12, the standard deviation of droplet diameter measurement error is the larger of 1 µm or 8% of the droplet diameter ("$E_1$ error"). The dashed line marks a power of 0.95, which corresponds to a 5% chance of failing to detect a difference in the two sample concentrations (a false negative, or Type II error). The solid line is the power for distinguishing the case of two concentrations that differ by 50% when the confidence level, $(1-\alpha)$, equals 0.95. For a confidence level of 95% (which discriminates against false positives or Type 1 error) the dynamic range is defined as the ratio of the maximum and minimum concentrations for which the Type 2 error (i.e., false negatives) is 5% or less (power >0.95). This point is seen in FIG. 12 at the ratio of the larger concentration where the solid and dashed lines cross divided by the smaller concentration where the solid and dashed lines cross.

Figure 13:
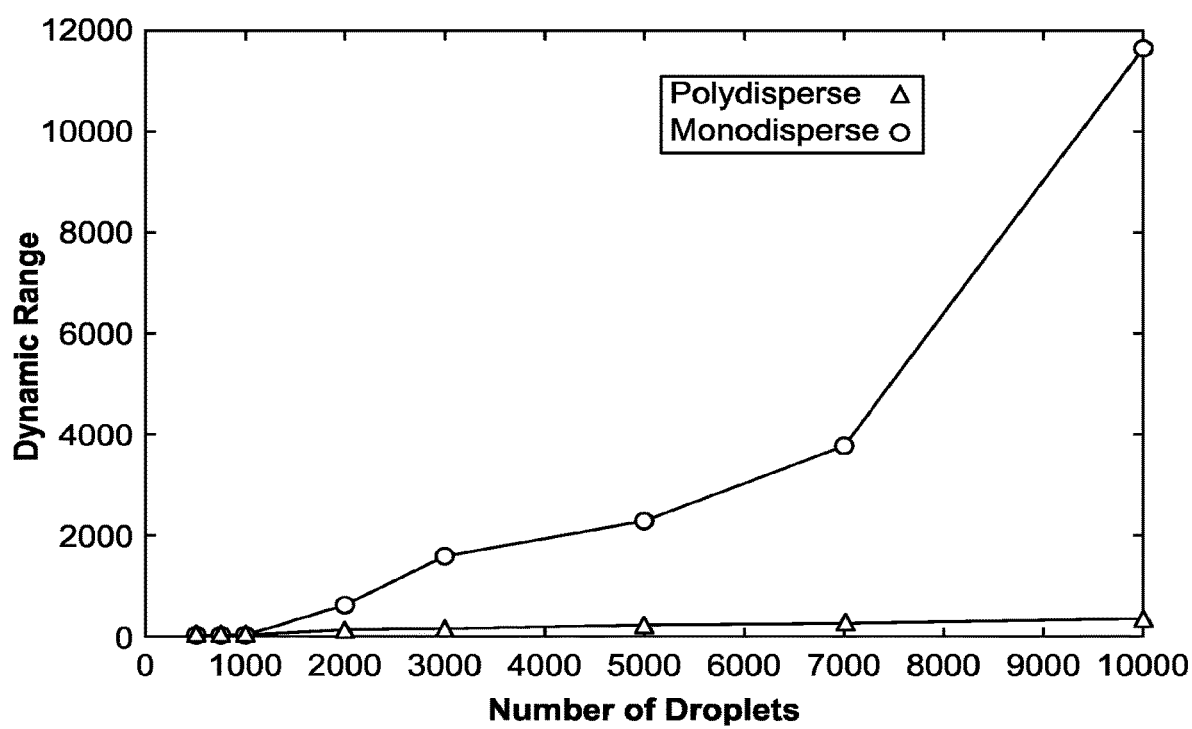
FIG. 13 shows the relationship between sample size (number of droplets, shown on the horizontal axis) and dynamic range (shown on the vertical axis) of a digital assay when performed on polydisperse droplets (gray circles) or monodisperse droplets (black triangles) with no droplet diameter measurement error.

FIG. 13 is a graph depicting the relationship between sample size (number of droplets, shown on the horizontal axis) and dynamic range (shown on the vertical axis) of a digital assay when performed on polydisperse droplets (gray circles, diameters obtained from the distribution in FIG. 10) with droplet diameter measurement error ("$E_1$ error") or monodisperse droplets (black triangles, all diameters exactly 30 µm) with no droplet diameter measurement error. The dynamic range describes how broad the range of concentrations is for which the assay can be used effectively. Specifically, the dynamic range is defined as the ratio of the maximum and minimum concentrations for which statistical power is greater than 0.95, assuming a confidence level of 95% (5% chance of a false positive, or type I error). The digital assay is effective for a much broader range of concentrations when it is performed on polydisperse droplets compared with monodisperse droplets. As shown in FIG. 13, for the same number of droplets, the digital assay has a significantly larger dynamic range when using a distribution of polydisperse droplets than can be obtained using a distribution of monodisperse droplets. For this reason, the use of polydisperse droplets is analytically superior to the use of monodisperse droplets.

FIG. 1 is a gray-scale image of an exemplary polydisperse droplet emulsion system obtained using confocal fluorescent microscopy.

FIGS. 5A and 5B depict the results of the initial steps of the Reverse Watershed Method as applied to the image in FIG. 1, including the identification of regions of interest (ROIs) as shown in FIG. 5A and the final, processed image with optimized circular regions as shown in FIG. 5B, from which information on droplet size and target molecule presence can be determined.

FIG. 6A shows a processed image produced after performing the initial steps of the Circle Detection Method as applied to the image of FIG. 1. FIG. 6B shows the final results obtained after sorting circles in FIG. 6A to identify and locate droplets.

Example 9

Characterization of Droplet Diameter Changes

This Example describes the analysis of changes in the distribution of droplet sizes in a polydisperse droplet emulsion system under PCR conditions and methods for minimizing the impact of such changes.

Droplet size can change for a number of reasons, including as a result of evaporation or droplet fusion. Droplets in an emulsion system can experience significant temperature fluctuations, such as those that occur in PCR thermal cycling. Evaporation may occur within the droplets over the course of thermal cycling, which can alter the distribution of droplet diameters and volumes. Further, droplets sitting in proximity to one another may in some instances fuse with each other due to the tendency to reduce the overall surface tension of the droplet-containing system. Changes in droplet diameter and volume over the course of a digital assay can lead to measurement error if the change is significant. This Example sets forth steps to characterize and optimize the measurement system and ensure the accuracy of the size distribution measurements, including investigating the effects of heating and mechanical manipulation on droplet sizes.

Droplet Fusion. Two emulsions were prepared using a mixture of general PCR reagents. The first emulsion excluded both a DNA template and a green fluorescent probe (FAM), while the other emulsion excluded both a DNA template and a red fluorescent dye (ROX). In the latter, the final concentration of the green fluorescent probe (FAM) was increased to 1.4 µM. The two emulsions were allowed to settle and stabilize for 10 min. Then they were gently re-suspended and combined with slow tilting motions of the tube. Lastly, the combined mixture was aliquoted into three PCR tubes. The first tube was set off to the side as a no-heating (control) sample. The remaining two were thermal cycled under standard conditions the following cycling durations (including a hot start): 1 or 50 cycles. A replicate set was run concurrently.

Figure 14:
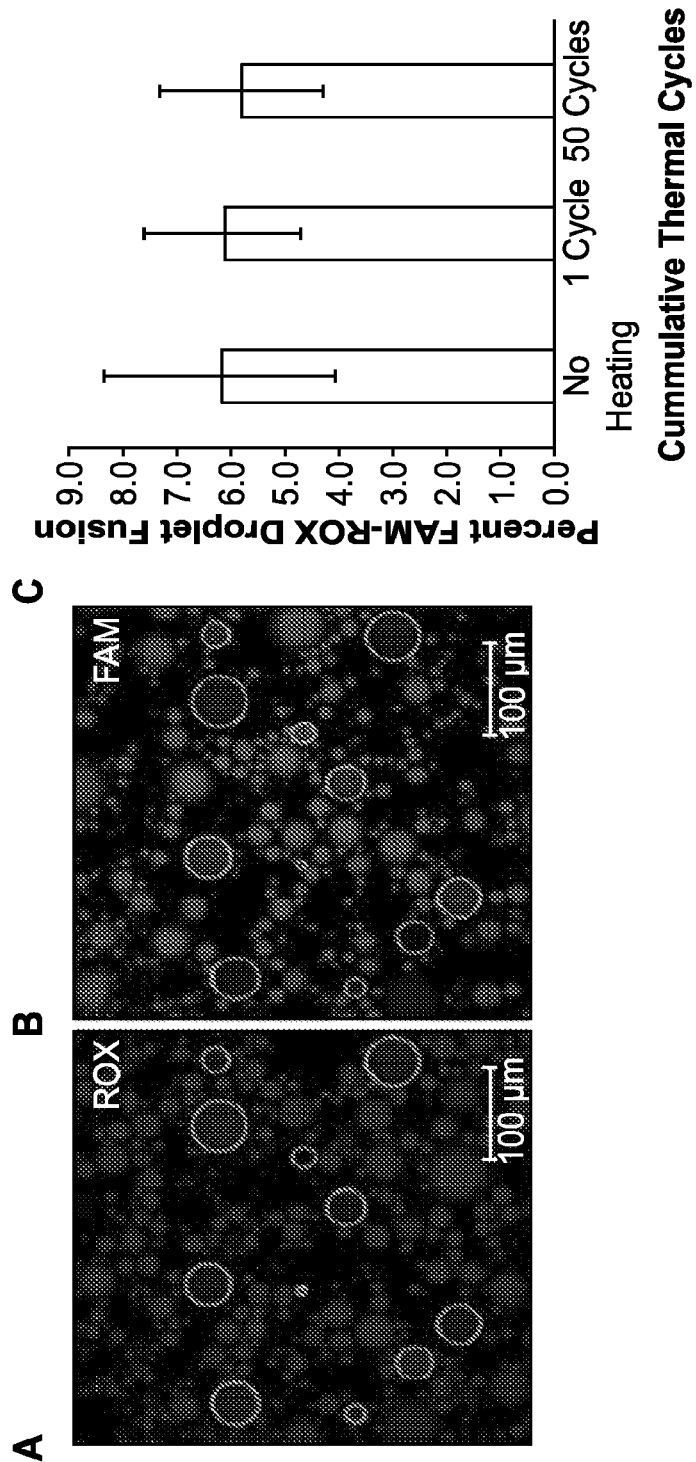
FIG. 14 shows the frequency of droplet fusion events that occur either spontaneously, or as a result of thermal cycling, in polydisperse droplet emulsions. Emulsified droplets containing ROX but no green fluorescent probe were combined with droplets containing green fluorescent probe but no ROX. The combined mixture, shown in Image 14A (red fluorescence) and Image 14B (green fluorescence), was then either left at room temperature to serve as a control (no heating) or was subjected to a hot start and one of 1 or 50 thermal cycles. The frequency of droplet fusion events is reflected in the percent of droplets containing both ROX and green fluorescent probe (Chart 14C).

FIG. 14 shows the frequency of droplet fusion events that occurred either spontaneously, or as a result of thermal cycling, in polydisperse droplet emulsions. The ROX and FAM fluorescence intensities of the emulsion mixture were used to identify fusion events. The frequency of droplet fusion events is reflected in the percent of droplets containing both ROX and green fluorescent probe. Droplets denoted with a circle contained both dyes (Image 14A and Image 14B). FAM and ROX fusion events solely due to post-emulsification droplet instability, sample handling, and pipetting were shown to be minimal, i.e., at a rate of 6.2±2.1% (Chart 14C). It should be noted that this measurement does not include fusion events between droplets containing the same dye, but it would be expected to be comparable in value. After a hot start and one thermal cycle, heating applied to the emulsion sample resulted in comparable fusion events of 6.1±1.4% (Chart 14C). The FAM-ROX fusion events detected for 50 cycles, 5.8±1.5%, was also similar to that of one cycle (Chart 14C). Both heating conditions were well within the range of error of the control aliquot.

It is important to note that fusion events did not appear to progressively increase with respect to thermal cycling duration. This suggests that thermal cycle heating induced little to no droplet fusion, and the main factors contributing to droplet instability were related to the mixing of the two color emulsions and sample handling. This is significant because fusion events that occur before or early during thermal cycling will not skew the results of the assay, since merged droplets that contain at least one target molecule will undergo amplification and give a positive signal, whereas merged droplets that do not undergo amplification will give a negative signal. In contrast, fusion events occurring later during thermal cycling can result in a merged droplet falling below the binary detection threshold of an assay, resulting in the droplet being incorrectly characterized. The results of the experiment indicate that fusion should have a minimal effect on sample quantification using this method. Additionally, if sample handling were to be entirely eliminated from the process by performing emulsification and thermal cycling all on the same device, fusion can have even less of an impact on the results of the assay. An example of a potential workflow eliminating sample handling post-emulsification is shown in FIG. 4.

Figure 15:
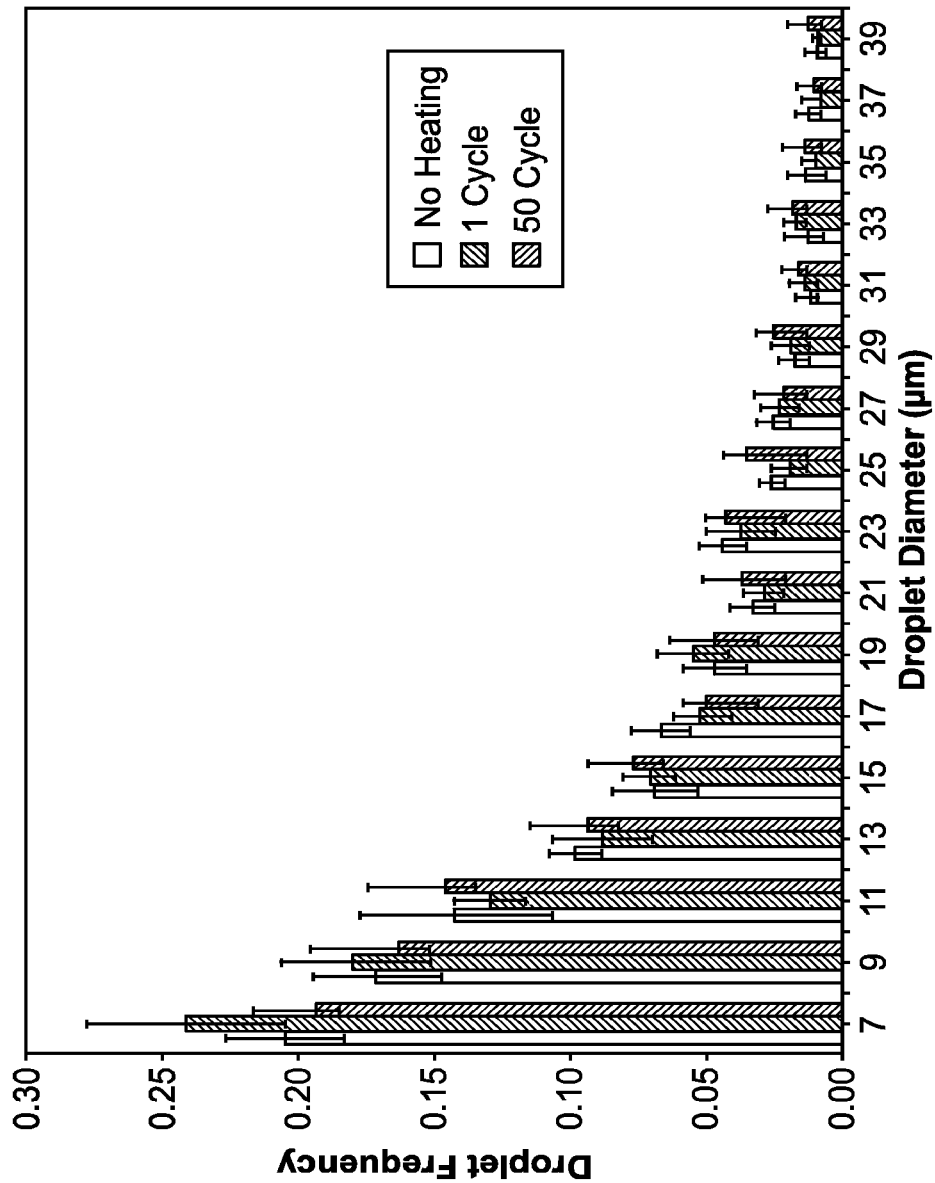
FIG. 15 shows the frequency of polydisperse droplet diameters subjected to no heating (white bars), 1 (gray bars) or 50 thermal cycles (black bars).

Droplet Shrinkage. Analysis of droplet shrinkage was carried out by comparing the droplet size distribution of a negative control and thermal cycled emulsion sample. Emulsions were prepared using the standard PCR mix and emulsification process. The same thermal conditions as the fusion experiments were examined. The droplet diameter distribution of the emulsion samples were normalized and plotted in FIG. 15, which compares the distribution of droplet diameters in polydisperse droplet emulsions subjected to either no heating, 1, or 50 thermal cycles. This experiment was conducted to quantify changes in droplet size resulting from repetitive thermal cycling. The control set had a mean diameter of 15.4±0.1 µm (1857 droplets measured). Polydisperse droplet emulsions subjected to one thermal cycle (triangles in FIG. 15) had a mean diameter of 14.9±0.4 µm (1952 droplets measured). Polydisperse droplet emulsions subjected to 50 thermal cycles (circles in FIG. 14) had a mean diameter of 15.8±0.5 µm (1660 droplets measured). The distributions of droplet diameters for the three conditions were indistinguishable, indicating that thermal cycling does not result in appreciable changes in droplet volume.

Example 10

Comparison Between Best-Fit Concentrations and Concentrations Determined by UV Absorbance This Example describes the good agreement observed between sample concentrations determined by best-fit methods of the present disclosure and those measured by UV absorbance.

The best-fit concentrations of serial dilutions of erbB2 dsDNA were compared with concentrations determined by absorbance measurements at 260 nm. The concentrations spanned a range of four orders of magnitude (i.e., $2\times10^3$, $2\times10^4$, $2\times10^5$, and $2\times10^6$ dsDNA copies/µL) with multiple samples at each concentration. The droplet diameters were determined using the Simple Boundary Method as described herein and the analysis included droplets with diameters ranging from 7 to 50 µm (1 to 500 pL volumes). Additional PCR parameters were consistent with those described in EXAMPLE 7. The best-fit concentrations were obtained using Equation (8) below:

$$N_E = \sum_{i=1}^{N_d}(1 - \exp(-CV_i)) \tag{8}$$

Figure 18:
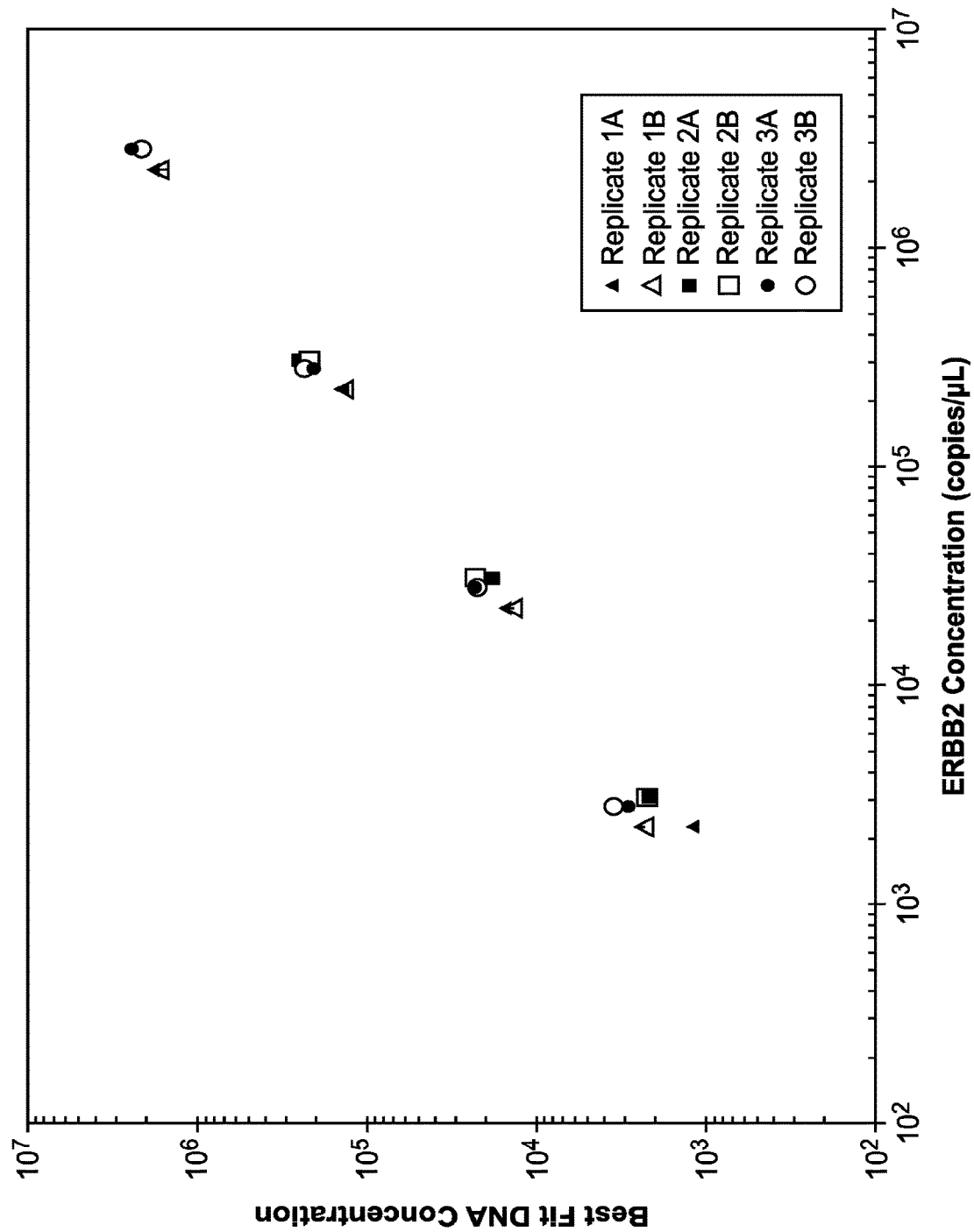
FIG. 18. shows the relationship between sample concentration values as determined by a best-fit method (shown on the vertical axis) and as determined by absorption measurements at 260 nm (shown on horizontal axis) for samples loaded with concentrations of dsDNA spanning four orders of magnitude ($2\times10^3$, $2\times10^4$, $2\times10^5$ and $2\times10^6$ dsDNA copies/µL of purified dsDNA).

FIG. 18. is a graph depicting the relationship between sample concentration values as determined by a best-fit method (shown on the vertical axis) and as determined by absorption measurements at 260 nm (shown on horizontal axis) for the erbB2 dsDNA samples described above. The comparison in FIG. 18 shows the good agreement between the two methods as indicated by the linear relationship between them.

Example 11

Droplet Analysis Using the Most Probable Number Method

This Example describes the use of the Most Probable Number (MPN) Method for determining the concentration of a target sample (by contrast to using Equation (8) as described in EXAMPLE 8). Using this method, the concentration, $C_S$, of a target sample is accurately determined without identifying, sizing or enumerating unoccupied droplets.

For the specific case involving chambers and wells, the number of chambers or wells containing the target sample was first determined. The number of chambers was predetermined before the assay was performed. The volume of each chamber was one of a discrete set of sizes, which were also predetermined before performing the assay.

For the specific case involving chambers and wells, the MPN equivalent of Equation (8) is shown below as Equation (11):

$$\sum_{i=1}^{m} n_i V_i = \sum_{i=1}^{m} \frac{(n_i - b_i)V_i}{(1 - \exp(-V_i C))} \quad (11)$$

In Equation (11), there are m different sizes of chambers. For the ith size, the volume of each chamber was $V_i$ and there were n chambers of that size. After the reaction was run, $b_i$ is the number of chambers of the ith size that were unoccupied. The equation was then fit to obtain C, the concentration of the solution.

In this method involving droplets, the left-hand term in Equation (11) is the total volume of all the droplets. The droplets all have different sizes so each of the $n_i$ is equal to one and the sum of all the $n_i$ equals the total number of droplets. There were m different sizes, and a summation was performed for all droplets. Because $b_i$ is one for an unoccupied droplet and zero for an occupied droplet, the $(n_i-b_i)$ term causes the sum on the right-hand side of Equation (11) to be a sum over only occupied droplets, and thus Equation (11) can be simplified and represented as Equation (12) below:

$$V_{total} = \sum_{i=1}^{m} \frac{O_i V_i}{(1 - \exp(-V_i C))} \quad (12)$$

where $O_i$ is one for occupied droplets and zero otherwise. This equation can also be solved iteratively for C. Simulations performed using Equation (12) and Equation (8) yield nearly identical results with the differences being less that the statistical errors in the fit.

As mentioned above, the terms in the sum of Equation (12) are zero for unoccupied droplets. Thus, if the total volume of the sample is known, then it is possible to identify and determine the size of the occupied droplets in the sample, after which Equation (12) can be used to determine sample concentration. According to this method, there is no need to identify the presence or size of unoccupied droplets.

Two different fluorescent dyes are used in methods that require sizing both occupied and unoccupied droplets. For example, Dye 1, which is fluorescent in all droplets, is used to size the droplets and Dye 2, which only fluoresces significantly in occupied droplets, is used to determine if the droplet is occupied. However, in a further aspect of the Example, using Equation (12) it is possible to execute the method described in this Example using only Dye 2. Thus, the fluorescence of Dye 2 is used to identify both the presence and size of occupied droplets.

When the concentration is small, the number of occupied droplets is correspondingly small In that case, a significant volume of emulsion is scanned for the modest number of occupied droplets. Because this method requires only that occupied droplets need to be sized, there are significantly fewer droplets requiring analysis, which in turn significantly reduces the analysis time of the method. In addition, at low concentrations, it is unlikely that two occupied droplets would touch each other. Because few analyzed droplets are touching, fewer calculations distinguishing those droplets are required. Thus, the computational requirements are significantly reduced using this method, thereby simplifying the process of scanning larger sample volumes for droplets. The ability to more easily scan larger volumes simplifies the analysis of low concentration samples, thereby increasing the method's sensitivity.

The Most Probable Number (MPN) Method described in this Example can be combined with the other methods described herein, with the modification that when using the MPN Method, there is no need to analyze the images of the unoccupied droplets. Any of the image processing algorithms described in the present disclosure can be used in combination with the MPN Method of this Example, for instance, by setting the threshold pixel intensity to exclude droplets lacking the target sample and analyzing only those containing the target sample.

Example 12

Index Matching to Improve Imaging Depth

In this Example, the benefits of matching the refractive indices of two or more immiscible fluids for purposes of optical imaging an emulsion system are described.

The ability to match the refractive index of the fluids that make up the discrete phase and continuous phase can enhance the data acquisition capabilities. When the refractive indices do not match, the illumination (or imaging) path can be deflected or distorted, leading to a loss of signal during data acquisition. The curved surfaces of the emulsion droplets become microlenses that diffract and scatter illumination, and imaging deeper into the solution increased the severity of aberrations in acquired data. In effect, the droplet boundaries became less discernible from the increasing number of overlapped droplets the illumination source must travel through as the plane of view is focused deeper (Z dimension) into the sample (FIG. 16, A1-A5).

Figure 16:
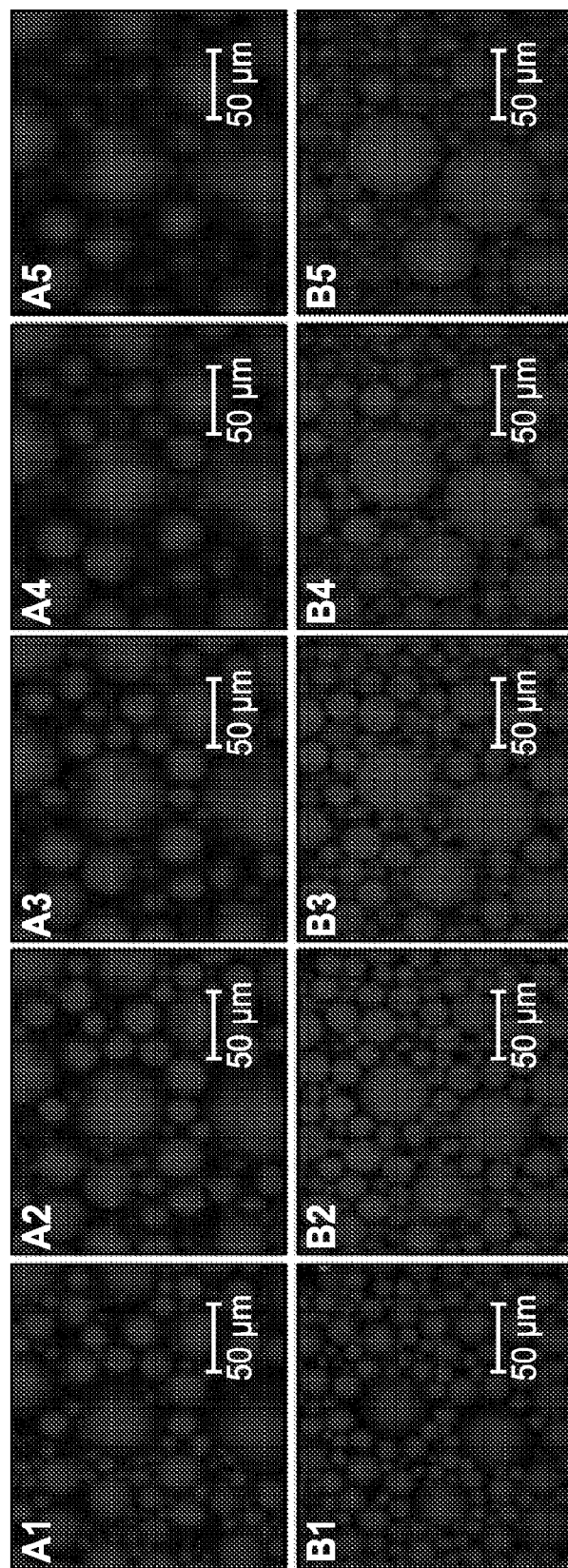
FIG. 16 shows the improvements in data acquisition capabilities achieved with refractive index matching of the fluids making up a polydisperse droplet emulsion. Fluorescence images were acquired at progressively deeper (from left to right) focal planes from two different emulsion systems (depicted in FIG. 16, A1-A5 and FIG. 16, B1-B5, respectively) with a confocal microscope. In the aqueous sample (FIG. 16, A1-A5), the refractive indices of the two immiscible fluid components are disparate, and the droplet boundaries become progressively less clear in images acquired at deeper planes of focus, as in FIG. 16, A5. In the mixed water and glycerol sample (FIG. 16, B1-B5), the refractive indices of the two immiscible fluid components are similar, and the droplet boundaries remain clear even in images acquired at deeper planes of focus, as in FIG. 16, B5.

FIG. 16 shows the improvements in data acquisition capabilities that were achieved with refractive index matching of the fluids making up a polydisperse droplet emulsion. Fluorescence images were acquired at progressively deeper (from left to right) focal planes from two different emulsions (depicted in FIG. 16, A1-A5 and FIG. 16, B1-B5, respectively) with a confocal microscope. Both emulsions were made using 73% Tegosoft DEC, 20% light mineral oil, and 7% Abil WE09 oil mix (refractive index ≈1.4) as the continuous carrier phase. For FIG. 16, A1-A5, the droplets were composed of PCR reagents dissolved in aqueous solution (refractive index=1.33). For FIG. 16, B1-B5, the droplets were composed of PCR reagents dissolved in a water (50% by weight) and glycerol (50% by weight) mixture (refractive index=1.398). In the aqueous sample (FIG. 16, A1-A5), the refractive indices of the two immiscible fluid components are disparate, and the droplet boundaries become progressively less clear in images acquired at deeper planes of focus, as in FIG. 16, A5. In one aspect the significantly higher refractive index of the oil mixture (n≈1.4) compared to water (n=1.33) led to a series of index matching tests involving the addition of high index components, such as glycerol (100% (w/w), n=1.474) and sucrose (65% (w/w), n=1.4532), to the PCR mix. In the mixed water and glycerol sample (FIG. 16, B1-B5), the refractive indices of the two immiscible fluid components are similar, and the droplet boundaries remain clear even in images acquired at deeper planes of focus, as in FIG. 16, B5.

Fluorocarbon oil emulsion systems were also investigated in an attempt to better match their refractive indices. While mineral oil systems have a refractive index significantly higher than water, fluorocarbon systems typically have a refractive index slightly lower than water (e.g., perfluorodecalin, Fluorinert FC-40, Fluorinert FC-70, Krytox, —see Table 1 above). Perfluorinated compounds that contain aromatic groups typically have refractive indices higher than water, so in this system the composition of the oil can be altered to improve the index matching. An oil phase containing 45% (v/v) Fluorinert FC-40 with κ% Pico-Surf 1 and 55% (v/v) octafluorotoluene mixed with PCR aqueous phase was investigated. The mixture was vortexed at 3000 rpm for 30 s. Due to the lower density of the water compared to the fluorocarbon oil phase (see Table 1), the w/o droplets floated above the oil phase. While this required removal of excess oil to image the w/o droplets within the working distance of the microscope, this combination improved the image quality of z-sections acquired deeper in the sample. The boundary distortions of droplets was much reduced and allowed for a greater range in building the 3D profile of droplet dimensions.

Attempts were made to minimize changes in the boiling point of any oil-phase components, which should remain inert at temperatures of 95° C. Effort was also made to reduce or eliminate any impact of emulsion system additives on the sample or PCR reagents.

Example 13

Multiple Emulsions to Control Density and Spacing

This Example describes the benefits of using multiple emulsions for a digital assay.

When there is a mismatch in refractive index between emulsion system components, it can be desirable to position the droplets as close as possible to the microscope objective during imaging. For an inverted microscope, it is possible to allow the droplets to settle on the bottom of the container, assuming the droplet density is greater than the density of the surrounding fluid. When mineral oil is used as a continuous carrier phase, the aqueous droplets are denser than the continuous phase, which causes them to settle on the bottom. However, when fluorocarbon-based oils are used as a continuous carrier phase, aqueous droplets will float to the top of the fluid.

The location of the sample droplets can be controlled through the use of double emulsions. In a water/oil/water double emulsion system, a fluorocarbon oil can be used as a middle layer, which causes aqueous droplets to sink to the bottom of the outer aqueous phase.

Figure 17:
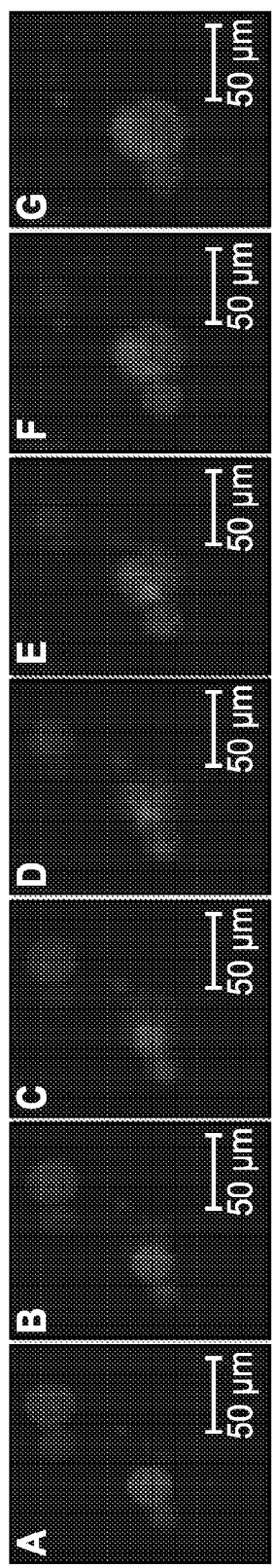
FIG. 17 shows fluorescence images of a water/oil/water double emulsion.

Two surfactants were tested (e.g., Tween 20 and Span 80) for the production of a secondary water layer. A system including 1% Span 80 was found to effectively yield a secondary water layer. It was observed that water/oil/water emulsions formed with pure fluorocarbon oil (e.g., FC-40) or in some combination with fluorocarbon solvents for index matching had large amounts of water/oil droplets clumped in the secondary droplet. Highly viscous fluorocarbon oils such as Krytox GPL-107 were added to increase the viscosity of FC-40 such that the water/oil emulsion does not immediately rise and clump together above the bulk oil phase. With this method, generated water/oil/water emulsions were less likely to have large amounts of water/oil droplets clumped inside the secondary droplet (FIG. 17). Spacing of aqueous droplets can be controlled by varying the viscosity of the oil phase.

FIG. 17 shows fluorescence images of a water/oil/water double emulsion made in a two-step emulsification process: First an aqueous solution containing PCR reagents was emulsified in an oil mixture composed of Krytox GPL-107, Fluorinert FC-40 and Pico-Surf 1 surfactant. The resulting water/oil emulsion was then further emulsified into an aqueous solution composed of water and Span 80 surfactant to produce a water/oil/water double emulsion. Because the oil phase is, in this case, denser than either aqueous phase, gravity lowers the double-emulsed droplets into closer proximity to the imaging objective. Images were acquired with a confocal microscope at progressively deeper (from left to right) focal planes (in 3 μm intervals). In addition to providing the advantage of better separating droplets, which can result in improved imaging, these results demonstrate that double emulsions can be helpful in minimizing the impact of refractive index mismatching by modifying the density of the droplets.

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

What is claimed is:

1. A method for performing a digital assay, the method comprising:
producing a plurality of polydisperse droplets, wherein at least some of droplets of the plurality of polydisperse droplets comprise a sample, the sample comprising a target molecule;
amplifying the sample to produce an amplified product, wherein amplifying the sample comprises amplifying the target molecule or molecules associated with the target molecule;

associating the amplified product with a detectable agent;
obtaining an image stack of the plurality of polydisperse droplets, wherein the image stack comprises a plurality of images from a plurality of focal planes;
measuring a volume of a droplet of the plurality of polydisperse droplets using the plurality of the images;
detecting from the image stack a presence or absence of the amplified product and the detectable agent in the droplet; and
determining the concentration of the target molecule in the plurality of polydisperse droplets based on the presence or absence of the detectable agent and the amplified product in the plurality of polydisperse droplets and the volume of at least some of the plurality of polydisperse droplets.

2. The method of claim 1, further comprising: forming an emulsion comprising an aqueous phase and a non-aqueous phase.

3. The method of claim 1, wherein the plurality of polydisperse droplets further comprises a fluid interface modification element.

4. The method of claim 3, wherein the fluid interface modification element is a surfactant.

5. The method of claim 1, wherein amplifying the sample comprises performing polymerase chain reaction (PCR), rolling circle amplification (RCA), nucleic acid sequence based amplification (NASBA), loop-mediated amplification (LAMP), or any combination thereof.

6. The method of claim 1, wherein amplifying the sample comprises performing antibody-based amplification.

7. The method of claim 1, wherein the distribution of droplet diameters has a standard deviation greater than 5% of the mean droplet diameter.

8. The method of claim 1, wherein the volumes in the polydisperse droplets vary by more than a factor of 2.

9. The method of claim 1, wherein the presence or absence of the amplified product and the detectable agent in the droplet is detected from at least one of the plurality of focal planes in the image stack.

10. The method of claim 1, wherein measuring the volume of the droplet further comprises:
correlating between the plurality of images and a largest diameter of the droplet; and
determining the volume of the droplet therefrom.

11. The method of claim 1, wherein measuring the volume of the droplet further comprises:
extrapolating a largest diameter of the droplet from the plurality of images; and
determining the volume of the droplet therefrom.

12. The method of claim 1, wherein the sample comprises a nucleotide, and wherein the sample comprises a nucleic acid amplification reagent selected from: a thermostable DNA polymerase, a nucleotide, a primer, a probe, or any combination thereof.

13. The method of claim 1, wherein the method is performed in a multi-well plate.

14. The method of claim 1, wherein the detecting comprises imaging with an optical imaging source, wherein the optical imaging source is configured to perform one or more of confocal microscopy, line confocal microscopy, deconvolution microscopy, spinning disk microscopy, multi-photon microscopy, planar illumination microscopy, Bessel beam microscopy, differential interference contrast microscopy, phase contrast microscopy, epiflouorescent microscopy, bright field imaging, dark field imaging, oblique illumination, or any combination thereof.

15. The method of claim 1, wherein the measuring the volume of the droplet further comprises:
identifying at least one pixel set in at least one image of the plurality of images;
identifying the at least one pixel set as corresponding to at least a part of at least one droplet;
identifying at least one individual droplet based on the correspondence; and
measuring the volume of the identified at least one individual droplet based on the at least one pixel set.

16. A method for performing a digital assay, the method comprising:
producing a plurality of polydisperse droplets having a distribution of droplet diameters with a standard deviation greater than 5% of a mean droplet diameter, wherein at least some of the plurality of polydisperse droplets comprise a sample, the sample comprising a target molecule;
amplifying the sample to produce an amplified product, wherein amplifying the sample comprises amplifying the target molecule or molecules associated with the target molecule;
associating the amplified product with a detectable agent;
imaging the plurality of polydisperse droplets to obtain a plurality of images of the plurality of polydisperse droplets from a plurality of focal planes;
measuring a volume of at least one droplet of the polydisperse droplets using the plurality of the images;
detecting a presence or absence of the amplified product and the detectable agent in the at least one droplet; and
determining a concentration of the target molecule in the plurality of polydisperse droplets based on the presence or absence of the amplified product and the detectable agent in the plurality of polydisperse droplets and the volume of at least some of the plurality of polydisperse droplets.

17. The method of claim 16, wherein the at least one droplet comprises at least 1,000 droplets.

18. The method of claim 16, wherein the measuring the volume of the at least one droplet further comprises:
correlating between the plurality of images and a largest diameter of the droplet: and determining the volume of the droplet therefrom.

19. The method of claim 16, wherein the measuring the volume of the at least one droplet further comprises:
extrapolating a largest diameter of the droplet from a plurality of; and
determining the volume of the droplet therefrom.

* * * * *